(12) United States Patent
Babcock et al.

(10) Patent No.: US 8,236,328 B2
(45) Date of Patent: Aug. 7, 2012

(54) PHARMACEUTICAL COMPOSITIONS OF DISPERSIONS OF AMORPHOUS DRUGS MIXED WITH POLYMERS

(75) Inventors: Walter C. Babcock, Bend, OR (US); William J. Curatolo, Niantic, CT (US); Dwayne T. Friesen, Bend, OR (US); Rodney J. Ketner, Bend, OR (US); Julian B. Lo, Old Lyme, CT (US); James A. S. Nightingale, Bend, OR (US); Ravi M. Shanker, Groton, CT (US); James B. West, Bend, OR (US)

(73) Assignee: Bend Research, Inc., Bend, OR (US)

( * ) Notice: Subject to any disclaimer, the term of this patent is extended or adjusted under 35 U.S.C. 154(b) by 1055 days.

(21) Appl. No.: 12/217,700

(22) Filed: Jul. 8, 2008

(65) Prior Publication Data

US 2009/0011024 A1 Jan. 8, 2009

(51) Int. Cl.
*A61K 9/00* (2006.01)
*A61K 9/14* (2006.01)

(52) U.S. Cl. ........ 424/400; 424/489; 424/485; 424/486; 424/487; 514/313

(58) Field of Classification Search .................. 424/400, 424/489, 485, 486, 487; 514/313
See application file for complete search history.

(56) References Cited

U.S. PATENT DOCUMENTS

2002/0103225 A1 * 8/2002 Curatolo et al. ............. 514/313

FOREIGN PATENT DOCUMENTS

| CA | 2 298 245 A1 | * | 9/2000 |
| EP | 1 027 886 A2 | * | 8/2000 |

* cited by examiner

*Primary Examiner* — Blessing Fubara
(74) *Attorney, Agent, or Firm* — Chernoff, Vilhauer, McClung & Stenzel

(57) ABSTRACT

A pharmaceutical composition comprises a dispersion comprising a low-solubility drug and a matrix combined with a concentration-enhancing polymer. At least a major portion of the drug is amorphous in the dispersion. The compositions improve the stability of the drug in the dispersion, and/or the concentration of drug in a use environment.

15 Claims, No Drawings

PHARMACEUTICAL COMPOSITIONS OF DISPERSIONS OF AMORPHOUS DRUGS MIXED WITH POLYMERS

This application is a continuation of Ser. No. 10/175,640 filed Jun. 19, 2002 and claims priority of Provisional Application Ser. No. 60/300,261 filed Jun. 22, 2001, which is incorporated herein by reference in its entirety for all purposes.

BACKGROUND OF THE INVENTION

The invention relates to compositions of a dispersion comprising amorphous drug and a matrix combined with a concentration-enhancing polymer that improves the stability of the drug and/or enhances the concentration of the drug in a use environment.

Low-solubility drugs often show poor bioavailability or irregular absorption, the degree of irregularity being affected by factors such as dose level, fed state of the patient, and form of the drug. Increasing the bioavailability of low-solubility drugs has been the subject of much research. Increasing bioavailability hinges on improving the concentration of the drug in solution to improve absorption.

It is well known that the amorphous form of a low-solubility drug that is capable of existing in either the crystalline or amorphous form may temporarily provide a greater aqueous concentration of drug relative to the equilibrium concentration obtained by dissolution of drug in a use environment. Such amorphous forms may consist of the amorphous drug alone, a dispersion of the drug in a matrix material, or the drug adsorbed onto a substrate. It is believed that such amorphous forms of the drug may dissolve more rapidly than the crystalline form, often dissolving faster than the drug can precipitate from solution. As a result, the amorphous form may temporarily provide a greater-than equilibrium concentration of drug.

While such amorphous forms may show initially enhanced concentration of the drug in a use environment, nevertheless the improved concentration is often short-lived. Typically, the initially enhanced drug concentration is only temporary and quickly returns to the lower equilibrium concentration.

One approach to increase the bioavailability of low-solubility drugs has involved forming amorphous dispersions of drugs with polymers. Examples of attempts to increase drug concentration by forming a dispersion of the drug with a polymer include Lahr et al., U.S. Pat. No. 5,368,864, Kanikanti et al., U.S. Pat. No. 5,707,655, and Nakamichi et al., U.S. Pat. No. 5,456,923.

Curatolo et al., EP 0901786A2, disclose solid amorphous dispersions of poorly water soluble drugs and hydroxypropylmethyl cellulose acetate succinate (HPMCAS). In one embodiment, HPMCAS is a dispersion polymer.

Alternatively, a dispersion may be formed of a drug and conventional matrix material such as PVP, HPC or HPMC and then the dispersion is triturated with HPMCAS.

One problem with using the amorphous form of a drug is that the solid drug may not be stable physically in the amorphous form. Often the crystalline form of the drug has a lower free energy, and thus over time, the amorphous drug will tend to crystallize. The rate of crystallization may be influenced by storage conditions, such as temperature and humidity, as well as the constituents of the composition.

Similarly, even if a dispersion of drug and polymer is formed, the drug in the resulting amorphous dispersion of polymer and drug may in some cases be unstable. For example, the dispersion may be physically unstable, causing the amorphous drug to separate from the dispersion and/or crystallize. Alternatively, the drug in the amorphous dispersion may be chemically unstable. The drug may degrade over time at moderate temperature and humidity levels or the drug may convert to a lower energy and lower solubility amorphous or crystalline form.

Alternatively, it may be difficult or, in some cases, impossible to form a dispersion of the drug and preferred polymer. In particular, the drug and preferred polymer may not both be amenable to a processing method that results in a dispersion of the drug and preferred polymer. For example, when solvent processing is the preferred method for forming the dispersion, the drug and preferred polymer may not both be soluble to a sufficient extent in an appropriate processing solvent to allow formation of the dispersion. In cases where melt processing is preferred, the drug or polymer or both may suffer unacceptable decomposition upon heating to allow the formation of the preferred composition to be practical.

Accordingly, what is still desired is a composition comprising an amorphous drug that is physically and/or chemically stable under typical storage conditions, may be formed via practical processing conditions, and that may enhance the bioavailability of poorly soluble drugs. These needs and others that will become apparent to one of ordinary skill are met by the present invention, which is summarized and described in detail below.

BRIEF SUMMARY OF THE INVENTION

The present invention, in one aspect, relates to pharmaceutical compositions comprising: (a) a solid dispersion comprising a low-solubility drug and a matrix, wherein at least a major portion of said drug in said dispersion is amorphous; and (b) a concentration-enhancing polymer, said dispersion being free from at least a portion of said concentration-enhancing polymer; wherein said composition provides improved stability of said drug relative to at least one of a first control composition consisting of a mixture of said low-solubility drug in undispersed amorphous form and said concentration-enhancing polymer, and a second control composition consisting of a dispersion of said low-solubility drug and said concentration-enhancing polymer.

In a second aspect, the present invention relates to pharmaceutical compositions comprising: (a) a solid dispersion comprising a low-solubility drug and a matrix, wherein at least a major portion of said drug in said dispersion is amorphous; and (b) a concentration-enhancing polymer, said dispersion being free from at least a portion of said concentration-enhancing polymer; wherein at least 10 wt % of said matrix is non-polymeric.

In a third aspect, the present invention relates to pharmaceutical compositions comprising: (a) a solid dispersion comprising a low-solubility drug and a matrix, wherein at least a major portion of said drug in said dispersion is amorphous; and (b) a concentration-enhancing polymer, said dispersion being free from at least a portion of said concentration-enhancing polymer; wherein said concentration-enhancing polymer is non-cellulosic.

In a fourth aspect, the present invention relates to pharmaceutical compositions, comprising: (a) a solid dispersion comprising a low-solubility drug and a matrix, wherein at least a major portion of said drug in said dispersion is amorphous; and (b) a concentration-enhancing polymer, said dispersion being free from at least a portion of said concentration-enhancing polymer, wherein said concentration-enhancing polymer is selected from the group consisting of non-ionizable cellulosic polymers and neutralized acidic polymers.

In a fifth aspect, the present invention relates to pharmaceutical compositions, comprising: (a) a solid dispersion comprising a low-solubility drug and a matrix, wherein at least a major portion of said drug in said dispersion is amorphous; and (b) a concentration-enhancing polymer, said dispersion being free from at least a portion of said concentration-enhancing polymer, wherein said concentration-enhancing polymer is an ionizable cellulosic polymer having at least one of an ester-linked carboxylic acid-functional aromatic substituent and an ether-linked carboxylic acid-functional aromatic substituent.

In a sixth aspect, the present invention relates to pharmaceutical compositions, comprising: (a) a solid dispersion comprising a low-solubility drug and a matrix, wherein at least a major portion of said drug in said dispersion is amorphous; (b) an amphiphilic, cellulosic concentration-enhancing polymer, said dispersion being free from at least a portion of said amphiphilic, cellulosic concentration-enhancing polymer; (c) said amphiphilic cellulosic concentration-enhancing polymer having at least one hydrophobic substituent selected from the group consisting of ether-linked alkyl substituents, ester-linked alkyl substituents, ether-linked aryl substituents and ester-linked aryl substituents; (d) said amphiphilic cellulosic concentration-enhancing polymer having at least one hydrophilic substituent selected from the group consisting of ether-linked hydroxy alkyl substituents, ester-linked hydroxy alkyl substituents, alkyl ether groups, ester-linked ionizable substituents, and ether-linked ionizable substituents; and (e) provided that when said concentration-enhancing polymer has both the hydrophilic substituents hydroxypropyl and succinate, said polymer is free from both an ether-linked methyl substituent and an ester-linked acetate substituent.

In a preferred embodiment, the drug has improved physical stability in said composition relative to said first control composition.

In another preferred embodiment, at least a major portion of said drug is dissolved in said matrix.

In another preferred embodiment, the drug has a solubility in said matrix that is at least 30% of a concentration of said drug in said matrix.

In another preferred embodiment, the drug has a weight ratio to said matrix of said dispersion of less than 20.

In yet another preferred embodiment, the dispersion has a glass transition temperature that is greater than a glass transition temperature of at least one of said low-solubility drug in undispersed amorphous form and said second control composition.

In another preferred embodiment, the dispersion has a glass transition temperature that is greater than about 50° C. at 50% relative humidity.

In another preferred embodiment, the drug in said dispersion has a crystallization rate that is less than 90% of a crystallization rate of said drug in undispersed amorphous form.

In another preferred embodiment, the drug in said composition has a relative degree of improvement in chemical stability of at least 1.25 relative to at least one of said first control composition and said second control composition.

In still another preferred embodiment, the drug is acid-sensitive and said concentration-enhancing polymer is acidic.

In another preferred embodiment, the drug in said composition has improved stability, preferably improved physical stability, relative to at least one of a first control composition consisting of a mixture of said low-solubility drug in undispersed amorphous form and said concentration-enhancing polymer, and a second control composition comprising a dispersion of said drug and said concentration-enhancing polymer.

In another preferred embodiment, at least 10 wt % of said matrix is non-polymeric. Preferred components of said matrix are selected from the group consisting of alcohols, organic acids, organic bases, amino acids, sugars, fatty acid esters, alkyl sulfates, phospholipids, waxes and salts.

In yet another preferred embodiment, the matrix has at least one polymeric component. Preferred components of said matrix are selected from the group consisting of polyethylene glycols, polyoxyethylene glycols, polyethylene-polypropylene glycol copolymers, polyethylene oxides, polyvinylpyrrolidone, polyvinyl alcohols, polyethylene-vinyl alcohol copolymers, polyvinyl alcohol polyvinyl acetate copolymers, carboxylic acid-functionalized polymethacrylates, amine-functionalized polymethacrylates, proteins, xanthan gum, carrageenan, hydroxypropyl cellulose, hydroxypropyl methyl cellulose, carboxy methyl cellulose, chitosan, chitin, polydextrose, dextrin and starch.

In another preferred embodiment, the drug is substantially amorphous in said dispersion.

In another preferred embodiment, the dispersion is substantially homogeneous.

In another preferred embodiment, the dispersion is completely homogeneous.

In another preferred embodiment, the composition is a solid mixture in which said concentration-enhancing polymer is suspended as a separate phase within said dispersion.

In another preferred embodiment, the composition is a mixture of particles of dispersion and particles of concentration-enhancing polymer.

In another preferred embodiment, the mixture is formed by at least one of dry-granulation and wet-granulation.

In another preferred embodiment, the dispersion and said concentration-enhancing polymer are each in separate regions.

In another preferred embodiment, the compositions further comprise a blend of concentration-enhancing polymers selected from the group consisting of ionizable cellulosic polymers, non-ionizable cellulosic polymers, ioniziable non-cellulosic polymers, non-ionizable non-cellulosic polymers, and neutralized acidic polymers.

In still another preferred embodiment, the concentration-enhancing polymer has a hydrophobic portion and a hydrophilic portion.

In another preferred embodiment, the concentration-enhancing polymer is an ionizable cellulosic polymer such as polymers selected from the group consisting of hydroxypropyl methyl cellulose succinate, cellulose acetate succinate, methyl cellulose acetate succinate, ethyl cellulose acetate succinate, hydroxypropyl cellulose acetate succinate, hydroxypropyl methyl cellulose acetate succinate, hydroxypropyl cellulose acetate phthalate succinate, cellulose propionate succinate, hydroxypropyl cellulose butyrate succinate, hydroxypropyl methyl cellulose phthalate, cellulose acetate phthalate, methyl cellulose acetate phthalate, ethyl cellulose acetate phthalate, hydroxypropyl cellulose acetate phthalate, hydroxypropyl methyl cellulose acetate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, ethyl picolinic acid cellulose acetate, carboxy methyl cellulose, carboxy ethyl cellulose, ethyl carboxy methyl cellulose, and blends thereof. More preferably, the concentration-enhancing polymer is selected from the group consisting of hydroxypropyl methyl cellulose acetate succinate, hydroxypropyl methyl cellulose phthalate, cellulose acetate phthalate, and cellulose acetate trimellitate, and blends thereof.

In another preferred embodiment, the concentration-enhancing polymer is a non-ionizable cellulosic polymer, such as polymers selected from the group consisting of hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose, and blends thereof.

In another preferred embodiment, the concentration-enhancing polymer is an ionizable, non-cellulosic polymer, such as polymers selected from the group consisting of carboxylic acid functionalized polymethacrylates, carboxylic acid functionalized polyacrylates, amine-functionalized polyacrylates, amine-fuctionalized polymethacrylates, proteins, and carboxylic acid functionalized starches, and blends thereof.

In another preferred embodiment, the concentration-enhancing polymer is a non-ionizable, non-cellulosic polymer such as polymers selected from the group consisting of vinyl polymers and copolymers having at least one substituent selected from the group consisting of hydroxyl, alkylacyloxy, and cyclicamido; vinyl copolymers of at least one hydrophilic, hydroxyl-containing repeat unit and at least one hydrophobic, alkyl- or aryl-containing repeat unit; polyvinyl alcohols that have at least a portion of their repeat units in the unhydrolyzed form, polyvinyl alcohol polyvinyl acetate copolymers, polyethylene glycol polypropylene glycol copolymers, polyvinyl pyrrolidone, and polyethylene polyvinyl alcohol copolymers, and blends thereof.

In yet another preferred embodiment, the concentration-enhancing polymer is selected from the group consisting of hydroxypropyl cellulose acetate phthalate succinate, hydroxypropyl methyl cellulose phthalate, cellulose acetate phthalate, methyl cellulose acetate phthalate, ethyl cellulose acetate phthalate, hydroxypropyl cellulose acetate phthalate, hydroxypropyl methyl cellulose acetate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, ethyl picolinic acid cellulose acetate, carboxy methyl cellulose, carboxy ethyl cellulose, ethyl carboxy methyl cellulose, and blends thereof.

In another preferred embodiment, the amphiphilic, cellulosic concentration-enhancing polymer is selected from the group consisting of hydroxypropyl cellulose acetate succinate, hydroxypropyl methyl cellulose, hydroxypropyl methyl cellulose acetate, hydroxypropyl methyl cellulose succinate, hydroxypropyl methyl cellulose phthalate, hydroxypropyl methyl cellulose acetate phthalate, hydroxyethyl methyl cellulose, hydroxyethyl methyl cellulose succinate, hydroxyethyl cellulose acetate succinate, hydroxyethyl methyl cellulose acetate succinate, hydroxyethyl methyl cellulose acetate phthalate, hydroxyethyl cellulose acetate, hydroxyethyl ethyl cellulose, carboxymethyl ethyl cellulose, cellulose acetate phthalate, hydroxypropyl cellulose acetate phthalate, methyl cellulose acetate phthalate, ethyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate, and blends thereof.

In still another preferred embodiment, at least a portion of said concentration-enhancing polymer is neutralized. In other preferred embodiments, concentration-enhancing polymer is a neutralized acidic polymer.

In still another preferred embodiment, the composition when administered to a use environment provides a dissolution area under the concentration versus time curve for a time period of at least 90 minutes during the 270 minutes immediately following introduction to said use environment that is at least 1.25-fold the corresponding area under the curve provided by a control composition comprising an equivalent amount of undispersed amorphous drug alone.

In another preferred embodiment, the composition when administered to a use environment provides a maximum concentration of said drug in said use environment that is at least 1.25-fold a maximum concentration of said drug provided by a control composition comprising an equivalent amount of undispersed amorphous drug alone.

In another preferred embodiment, the composition when administered to an animal provides a relative bioavailability of at least 1.25 relative to a control composition comprising an equivalent amount of undispersed amorphous drug alone.

In another preferred embodiment, the composition when administered to a use environment provides a dissolution area under the concentration versus time curve for a time period of at least 90 minutes during the 270 minutes immediately following introduction to said use environment that is at least 1.25-fold the corresponding area under the curve provided by a control composition comprising an equivalent amount of said dispersion but with no concentration-enhancing polymer.

In another preferred embodiment, the composition when administered to a use environment provides a maximum concentration of said drug in said use environment that is at least 1.25-fold a maximum concentration of said drug provided by a control composition comprising an equivalent amount of said dispersion but with no concentration-enhancing polymer.

In another preferred embodiment, the composition when administered to an animal provides a relative bioavailability of at least 1.25 relative to a control composition comprising an equivalent amount of said dispersion but with no concentration-enhancing polymer.

In another preferred embodiment, the drug is selected from the group consisting of antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, anti-atherosclerotic agents, glycogen phosphorylase inhibitors, and cholesterol ester transfer protein inhibitors.

In another preferred embodiment, the drug is a glycogen phosphorylase inhibitor selected from the group consisting of [R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide.

In another preferred embodiment, the drug is a cholesterol ester transfer protein inhibitor selected from the group consisting of [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]-4-[3,5-bis-trifluoromethyl-benzyl)-methoxycarbonyl-amino]-2-ethyl-6-trifluoromethyl-3,4-dihydro-2H-quinoline-1-carboxylic acid ethyl ester, and [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester.

In a seventh aspect, the present invention relates to methods of administering a drug comprising co-administering to a patient in need of said drug: (a) a solid dispersion comprising a low-solubility drug and a matrix, wherein at least a major portion of said drug in said dispersion is amorphous; and (b) a concentration-enhancing polymer, said dispersion being free from at least a portion of said concentration-enhancing polymer; wherein said dispersion provides improved stability of said drug relative to at least one of a first control composition consisting of a mixture of said low-solubility drug in undispersed amorphous form and said concentration-enhancing polymer, and a second control composition consisting of a dispersion of said low-solubility drug and said concentration-enhancing polymer.

In a preferred embodiment, the dispersion is administered separately from said concentration-enhancing polymer.

In another preferred embodiment, the dispersion and said concentration-enhancing polymer are administered at approximately the same time.

In another preferred embodiment, the dispersion and said concentration-enhancing polymer are present in a single dosage form.

The present invention also relates to, in an eighth aspect, methods of administering a drug comprising co-administering to a patient in need of said drug: (a) a solid dispersion comprising a low-solubility drug and a matrix, wherein at least a major portion of said drug in said dispersion is amorphous; and (b) a concentration-enhancing polymer, said dispersion being free from at least a portion of said concentration-enhancing polymer; wherein at least 10 wt % of said matrix is non-polymeric.

In a ninth aspect, the present invention relates to methods of administering a drug comprising co-administering to a patient in need of said drug: (a) a solid dispersion comprising a low-solubility drug and a matrix, wherein at least a major portion of said drug in said dispersion is amorphous; and (b) a concentration-enhancing polymer, said dispersion being free from at least a portion of said concentration-enhancing polymer; wherein said concentration-enhancing polymer is non-cellulosic.

In a tenth aspect, the present invention relates to methods of administering a drug comprising co-administering to a patient in need of said drug: (a) a solid dispersion comprising a low-solubility drug and a matrix, wherein at least a major portion of said drug in said dispersion is amorphous; and (b) a concentration-enhancing polymer, said dispersion being free from at least a portion of said concentration-enhancing polymer, wherein said concentration-enhancing polymer is selected from the group consisting of non-ionizable cellulosic polymers and neutralized acidic polymers.

In an eleventh aspect, the present invention relates to methods of administering a drug comprising co-administering to a patient in need of said drug: (a) a solid dispersion comprising a low-solubility drug and a matrix, wherein at least a major portion of said drug in said dispersion is amorphous; and (b) a concentration-enhancing polymer, said dispersion being free from at least a portion of said concentration-enhancing polymer, wherein said concentration-enhancing polymer is an ionizable cellulosic polymer having at least one of an ester-linked carboxylic acid-functional aromatic substituent and an ether-linked carboxylic acid-functional aromatic substituent.

In a twelfth aspect, the present invention relates to methods of administering a drug comprising co-administering to a patient in need of said drug: (a) a solid dispersion comprising a low-solubility drug and a matrix, wherein at least a major portion of said drug in said dispersion is amorphous; (b) an amphiphilic, cellulosic concentration-enhancing polymer, said dispersion being free from at least a portion of said amphiphilic, cellulosic concentration-enhancing polymer; (c) said amphiphilic cellulosic concentration-enhancing polymer having at least one hydrophobic substituent selected from the group consisting of ether-linked alkyl substituents, ester-linked alkyl substituents, ether-linked aryl substituents and ester-linked aryl substituents; (d) said amphiphilic cellulosic concentration-enhancing polymer having at least one hydrophilic substituent selected from the group consisting of ether-linked hydroxy alkyl substituents, ester-linked hydroxy alkyl substituents, alkyl ether substituents, ester-linked ionizable substituents, and ether-linked ionizable substituents; and (e) provided that when said concentration-enhancing polymer has both the hydrophilic substituents hydroxypropyl and succinate, said polymer is free from both an ether-linked methyl group and an ester-linked acetate group.

The solid compositions of the present invention are combinations comprising (1) a dispersion of a low-solubility drug and matrix and (2) concentration-enhancing polymer(s). "Combination" as used herein means that the drug/matrix dispersion and concentration-enhancing polymer may be in physical contact with each other or in close proximity but are not mixed at the molecular level so as to form a solid molecular dispersion. In other words, although the drug/matrix dispersion and the concentration-enhancing polymer may be mixed, they remain as separate phases retaining their own physical properties such as melting points or glass-transition temperatures. Thus, the dispersion of the drug and matrix is free from at least a portion, if not all, of the concentration-enhancing polymer.

Alternatively, the drug/matrix dispersion and concentration-enhancing polymer may be co-administered to a patient in need of the drug. The dispersion and concentration-enhancing polymer may be administered in separate or the same dosage forms, and may also be administered at essentially the same time or at different times.

The present invention achieves its advantages by combining a dispersed amorphous drug with a concentration-enhancing polymer. One key to the present invention was the recognition by the inventors that the initially enhanced concentration of the drug in solution provided by the amorphous drug could be maintained, and in some cases enhanced by the interaction of the drug and concentration-enhancing polymer being present together in the use environment. Thus, without implying any particular mechanism of action, it is believed that the concentration-enhancing polymers of this invention may be viewed as acting as crystallization or precipitation inhibitors. In some cases, the concentration-enhancing polymers may also interact to form various types of polymer-drug assemblies such as aggregates or colloids. Surprisingly, this may be accomplished by simply combining the concentration-enhancing polymer with the dispersion, in contrast to forming a molecular dispersion of the drug, matrix and concentration-enhancing polymer.

Regardless of the mechanism, the compositions provide improved concentration of drug in the use environment. The drug/matrix dispersion, when introduced to a use environment, provides an initial concentration of drug that exceeds the equilibrium concentration of drug, while the concentration-enhancing polymer retards the rate at which the initially enhanced drug concentration falls to the equilibrium concentration. Thus, the compositions of the present invention provide a dissolution area-under-the-concentration-versus-time-curve ("AUC") that is greater than that provided by crystalline drug alone. In preferred embodiments, the compositions of the present invention provide an AUC that is greater than that provided by either the drug/matrix dispersion itself or by the drug in undispersed amorphous form and concentration-enhancing polymer.

Preferably, the compositions provide a maximum drug concentration that exceeds the maximum drug concentration provided by either a control consisting of the dispersion itself or by a control consisting of the undispersed amorphous drug plus concentration-enhancing polymer. Nevertheless, the advantages of the invention may be obtained by merely retarding the rate at which the enhanced drug concentration falls to the equilibrium concentration, even without increasing the maximum drug concentration relative to a control composition.

As a result of improving the dissolution AUC, the compositions of the present invention may also provide enhanced bioavailability of the drug by increasing the concentration of drug which remains dissolved in the use environment, particularly in the GI tract. Improving the concentration of the drug in solution allows more rapid absorption of drug and, as a result, higher blood levels to be achieved. In some cases this enhanced absorption rate enables an effective level of drug to be reached that might not be reached by administration of conventional forms of the drug. In other cases, administration of the compositions of the invention allows effective blood levels to be reached at lower drug dosage levels, which in turn decreases the amount of drug that must be dosed, and reduces the blood level variability. Such compositions may also allow the size of the dosage form to be decreased, depending on the amount of polymer needed.

Furthermore, because the compositions of the present invention provide for a higher concentration of drug dissolved in the use environment, and because once a high drug concentration is achieved the concentration tends to remain high due to inhibition of precipitation or crystallization of the drug, the compositions may have a number of positive effects. First, in cases where the use environment is the GI tract, the compositions of the present invention may show less variability in drug absorption as a result of variation in the fed/fasted state of the GI tract of the human or animal. Second, due to a prolonged high drug concentration in the GI tract, absorption of drug may continue over a longer time period and an effective concentration of drug in the blood may be maintained over a longer time period.

Stabilizing the drug in a dispersion of the drug and matrix and then combining the dispersion with the concentration-enhancing polymer provides another of the advantages of the present invention, which is to allow the use of concentration-enhancing polymers which, for whatever reason, are not suitable for forming a molecular dispersion with the particular drug. In one embodiment, the invention solves the problem presented where it is difficult to combine the preferred concentration-enhancing polymer and drug to form a stable molecular dispersion. The difficulty in forming a stable dispersion may be due to adverse interactions between the drug and polymer in the dispersion, resulting in chemical and/or physical instability of the drug in the dispersion. For example, although an acidic cellulosic polymer may provide superior concentration-enhancement for some drugs, such polymers may chemically degrade acid-sensitive drugs when present in the dispersion.

Alternatively, the preferred concentration-enhancing polymer may not be amenable to the preferred process used to form dispersions of the drug. For example, cellulosic polymers do not readily melt, and thus are not suitable for use in forming dispersions of drug and the cellulosic polymer by use of most melt-fusion processes. As another example, the mobility of polymers having a high glass transition temperature is too low to allow use of mechanical processes, such as ball milling, to form dispersions. Alternatively, the drug and concentration-enhancing polymer may not share a common solvent, thus precluding the formation of a dispersion of the drug and concentration-enhancing polymer using solvent processing.

The present invention solves these problems by forming an amorphous dispersion of the drug in an alternative matrix material to form a drug/matrix dispersion, and then combines the drug/matrix dispersion with the concentration-enhancing polymer to form the composition. This provides the benefit of either improved drug stability or use of a preferred processing method while at the same time providing the additional level of concentration-enhancement conferred by the presence of the concentration-enhancing polymer.

The foregoing and other objectives, features, and advantages of the invention will be more readily understood upon consideration of the following detailed description of the invention.

DETAILED DESCRIPTION OF THE PREFERRED EMBODIMENTS

The present invention provides in one aspect a composition comprising (1) a solid dispersion comprising a low-solubility drug and matrix, wherein at least a major portion of the drug in the dispersion is amorphous and (2) a concentration-enhancing polymer, wherein the drug in the composition has improved chemical or physical stability relative to an appropriate control composition. In another aspect, the invention comprises (1) a solid dispersion comprising a low-solubility drug and a matrix, wherein at least a major portion of the drug in the dispersion is amorphous and (2) a concentration-enhancing polymer, wherein the concentration-enhancing polymer is present in a sufficient amount so that the composition improves the concentration of the drug in a use environment relative to an appropriate control composition. In yet another aspect, the invention provides a method for co-administering (1) a solid amorphous dispersion comprising a low-solubility drug and a matrix, and (2) a concentration-enhancing polymer. Suitable drug(s), matrices, and concentration-enhancing polymer(s), as well as methods for preparing the compositions, are discussed in detail below.

The Drug

The present invention is useful with any drug capable of being formulated as an amorphous drug. The term "drug" is conventional, denoting a compound having beneficial prophylactic and/or therapeutic properties when administered to an animal, especially humans. The drug does not need to be a low-solubility drug in order to benefit from this invention, although low-solubility drugs represent a preferred class for use with the invention. Even a drug that nonetheless exhibits appreciable solubility in the desired environment of use can benefit from the increased solubility/bioavailability made possible by this invention if the addition of the concentration-enhancing polymer can reduce the size of the dose needed for therapeutic efficacy or increase the rate of drug absorption in cases where a rapid onset of the drug's effectiveness is desired.

Preferably, the drug is a "low-solubility drug," meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL.

The invention finds greater utility as the solubility of the drug decreases. Thus, compositions of the present invention are preferred for low-solubility drugs having a solubility of less than 10 mg/mL, more preferred for low-solubility drugs having a solubility of less than 1 mg/mL, and even more preferred for low-solubility drugs having a solubility of less than 0.1 mg/mL. In general, it may be said that the drug has a dose-to-aqueous solubility ratio greater than 10 mL, and more typically greater than 100 mL, where the drug solubility (mg/mL) is the minimum value observed in any physiologically relevant aqueous solution (e.g., those with pH values between 1 and 8) including USP simulated gastric and intestinal buffers, and the dose is in mg. Thus, a dose-to-aqueous-solubility ratio may be calculated by dividing the dose (in mg) by the solubility (in mg/mL).

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesterol ester transfer protein inhibitors.

Each named drug should be understood to include the neutral form of the drug, pharmaceutically acceptable salts, as well as prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl)-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy) pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine, and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [(R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxopropyl]amide; and specific examples of cholesterol ester transfer protein (CETP) inhibitors include [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S] 4-[(3,5-Bis-trifluoromethyl-benzyl)-methoxycarbonyl-amino]-2-ethyl-6-trifluoromethyl-3,4-dihydro-2H-quinoline-1-carboxylic acid isopropyl ester.

The invention is not limited by any particular structure or group of CETP inhibitors. Rather, the invention has general applicability to CETP inhibitors as a class, the class tending to be composed of compounds having low solubility.

Compounds which may be the subject of the invention may be found in a number of patents and published applications, including DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; EP 992496; and EP 987251, all of which are hereby incorporated by reference in their entireties for all purposes.

The invention is useful for CETP inhibitors that have sufficiently low aqueous solubility, low bioavailability or slow rate of absorption such that it is desirable to increase their concentration in an aqueous environment of use.

Therefore, anytime one finds it desirable to raise the aqueous concentration of the CETP inhibitor in a use environment, the invention will find utility. The CETP inhibitor is "substantially water-insoluble" which means that the CETP inhibitor has a minimum aqueous solubility of less than about 0.01 mg/mL (or 10 μg/ml) at any physiologically relevant pH (e.g., pH 1-8) and at about 22° C. (Unless otherwise specified, reference to aqueous solubility herein and in the claims is determined at about 22° C.) Compositions of the present invention find greater utility as the solubility of the CETP inhibitors decreases, and thus are preferred for CETP inhibitors with solubilities less than about 2 μg/mL, and even more preferred for CETP inhibitors with solubilities less than about 0.5 μg/mL. Many CETP inhibitors have even lower solubilities (some even less than 0.1 μg/mL), and require dramatic concentration enhancement to be sufficiently bioavailable upon oral dosing for effective plasma concentrations to be reached at practical doses.

In general, it may be said that the CETP inhibitor has a dose-to-aqueous solubility ratio greater than about 100 mL, where the solubility (mg/mL) is the minimum value observed in any physiologically relevant aqueous solution (e.g., those with pH values from 1 to 8) including USP simulated gastric and intestinal buffers, and dose is in mg. Compositions of the present invention, as mentioned above, find greater utility as the solubility of the CETP inhibitor decreases and the dose increases. Thus, the compositions are preferred as the dose-to-solubility ratio increases, and thus are preferred for dose-to-solubility ratios greater than 1000 mL, and more preferred for dose-to-solubility ratios greater than about 5000 ml. The dose-to-solubility ratio may be determined by dividing the dose (in mg) by the aqueous solubility (in mg/ml).

Oral delivery of many CETP inhibitors is particularly difficult because their aqueous solubility is usually extremely low, typically being less than 2 μg/ml, often being less than 0.1 μg/ml. Such low solubilities are a direct consequence of the particular structural characteristics of species that bind to CETP and thus act as CETP inhibitors. This low solubility is primarily due to the hydrophobic nature of CETP inhibitors. Clog P, defined as the base 10 logarithm of the ratio of the drug solubility in octanol to the drug solubility in water, is a widely accepted measure of hydrophobicity. In general, Clog P values for CETP inhibitors are greater than 4 and are often greater than 5 to 7. Thus, the hydrophobic and insoluble nature of CETP inhibitors as a class pose a particular challenge for oral delivery. Achieving therapeutic drug levels in the blood by oral dosing of practical quantities of drug generally requires a large enhancement in drug concentrations in the gastrointestinal fluid and a resulting large enhancement in bioavailability. Such enhancements in drug concentration in gastrointestinal fluid typically need to be at least about 10-fold and often at least about 50-fold or even at least about 200-fold to achieve desired blood levels. Surprisingly, the dispersions of the present invention have proven to have the required large enhancements in drug concentration and bioavailability.

In contrast to conventional wisdom, the relative degree of enhancement in aqueous concentration and bioavailability generally improves for CETP inhibitors as solubility decreases and hydrophobocity increases. In fact, the inventors have recognized a subclass of these CETP inhibitors that are essentially aqueous insoluble, highly hydrophobic, and are characterized by a set of physical properties. This subclass exhibits dramatic enhancements in aqueous concentration and bioavailability when formulated using the compositions of the present invention.

The first property of this subclass of essentially insoluble, hydrophobic CETP inhibitors is extremely low aqueous solubility. By extremely low aqueous solubility is meant that the minimum aqueous solubility at physiologically relevant pH (pH of 1 to 8) is less than about 10 μg/ml and preferably less than about 1 μg/ml.

A second property is a very high does-to-solubility ratio. Extremely low solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of this subclass of essentially insoluble, hydrophobic CETP inhibitors is a very high dose (in mg) to solubility (in mg/ml) ratio (ml). By "very high dose-to-solubility ratio" is meant that the dose-to-solubility ratio has a value of at least 1000 ml, and preferably at least 5,000 ml, and more preferably at least 10,000 ml.

A third property of this subclass of essentially insoluble, hydrophobic CETP inhibitors is that they are extremely hydrophobic. By extremely hydrophobic is meant that the Clog P value of the drug, has a value of at least 4.0, preferably a value of at least 5.0, and more preferably a value of at least 5.5.

A fourth property of this subclass of essentially insoluble CETP inhibitors is that they have a low melting point. Generally, drugs of this subclass will have a melting point of about 150° C. or less, and preferably about 140° C. or less.

Primarily, as a consequence of some or all of these four properties, CETP inhibitors of this subclass typically have very low absolute bioavailabilities. Specifically, the absolute bioavailibility of drugs in this subclass when dosed orally in their undispersed state is less than about 10% and more often less than about 5%.

Turning now to the chemical structures of specific CETP inhibitors, one class of CETP inhibitors that finds utility with the present invention consists of oxy substituted 4-carboxyamino-2-methyl-1,2,3,4-tetrahydroquinolines having the Formula I

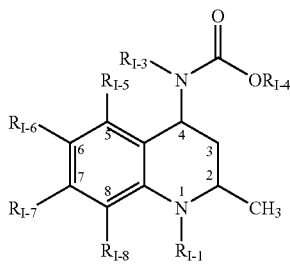

Formula I and pharmaceutically acceptable salts, enantiomers, or stereoisomers of said compounds;

wherein $R_{I-1}$ is hydrogen, $Y_I$, $W_I\!-\!X_I$, $W_I\!-\!Y_I$;

wherein $W_I$ is a carbonyl, thiocarbonyl, sulfinyl or sulfonyl;

$X_I$ is $-O-Y_I$, $-S-Y_I$, $-N(H)-Y_I$ or $-N-(Y_I)_2$;

wherein $Y_I$ for each occurrence is independently $Z_I$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_I$;

wherein $Z_I$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_I$ substituent is optionally mono-, di- or tri-substituted independently with halo, $(C_2\text{-}C_6)$alkenyl, $(C_1\text{-}C_6)$alkyl, hydroxy, $(C_1\text{-}C_6)$alkoxy, $(C_1\text{-}C_4)$alkylthio, amino, nitro, cyano, oxo, carboxyl, $(C_1\text{-}C_6)$alkyloxycarbonyl, mono-N— or di-N,N—$(C_1\text{-}C_6)$alkylamino wherein said $(C_1\text{-}C_6)$alkyl substituent is optionally mono-, di- or tri-substituted independently with halo, hydroxy, $(C_1\text{-}C_6)$alkoxy, $(C_1\text{-}C_4)$alkylthio, amino, nitro, cyano, oxo, carboxyl, $(C_1\text{-}C_6)$alkyloxycarbonyl, mono-N— or di-N,N—$(C_1\text{-}C_6)$alkylamino, said $(C_1\text{-}C_6)$alkyl substituent is also optionally substituted with from one to nine fluorines;

$R_{I-3}$ is hydrogen or $Q_I$;

wherein $Q_I$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_I$;

wherein $V_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_I$ substituent is optionally mono-, di-, tri-, or tetra-substituted independently with halo, $(C_1\text{-}C_6)$alkyl, $(C_2\text{-}C_6)$alkenyl, hydroxy, $(C_1\text{-}C_6)$alkoxy, $(C_1\text{-}C_4)$alkylthio, amino, nitro, cyano, oxo, carbamoyl, mono-N— or di-N,N—$(C_1\text{-}C_6)$alkylcarbamoyl, carboxyl, $(C_1\text{-}C_6)$alkyloxycarbonyl, mono-N— or di-N,N—$(C_1\text{-}C_6)$alkylamino wherein said $(C_1\text{-}C_6)$alkyl or $(C_2\text{-}C_6)$alkenyl substituent is optionally mono-, di- or tri-substituted independently with hydroxy, $(C_1\text{-}C_6)$alkoxy, $(C_1\text{-}C_4)$alkylthio, amino, nitro, cyano, oxo, carboxyl, $(C_1\text{-}C_6)$alkyloxycarbonyl, mono-N— or di-N,N—$(C_1\text{-}C_6)$alkylamino, said $(C_1\text{-}C_6)$alkyl or $(C_2\text{-}C_6)$alkenyl substituents are also optionally substituted with from one to nine fluorines;

$R_{I-4}$ is $Q_{I-1}$ or $V_{I-1}$ wherein $Q_{I-1}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{I-1}$;

wherein $V_{I-1}$ is a partially saturated, fully saturated or fully unsaturated three to six membered ring optionally having one to two heteroatoms selected independently from oxygen, sulfur and nitrogen;

wherein said $V_{I-1}$ substituent is optionally mono-, di-, tri-, or tetra-substituted independently with halo, $(C_1\text{-}C_6)$alkyl, $(C_1\text{-}C_6)$alkoxy, amino, nitro, cyano, $(C_1\text{-}C_6)$alkyloxycarbonyl, mono-N— or di-N,N—$(C_1\text{-}C_6)$alkylamino wherein said $(C_1\text{-}C_6)$alkyl substituent is optionally mono-substituted with oxo, said $(C_1\text{-}C_6)$alkyl substituent is also optionally substituted with from one to nine fluorines;

wherein either $R_{I-3}$ must contain $V_I$ or $R_{I-4}$ must contain $V_{I-1}$; and $R_{I-5}$, $R_{I-6}$, $R_{I-7}$ and $R_{I-8}$ are each independently hydrogen, hydroxy or oxy wherein said oxy is substituted with $T_I$ or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_I$;

wherein $T_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_I$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines.

Compounds of Formula I and their methods of manufacture are disclosed in commonly assigned U.S. Pat. Nos. 6,140,342, 6,362,198, and European Patent publication 987251, all of which are incorporated herein by reference in their entireties for all purposes.

In a preferred embodiment, the CETP inhibitor is selected from one of the following compounds of Formula I:

[2R,4S] 4-[(3,5-dichloro-benzyl)-methoxycarbonyl-amino]-6,7-dimethoxy-2-methyl-3,4-dihydro-2H-quinoline-1-carboxylic acid ethyl ester;

[2R,4S] 4-[(3,5-dinitro-benzyl)-methoxycarbonyl-amino]-6,7-dimethoxy-2-methyl-3,4-dihydro-2H-quinoline-1-carboxylic acid ethyl ester;

[2R,4S] 4-[(2,6-dichloro-pyridin-4-ylmethyl)-methoxycarbonyl-amino]-6,7-dimethoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-6-methoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-7-methoxy-2-methyl-3,4-dihydro-2H-quinoline-1-carboxylic acid ethyl ester,

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid isopropyl ester;

[2R,4S] 4-[(3,5-bis-trifluoromethyl-benzyl)-ethoxycarbonyl-amino]-6,7-dimethoxy-2-methyl-3,4-dihydro-2H-quinoline-1-carboxylic acid ethyl ester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid 2,2,2-trifluoro-ethylester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid propyl ester;

[2R,4S] 4-[(3,5-bis-trifluoromethyl-benzyl)-methoxycarbonyl-amino]-6,7-dimethoxy-2-methyl-3,4-dihydro-2H-quinoline-1-carboxylic acid tert-butyl ester;

[2R,4S] 4-[(3,5-bis-trifluoromethyl-benzyl)-methoxycarbonyl-amino]-2-methyl-6-trifluoromethoxy-3,4-dihydro-2H-quinoline-1-carboxylic acid ethyl ester,

[2R,4S] (3,5-bis-trifluoromethyl-benzyl)-(1-butyryl-6,7-dimethoxy-2-methyl-1,2,3,4-tetrahydro-quinolin-4-yl)-carbamic acid methyl ester;

[2R,4S] (3,5-bis-trifluoromethyl-benzyl)-(1-butyl-6,7-dimethoxy-2-methyl-1,2,3,4-tetrahydro-quinolin-4-yl)-carbamic acid methyl ester; and

[2R,4S] (3,5-bis-trifluoromethyl-benzyl)-[1-(2-ethyl-butyl)-6,7-dimethoxy-2-methyl-1,2,3,4-tetrahydro-quinolin-4-yl]-carbamic acid methyl ester, hydrochloride.

Another class of CETP inhibitors that finds utility with the present invention consists of 4-carboxyamino-2-methyl-1,2,3,4,-tetrahydroquinolines, having the Formula II

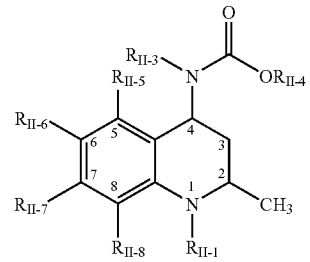

Formula II and pharmaceutically acceptable salts, enantiomers, or stereoisomers of said compounds;

wherein $R_{II-1}$ is hydrogen, $Y_{II}$, $W_{II}$—$X_{II}$, $W_{II}$—$Y_{II}$;

wherein $W_{II}$ is a carbonyl, thiocarbonyl, sulfinyl or sulfonyl;

$X_{II}$ is —O—$Y_{II}$, —S—$Y_{II}$, —N(H)—$Y_{II}$ or —N—$(Y_{II})_2$;

wherein $Y_{II}$ for each occurrence is independently $Z_{II}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{II}$;

$Z_{II}$, is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{II}$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$ alkylthio, amino, nitro, cyano, oxo, carboxy, $(C_1-C_6)$ alkyloxycarbonyl, mono-N— or di-N,N—$(C_1-C_6)$ alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl is also optionally substituted with from one to nine fluorines;

$R_{II-3}$ is hydrogen or $Q_{II}$;

wherein $Q_{II}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II}$;

wherein $V_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{II}$ substituent is optionally mono-, di-, tri-, or tetra-substituted independently with halo, $(C_1-C_6)$ alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$alkylcarboxamoyl, carboxy, $(C_1-C_6)$alkyloxycarbonyl, mono-N— or di-N,N—$(C_1-C_6)$alkylamino wherein said $(C_1-C_6)$ alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino or said $(C_1-C_6)$alkyl or $(C_2-C_6)$alkenyl substituents are optionally substituted with from one to nine fluorines;

$R_{II-4}$ is $Q_{II-1}$ or $V_{II-1}$ wherein $Q_{II-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II-1}$;

wherein $V_{II-1}$ is a partially saturated, fully saturated or fully unsaturated three to six membered ring optionally having one to two heteroatoms selected independently from oxygen, sulfur and nitrogen;

wherein said $V_{II-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$ alkyloxycarbonyl, mono-N— or di-N,N—$(C_1-C_6)$ alkylamino wherein said $(C_1-C_6)$alkyl substituent is optionally mono-substituted with oxo, said $(C_1-C_6)$ alkyl substituent is optionally substituted with from one to nine fluorines;

wherein either $R_{II-3}$ must contain $V_{II}$ or $R_{II-4}$ must contain $V_{II-1}$; and $R_{II-5}$, $R_{II-6}$, $R_{II-7}$ and $R_{II-8}$ are each independently hydrogen, a bond, nitro or halo wherein said bond is substituted with $T_{II}$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{II}$;

wherein $T_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{II}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$ alkylthio, amino, nitro, cyano, oxo, carboxy, $(C_1-C_6)$ alkyloxycarbonyl, mono-N— or di-N,N—$(C_1-C_6)$ alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; provided that at least one of substituents $R_{II-5}$, $R_{II-6}$, $R_{II-7}$ and $R_{II-8}$ is not hydrogen and is not linked to the quinoline moiety through oxy.

Compounds of Formula II and their methods of manufacture are disclosed in commonly assigned U.S. Pat. No. 6,147,090, U.S. patent application Ser. No. 09/671,400 filed Sep. 27, 2000, and PCT Publication No. WO00/17166, all of which are incorporated herein by reference in their entireties for all purposes.

In a preferred embodiment, the CETP inhibitor is selected from one of the following compounds of Formula II:

[2R,4S] 4-[(3,5-Bis-trifluoromethyl-benzyl)-methoxycarbonyl-amino]-2-methyl-7-trifluoromethyl-3,4-dihydro-2H-quinoline-1-carboxylic acid ethyl ester;

[2R,4S] 4-[(3,5-Bis-trifluoromethyl-benzyl)-methoxycarbonyl-amino]-7-chloro-2-methyl-3,4-dihydro-2H-quinoline-1-carboxylic acid ethyl ester;

[2R,4S] 4-[(3,5-Bis-trifluoromethyl-benzyl)-methoxycarbonyl-amino]-6-chloro-2-methyl-3,4-dihydro-2H-quinoline-1-carboxylic acid ethyl ester;

[2R,4S] 4-[(3,5-Bis-trifluoromethyl-benzyl)-methoxycarbonyl-amino]-2,6,7-trimethyl-3,4-dihydro-2H-quinoline-1-carboxylic acid ethyl ester;

[2R,4S] 4-[(3,5-Bis-trifluoromethyl-benzyl)-methoxycarbonyl-amino]-6,7-diethyl-2-methyl-3,4-dihydro-2H-quinoline-1-carboxylic acid ethyl ester;
[2R,4S] 4-[(3,5-Bis-trifluoromethyl-benzyl)-methoxycarbonyl-amino]-6-ethyl-2-methyl-3,4-dihydro-2H-quinoline-1-carboxylic acid ethyl ester;
[2R,4S] 4-[(3,5-Bis-trifluoromethyl-benzyl)-methoxycarbonyl-amino]-2-methyl-6-trifluoromethyl-3,4-dihydro-2H-quinoline-1-carboxylic acid ethyl ester; and
[2R,4S] 4-[(3,5-bis-trifluoromethyl-benzyl)-methoxycarbonyl-amino]-2-methyl-6-trifluoromethyl-3,4-dihydro-2H-quinoline-1-carboxylic acid isopropyl ester.

Another class of CETP inhibitors that finds utility with the present invention consists of annulated 4-carboxyamino-2-methyl-1,2,3,4,-tetrahydroquinolines, having the Formula III

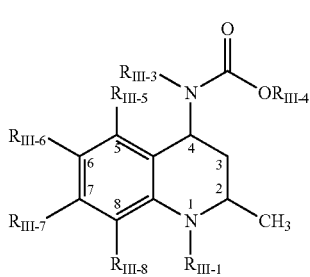

Formula III and pharmaceutically acceptable salts, enantiomers, or stereoisomers of said compounds;
wherein $R_{III-1}$ is hydrogen, $Y_{III}$, $W_{III}$—$X_{III}$, $W_{III}$—$Y_{III}$;
wherein $W_{III}$ is a carbonyl, thiocarbonyl, sulfinyl or sulfonyl;
$X_{III}$ is —O—$Y_{III}$, —S—$Y_{III}$, —N(H)—$Y_{III}$ or —N—$(Y_{III})_2$;
$Y_{III}$ for each occurrence is independently $Z_{III}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{III}$;
wherein $Z_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;
wherein said $Z_{III}$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl optionally substituted with from one to nine fluorines;
$R_{III-3}$ is hydrogen or $Q_{III}$;
wherein $Q_{III}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III}$;
wherein $V_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;
wherein said $V_{III}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino or said $(C_1-C_6)$alkyl or $(C_2-C_6)$alkenyl are optionally substituted with from one to nine fluorines;
$R_{III-4}$ is $Q_{III-1}$ or $V_{III-1}$;
wherein $Q_{III-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III-1}$;
wherein $V_{III-1}$ is a partially saturated, fully saturated or fully unsaturated three to six membered ring optionally having one to two heteroatoms selected independently from oxygen, sulfur and nitrogen;
wherein said $V_{III-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$ alkyl substituent optionally having from one to nine fluorines;

wherein either $R_{III-3}$ must contain $V_{III}$ or $R_{III-4}$ must contain $V_{III-1}$; and $R_{III-5}$ and $R_{III-6}$, or $R_{III-6}$ and $R_{III-7}$, and/or $R_{III-7}$ and $R_{III-8}$ are taken together and form at least one four to eight membered ring that is partially saturated or fully unsaturated optionally having one to three heteroatoms independently selected from nitrogen, sulfur and oxygen;

wherein said ring or rings formed by $R_{III-5}$ and $R_{III-6}$, or $R_{III-6}$ and $R_{III-7}$, and/or $R_{III-7}$ and $R_{III-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent optionally having from one to nine fluorines;

provided that the $R_{III-5}$, $R_{III-6}$, $R_{III-7}$ and/or $R_{III-8}$, as the case may be, that do not form at least one ring are each independently hydrogen, halo, $(C_1-C_6)$alkoxy or $(C_1-C_6)$alkyl, said $(C_1-C_6)$alkyl optionally having from one to nine fluorines.

Compounds of Formula III and their methods of manufacture are disclosed in commonly assigned U.S. Pat. Nos. 6,147,089, 6,310,075, and European Patent Application No. 99307240.4 filed Sep. 14, 1999, all of which are incorporated herein by reference in their entireties for all purposes.

In a preferred embodiment, the CETP inhibitor is selected from one of the following compounds of Formula III:

[2R,4S] 4-[(3,5-bis-trifluoromethyl-benzyl)-methoxycarbonyl-amino]-2-methyl-2,3,4,6,7,8-hexahydro-cyclopenta[g]quinoline-1-carboxylic acid ethyl ester;

[6R,8S] 8-[(3,5-bis-trifluoromethyl-benzyl)-methoxycarbonyl-amino]-6-methyl-3,6,7,8-tetrahydro-1H-2-thia-5-aza-cyclopenta[b]naphthalene-5-carboxylic acid ethyl ester;

[6R,8S] 8-[(3,5-bis-trifluoromethyl-benzyl)-methoxycarbonyl-amino]-6-methyl-3,6,7,8-tetrahydro-2H-furo[2,3-g]quinoline-5-carboxylic acid ethyl ester;

[2R,4S] 4-[(3,5-bis-trifluoromethyl-benzyl)-methoxycarbonyl-amino]-2-methyl-3,4,6,8-tetrahydro-2H-furo[3,4-g]quinoline-1-carboxylic acid ethyl ester;

[2R,4S] 4-[(3,5-bis-trifluoromethyl-benzyl)-methoxycarbonyl-amino]-2-methyl-3,4,6,7,8,9-hexahydro-2H-benzo[g]quinoline-1-carboxylic acid propyl ester;

[7R,9S] 9-[(3,5-bis-trifluoromethyl-benzyl)-methoxycarbonyl-amino]-7-methyl-1,2,3,7,8,9-hexahydro-6-aza-cyclopenta[a]naphthalene-6-carboxylic acid ethyl ester; and

[6S,8R] 6-[(3,5-bis-trifluoromethyl-benzyl)-methoxycarbonyl-amino]-8-methyl-1,2,3,6,7,8-hexahydro-9-aza-cyclopenta[a]naphthalene-9-carboxylic acid ethyl ester.

Another class of CETP inhibitors that finds utility with the present invention consists of 4-carboxyamino-2-substituted-1,2,3,4,-tetrahydroquinolines, having the Formula IV

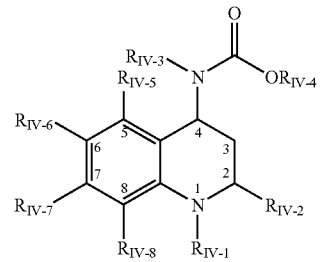

Formula IV and pharmaceutically acceptable salts, enantiomers, or stereoisomers of said compounds;

wherein $R_{IV-1}$ is hydrogen, $Y_{IV}$, $W_{IV}$—$X_{IV}$ or $W_{IV}$—$Y_{IV}$;

wherein $W_{IV}$ is a carbonyl, thiocarbonyl, sulfinyl or sulfonyl;

$X_{IV}$ is —O—$Y_{IV}$, —S—$Y_{IV}$, —N(H)—$Y_{IV}$ or —N—$(Y_{IV})_2$;

wherein $Y_{IV}$ for each occurrence is independently $Z_{IV}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{IV}$;

wherein $Z_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{IV}$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{IV-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{IV-2}$ is a partially saturated, fully saturated or fully unsaturated three to seven membered ring optionally having one to two heteroatoms selected independently from oxygen, sulfur and nitrogen, wherein said $R_{IV-2}$ ring is optionally attached through $(C_1-C_4)$alkyl;

wherein said $R_{IV-2}$ ring is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, oxo or $(C_1-C_6)$alkyloxycarbonyl;

with the proviso that $R_{IV-2}$ is not methyl;

$R_{IV-3}$ is hydrogen or $Q_{IV}$;

wherein $Q_{IV}$ is a fully saturated, partially unsaturated or fully unsaturated one to six membered straight or branched carbon chain wherein the carbons other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV}$;

wherein $V_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{IV}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$alkenyl substituents are also optionally substituted with from one to nine fluorines;

$R_{IV-4}$ is $Q_{IV-1}$ or $V_{IV-1}$;

wherein $Q_{IV-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV-1}$;

wherein $V_{IV-1}$ is a partially saturated, fully saturated or fully unsaturated three to six membered ring optionally having one to two heteroatoms selected independently from oxygen, sulfur and nitrogen;

wherein said $V_{IV-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{IV-3}$ must contain $V_{IV}$ or $R_{IV-4}$ must contain $V_{IV-1}$;

$R_{IV-5}$, $R_{IV-6}$, $R_{IV-7}$ and $R_{IV-8}$ are each independently hydrogen, a bond, nitro or halo wherein said bond is substituted with $T_{IV}$ or a partially saturated, fully saturated or fully unsaturated $(C_1-C_{12})$ straight or branched carbon chain wherein carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{IV}$;

wherein $T_{IV}$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{IV}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; and wherein $R_{IV-5}$ and $R_{IV-6}$, or $R_{IV-6}$ and $R_{IV-7}$, and/or $R_{IV-7}$ and $R_{IV-8}$ may also be taken together and can form at least one four to eight membered ring that is partially saturated or fully unsaturated optionally having one to three heteroatoms independently selected from nitrogen, sulfur and oxygen;

wherein said ring or rings formed by $R_{IV-5}$ and $R_{IV-6}$, or $R_{IV-6}$ and $R_{IV-7}$, and/or $R_{IV-7}$ and $R_{IV-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—($C_1$-$C_6$)alkylamino, said ($C_1$-$C_6$)alkyl substituent is also optionally substituted with from one to nine fluorines;

with the proviso that when $R_{IV-2}$ is carboxyl or ($C_1$-$C_4$) alkylcarboxyl, then $R_{IV-1}$ is not hydrogen.

Compounds of Formula IV and their methods of manufacture are disclosed in commonly assigned U.S. Pat. No. 6,197,786, U.S. application Ser. No. 09/685,3000 filed Oct. 10, 2000, and PCT Publication No. WO 00/17164, all of which are incorporated herein by reference in their entireties for all purposes.

In a preferred embodiment, the CETP inhibitor is selected from one of the following compounds of Formula IV:

[2S,4S] 4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S] 2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2R,4R]-4-[(3,5-bis-trifluoromethyl-benzyl)-methoxycarbonyl-amino]-2-cyclopropyl-6-trifluoromethyl-3,4-dihydro-2H-quinaline-1-carboxylic acid isopropyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid propyl ester.

Another class of CETP inhibitors that finds utility with the present invention consists of 4-amino substituted-2-substituted-1,2,3,4,-tetrahydroquinolines, having the Formula V

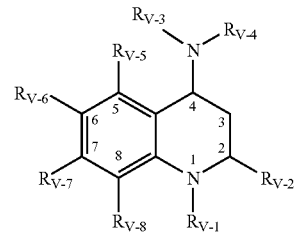

Formula V and pharmaceutically acceptable salts, enantiomers, or stereoisomers of said compounds;

wherein $R_{V-1}$ is $Y_V$, $W_V$—$X_V$ or $W_V$—$Y_V$;

wherein $W_V$ is a carbonyl, thiocarbonyl, sulfinyl or sulfonyl;

$X_V$ is —O—$Y_V$, —S—$Y_V$, —N(H)—$Y_V$ or —N—($Y_V$)$_2$;

wherein $Y_V$ for each occurrence is independently $Z_V$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_V$;

wherein $Z_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_V$ substituent is optionally mono-, di- or tri-substituted independently with halo, ($C_2$-$C_6$)alkenyl, ($C_1$-$C_6$)alkyl, hydroxy, ($C_1$-$C_6$)alkoxy, ($C_1$-$C_4$) alkylthio, amino, nitro, cyano, oxo, carboxy, ($C_1$-$C_6$) alkyloxycarbonyl, mono-N— or di-N,N—($C_1$-$C_6$) alkylamino wherein said ($C_1$-$C_6$)alkyl substituent is optionally mono-, di- or tri-substituted independently with halo, hydroxy, ($C_1$-$C_6$)alkoxy, ($C_1$-$C_4$)alkylthio, amino, nitro, cyano, oxo, carboxy, ($C_1$-$C_6$)alkyloxycarbonyl, mono-N— or di-N,N—($C_1$-$C_6$)alkylamino, said ($C_1$-$C_6$)alkyl substituent is also optionally substituted with from one to nine fluorines;

$R_{V-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{V-2}$ is a partially saturated, fully saturated or fully unsaturated three to seven membered ring optionally having one to two heteroatoms selected independently from oxygen, sulfur and nitrogen, wherein said $R_{V-2}$ ring is optionally attached through $(C_1-C_4)$alkyl;

wherein said $R_{V-2}$ ring is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, oxo or $(C_1-C_6)$alkyloxycarbonyl;

$R_{V-3}$ is hydrogen or $Q_V$;

wherein $Q_V$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_V$;

wherein $V_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_V$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$alkenyl substituents are also optionally substituted with from one to nine fluorines;

$R_{V-4}$ is cyano, formyl, $W_{V-1}Q_{V-1}$, $W_{V-1}V_{V-1}$, $(C_1-C_4)$alkylene$V_{V-1}$ or $V_{V-2}$;

wherein $W_{V-1}$ is carbonyl, thiocarbonyl, SO or $SO_2$, wherein $Q_{V-1}$ a fully saturated, partially unsaturated or fully unsaturated one to six membered straight or branched carbon chain wherein the carbons may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{V-1}$;

wherein $V_{V-1}$ is a partially saturated, fully saturated or fully unsaturated three to six membered ring optionally having one to two heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{V-1}$ substituent is optionally mono-, di-, tri-, or tetra-substituted independently with halo, $(C_1-C_6)$alkyl, $(C_1-C_6)$alkoxy, hydroxy, oxo, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein $V_{V-2}$ is a partially saturated, fully saturated or fully unsaturated five to seven membered ring containing one to four heteroatoms selected independently from oxygen, sulfur and nitrogen;

wherein said $V_{V-2}$ substituent is optionally mono-, di- or tri-substituted independently with halo, $(C_1-C_2)$alkyl, $(C_1-C_2)$alkoxy, hydroxy, or oxo wherein said $(C_1-C_2)$ alkyl optionally has from one to five fluorines; and wherein $R_{V-4}$ does not include oxycarbonyl linked directly to the $C^4$ nitrogen;

wherein either $R_{V-3}$ must contain $V_V$ or $R_{V-4}$ must contain $V_{V-1}$;

$R_{V-5}$, $R_{V-6}$, $R_{V-7}$ and $R_{V-8}$ are independently hydrogen, a bond, nitro or halo wherein said bond is substituted with $T_V$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen, wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_V$;

wherein $T_V$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_V$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent also optionally has from one to nine fluorines;

wherein $R_{V-5}$ and $R_{V-6}$, or $R_{V-6}$ and $R_{V-7}$, and/or $R_{V-7}$ and $R_{V-8}$ may also be taken together and can form at least one ring that is a partially saturated or fully unsaturated four to eight membered ring optionally having one to three heteroatoms independently selected from nitrogen, sulfur and oxygen;

wherein said rings formed by $R_{V-5}$ and $R_{V-6}$, or $R_{V-6}$ and $R_{V-7}$, and/or $R_{V-7}$ and $R_{V-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent also optionally has from one to nine fluorines.

Compounds of Formula V and their methods of manufacture are disclosed in commonly assigned U.S. Pat. No. 6,140,343, U.S. patent application Ser. No. 09/671,221 filed Sep. 27, 2000, and PCT Publication No. WO 00/17165, all of which are incorporated herein by reference in their entireties for all purposes.

In a preferred embodiment, the CETP inhibitor is selected from one of the following compounds of Formula V:

[2S,4S] 4-[(3,5-bis-trifluoromethyl-benzyl)-formyl-amino]-2-cyclopropyl-6-trifluoromethyl-3,4-dihydro-2H-quinoline-1-carboxylic acid isopropyl ester;

[2S,4S] 4-[(3,5-bis-trifluoromethyl-benzyl)-formyl-amino]-2-cyclopropyl-6-trifluoromethyl-3,4-dihydro-2H-quinoline-1-carboxylic acid propyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid tert-butyl ester;

[2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester;

[2R,4S] 4-[acetyl-(3,5-bis-trifluoromethyl-benzyl)-amino]-2-methyl-6-trifluoromethyl-3,4-dihydro-2H-quinoline-1-carboxylic acid ethyl ester;

[2S,4S] 4-[1-(3,5-bis-trifluoromethyl-benzyl)-ureido]-2-cyclopropyl-6-trifluoromethyl-3,4-dihydro-2H-quinoline-1-carboxylic acid isopropyl ester;

[2R,4S] 4-[acetyl-(3,5-bis-trifluoromethyl-benzyl)-amino]-2-ethyl-6-trifluoromethyl-3,4-dihydro-2H-quinoline-1-carboxylic acid ethyl ester;

[2S,4S] 4-[acetyl-(3,5-bis-trifluoromethyl-benzyl)-amino]-2-methoxymethyl-6-trifluoromethyl-3,4-dihydro-2H-quinoline-1-carboxylic acid isopropyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid propyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-formyl-amino]-2-ethyl-6-trifluoromethyl-3,4-dihydro-2H-quinoline-1-carboxylic acid isopropyl ester;

[2R,4S] 4-[(3,5-bis-trifluoromethyl-benzyl)-formyl-amino]-2-methyl-6-trifluoromethyl-3,4-dihydro-2H-quinoline-1-carboxylic acid ethyl ester;

[2S,4S] 4-[acetyl-(3,5-bis-trifluoromethyl-benzyl)-amino]-2-cyclopropyl-6-trifluoromethyl-3,4-dihydro-2H-quinoline-1-carboxylic acid isopropyl ester;

[2R,4S] 4-[(3,5-bis-trifluoromethyl-benzyl)-formyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-formyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-formyl-amino]-2-methyl-6-trifluoromethyl-3,4-dihydro-2H-quinoline-1-carboxylic acid isopropyl ester; and

[2R,4S] 4-[acetyl-(3,5-bis-trifluoromethyl-benzyl)-amino]-2-methyl-6-trifluoromethyl-3,4-dihydro-2H-quinoline-1-carboxylic acid isopropyl ester.

Another class of CETP inhibitors that finds utility with the present invention consists of cycloalkano-pyridines having the Formula VI

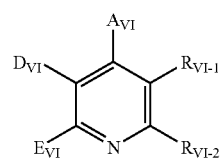

Formula VI and pharmaceutically acceptable salts, enantiomers, or stereoisomers of said compounds;

in which $A_{VI}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —BN-$R_{VI-3}R_{VI-4}$, wherein $R_{VI-3}$ and $R_{VI-4}$ are identical or different and denote a hydrogen, phenyl or a straight-chain or branched alkyl containing up to 6 carbon atoms, $D_{VI}$ denotes an aryl containing 6 to 10 carbon atoms, which is optionally substituted with a phenyl, nitro, halogen, trifluoromethyl or trifluoromethoxy, or a radical according to the formula $R_{VI-5}$-$L_{VI}$-,

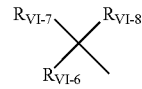

or $R_{VI-9}$-$T_{VI}$-$V_{VI}$—$X_{VI}$, wherein $R_{VI-5}$, $R_{VI-6}$ and $R_{VI-9}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteroatoms from the series of S, N and/or O, and/or in the form of a group according to the formula BOR$_{VI\text{-}10}$, —SR$_{VI\text{-}11}$, —SO$_2$R$_{VI\text{-}12}$ or BNR$_{VI\text{-}13}$R$_{VI\text{-}14}$, wherein R$_{VI\text{-}10}$, R$_{VI\text{-}11}$ and R$_{VI\text{-}12}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, R$_{VI\text{-}13}$ and R$_{VI\text{-}14}$ are identical or different and have the meaning of R$_{VI\text{-}3}$ and R$_{VI\text{-}4}$ given above, or R$_{VI\text{-}5}$ and/or R$_{VI\text{-}6}$ denote a radical according to the formula

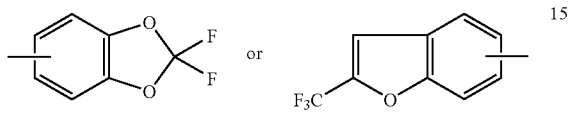

R$_{VI\text{-}7}$ denotes a hydrogen or halogen, and

R$_{VI\text{-}8}$ denotes a hydrogen, halogen, azido, trifluoromethyl, hydroxyl, trifluoromethoxy, a straight-chain or branched alkoxy or alkyl containing up to 6 carbon atoms each, or a radical according to the formula —NR$_{VI\text{-}15}$R$_{VI\text{-}16}$, wherein R$_{VI\text{-}15}$ and R$_{VI\text{-}16}$ are identical or different and have the meaning of R$_{VI\text{-}3}$ and R$_{VI\text{-}4}$ given above, or R$_{VI\text{-}7}$ and R$_{VI\text{-}8}$ together form a radical according to the formula =O or =NR$_{VI\text{-}17}$, wherein R$_{VI\text{-}17}$ denotes a hydrogen or a straight-chain or branched alkyl, alkoxy or acyl containing up to 6 carbon atoms each, L$_{VI}$ denotes a straight-chain or branched alkylene or alkenylene chain containing up to 8 carbon atoms each, which are optionally substituted with up to two hydroxyl groups, T$_{VI}$ and X$_{VI}$ are identical or different and denote a straight-chain or branched alkylene chain containing up to 8 carbon atoms, or T$_{VI}$ or X$_{VI}$ denotes a bond, V$_{VI}$ denotes an oxygen or sulfur atom or an BNR$_{VI\text{-}18}$ group, wherein R$_{VI\text{-}18}$ denotes a hydrogen or a straight-chain or branched alkyl containing up to 6 carbon atoms or a phenyl, E$_{VI}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl, R$_{VI\text{-}1}$ and R$_{VI\text{-}2}$ together form a straight-chain or branched alkylene chain containing up to 7 carbon atoms, which must be substituted with a carbonyl group and/or a radical according to the formula

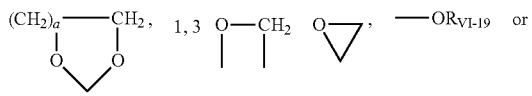

-continued

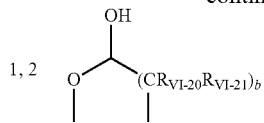

wherein a and b are identical or different and denote a number equaling 1, 2 or 3, R$_{VI\text{-}19}$ denotes a hydrogen atom, a cycloalkyl containing 3 to 7 carbon atoms, a straight-chain or branched silylalkyl containing up to 8 carbon atoms, or a straight-chain or branched alkyl containing up to 8 carbon atoms, which is optionally substituted with a hydroxyl, a straight-chain or a branched alkoxy containing up to 6 carbon atoms or a phenyl, which may in turn be substituted with a halogen, nitro, trifluoromethyl, trifluoromethoxy or phenyl or tetrazole-substituted phenyl, and an alkyl that is optionally substituted with a group according to the formula BOR$_{VI\text{-}22}$, wherein R$_{VI\text{-}22}$ denotes a straight-chain or branched acyl containing up to 4 carbon atoms or benzyl, or R$_{VI\text{-}19}$ denotes a straight-chain or branched acyl containing up to 20 carbon atoms or benzoyl, which is optionally substituted with a halogen, trifluoromethyl, nitro or trifluoromethoxy, or a straight-chain or branched fluoroacyl containing up to 8 carbon atoms, R$_{VI\text{-}20}$ and R$_{VI\text{-}21}$ are identical or different and denote a hydrogen, phenyl or a straight-chain or branched alkyl containing up to 6 carbon atoms, or R$_{VI\text{-}20}$ and R$_{VI\text{-}21}$ together form a 3- to 6-membered carbocyclic ring, and a the carbocyclic rings formed are optionally substituted, optionally also geminally, with up to six identical or different substituents in the form of trifluoromethyl, hydroxyl, nitrile, halogen, carboxyl, nitro, azido, cyano, cycloalkyl or cycloalkyloxy containing 3 to 7 carbon atoms each, a straight-chain or branched alkoxycarbonyl, alkoxy or alkylthio containing up to 6 carbon atoms each, or a straight-chain or branched alkyl containing up to 6 carbon atoms, which is in turn substituted with up to two identical or different substituents in the form of a hydroxyl, benzyloxy, trifluoromethyl, benzoyl, a straight-chain or branched alkoxy, oxyacyl or carboxyl containing up to 4 carbon atoms each and/or a phenyl, which may in turn be substituted with a halogen, trifluoromethyl or trifluoromethoxy, and/or the carbocyclic rings formed are optionally substituted, also geminally, with up to five identical or different substituents in the form of a phenyl, benzoyl, thiophenyl or sulfonylbenzyl, which in turn are optionally substituted with a halogen, trifluoromethyl, trifluoromethoxy or nitro, and/or optionally in the form of a radical according to the formula

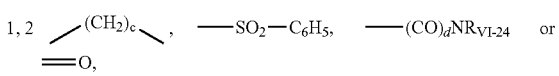

wherein c is a number equaling 1, 2, 3 or 4, d is a number equaling 0 or 1, $R_{VI-23}$ and $R_{VI-24}$ are identical or different and denote a hydrogen, cycloalkyl containing 3 to 6 carbon atoms, a straight-chain or branched alkyl containing up to 6 carbon atoms, benzyl or phenyl, which is optionally substituted with up to two identical or different substituents in the form of halogen, trifluoromethyl, cyano, phenyl or nitro, and/or the carbocyclic rings formed are optionally substituted with a spiro-linked radical according to the formula

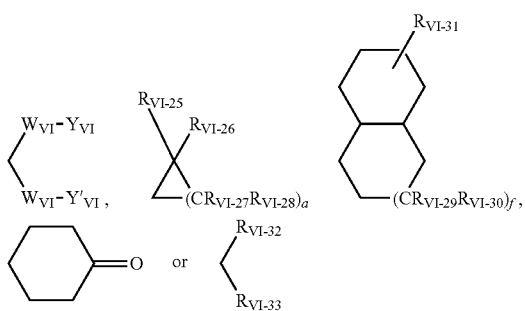

wherein
  $W_{VI}$ denotes either an oxygen atom or a sulfur atom,
  $Y_{VI}$ and $Y{=}_{VI}$ together form a 2- to 6-membered straight-chain or branched alkylene chain,
  e is a number equaling 1, 2, 3, 4, 5, 6 or 7,
  f is a number equaling 1 or 2,
  $R_{VI-25}$, $R_{VI-26}$, $R_{VI-27}$, $R_{VI-28}$, $R_{VI-29}$, $R_{VI-30}$ and $R_{VI-31}$ are identical or different and denote a hydrogen, trifluoromethyl, phenyl, halogen or a straight-chain or branched alkyl or alkoxy containing up to 6 carbon atoms each, or
  $R_{VI-25}$ and $R_{VI-26}$ or $R_{VI-27}$ and $R_{VI-28}$ each together denote a straight-chain or branched alkyl chain containing up to 6 carbon atoms or
  $R_{VI-25}$ and $R_{VI-26}$ or $R_{VI-27}$ and $R_{VI-28}$ each together form a radical according to the formula

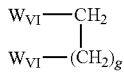

wherein
  $W_{VI}$ has the meaning given above,
  g is a number equaling 1, 2, 3, 4, 5, 6 or 7,
  $R_{VI-32}$ and $R_{VI-33}$ together form a 3- to 7-membered heterocycle, which contains an oxygen or sulfur atom or a group according to the formula SO, $SO_2$ or $BNR_{VI-34}$, wherein
  $R_{VI-34}$ denotes a hydrogen atom, a phenyl, benzyl, or a straight-chain or branched alkyl containing up to 4 carbon atoms, and salts and N oxides thereof, with the exception of 5(6H)-quinolones, 3-benzoyl-7,8-dihydro-2,7,7-trimethyl-4-phenyl.

Compounds of Formula VI and their methods of manufacture are disclosed in European Patent Application No. EP 818448 A1, U.S. Pat. Nos. 6,207,671 and 6,069,148, all of which are incorporated herein by reference in their entireties for all purposes.

In a preferred embodiment, the CETP inhibitor is selected from one of the following compounds of Formula VI:
2-cyclopentyl-4-(4-fluorophenyl)-7,7-dimethyl-3-(4-trifluoromethylbenzoyl)-4,6,7,8-tetrahydro-1H-quinolin-5-one;
2-cyclopentyl-4-(4-fluorophenyl)-7,7-dimethyl-3-(4-trifluoromethylbenzoyl)-7,8-dihydro-6H-quinolin-5-one;
[2-cyclopentyl-4-(4-fluorophenyl)-5-hydroxy-7,7-dimethyl-5,6,7,8-tetrahydroquinolin-3-yl]-(4-trifluoromethylphenyl)-methanone;
[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanone;
[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanol;
5-(t-butyldimethylsilanyloxy)-2-cyclopentyl-4-(4-fluorophenyl)-3-[fluoro-(4-trifluoromethylphenyl)-methyl]-7,7-dimethyl-5,6,7,8-tetrahydroquinoline; and
2-cyclopentyl-4-(4-fluorophenyl)-3-[fluoro-(4-trifluoromethylphenyl)-methyl]-7,7-dimethyl-5,6,7,8-tetrahydroquinolin-5-ol.

Another class of CETP inhibitors that finds utility with the present invention consists of substituted-pyridines having the Formula VII Formula VII

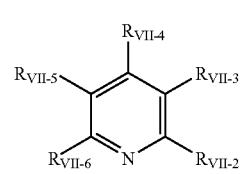

or a pharmaceutically acceptable salt or tautomer thereof,
  wherein
    $R_{VII-2}$ and $R_{VII-6}$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_{VII-2}$ and $R_{VII-6}$ is fluorinated alkyl, chlorofluorinated alkyl or alkoxyalkyl;
    $R_{VII-3}$ is selected from the group consisting of hydroxy, amido, arylcarbonyl, heteroarylcarbonyl, hydroxymethyl
    —CHO,
    —$CO_2R_{VII-7}$, wherein $R_{VII-7}$ is selected from the group consisting of hydrogen, alkyl and cyanoalkyl; and

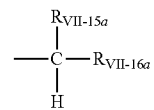

wherein $R_{VII-15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and $R_{VII-16a}$ is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

$R_{VII-4}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, hetereoarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclythioalkenyl, alkylamino, alkenylamino, alkynylamino, arylamino, heteroarylamino, heterocyclylamino, aryldialkylamino, diarylamino, diheteroarylamino, alkylarylamino, alkylheteroarylamino, arylheteroarylamino, trialkylsilyl, trialkenylsilyl, triarylsilyl, —CO(O)N($R_{VII-8a}R_{VII-8b}$), wherein $R_{VII-8a}$ and $R_{VII-8b}$ are independently selected from the group consisting of alkyl, alkenyl, alkynyl, aryl, heteroaryl and heterocyclyl, —$SO_2R_{VII-9}$, wherein $R_{VII-9}$ is selected from the group consisting of hydroxy, alkyl, alkenyl, alkynyl, aryl, heteroaryl and heterocyclyl, —OP(O)($OR_{VII-10a}$) ($OR_{VII-10b}$), wherein $R_{VII-10a}$ and $R_{VII-10b}$ are independently selected from the group consisting of hydrogen, hydroxy, alkyl, alkenyl, alkynyl, aryl, heteroaryl and heterocyclyl, and —OP(S) ($OR_{VII-11a}$) ($OR_{VII-11b}$), wherein $R_{VII-11a}$ and $R_{VII-11b}$ are independently selected from the group consisting of alkyl, alkenyl, alkynyl, aryl, heteroaryl and heterocyclyl;

$R_{VII-5}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxylalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl, —$CO_2R_{VII-14}$, wherein $R_{VII-14}$ is selected from the group consisting of alkyl, alkenyl, alkynyl, aryl, heteroaryl and heterocyclyl;

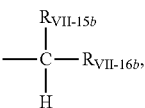

wherein $R_{VII-15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and $R_{VII-16b}$ is selected form the group consisting of alkyl, alkenyl, alkynyl, aryl, heteroaryl, heterocyclyl, arylalkoxy, and trialkylsilyloxy;

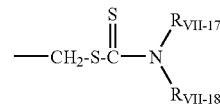

wherein $R_{VII-17}$ and $R_{VII-18}$ are independently selected from the group consisting of alkyl, cycloalkyl, alkenyl, alkynyl, aryl, heteroaryl and heterocyclyl;

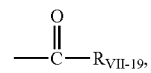

wherein $R_{VII-19}$ is selected from the group consisting of alkyl, cycloalkyl, alkenyl, alkynyl, aryl, heteroaryl, heterocyclyl, —$SR_{VII-20}$, —$OR_{VII-21}$, and $BR_{VII-22}CO_2R_{VII-23}$, wherein $R_{VII-20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, $R_{VII-21}$ is selected from the group consisting of alkyl, alkenyl, alkynyl, aryl, heteroaryl, and heterocyclyl, $R_{VII-22}$ is selected from the group consisting of alkylene or arylene, and $R_{VII-23}$ is selected from the group consisting of alkyl, alkenyl, alkynyl, aryl, heteroaryl, and heterocyclyl;

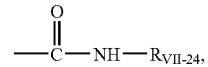

wherein $R_{VII-24}$ is selected from the group consisting of hydrogen, alkyl, cycloalkyl, alkenyl, alkynyl, aryl, heteroaryl, heterocyclyl, aralkyl, aralkenyl, and aralkynyl;

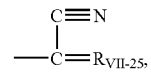

wherein $R_{VII-25}$ is heterocyclylidenyl;

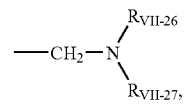

wherein $R_{VII-26}$ and $R_{VII-27}$ are independently selected from the group consisting of hydrogen, alkyl, cycloalkyl, alkenyl, alkynyl, aryl, heteroaryl, and heterocyclyl;

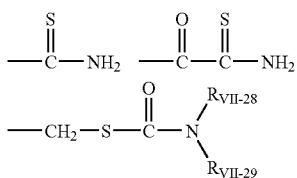

wherein $R_{VII-28}$ and $R_{VII-29}$ are independently selected from the group consisting of hydrogen, alkyl, cycloalkyl, alkenyl, alkynyl, aryl, heteroaryl, and heterocyclyl;

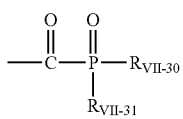

wherein $R_{VII-30}$ and $R_{VII-31}$ are independently alkoxy, alkenoxy, alkynoxy, aryloxy, heteroaryloxy, and heterocyclyloxy; and

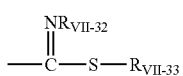

wherein $R_{VII-32}$ and $R_{VII-33}$ are independently selected from the group consisting of hydrogen, alkyl, cycloalkyl, alkenyl, alkynyl, aryl, heteroaryl, and heterocyclyl;

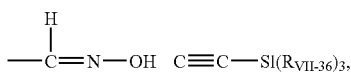

wherein $R_{VII-36}$ is selected from the group consisting of alkyl, alkenyl, aryl, heteroaryl and heterocyclyl;

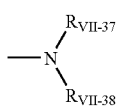

wherein $R_{VII-37}$ and $R_{VII-38}$ are independently selected from the group consisting of hydrogen, alkyl, cycloalkyl, alkenyl, alkynyl, aryl, heteroaryl, and heterocyclyl;

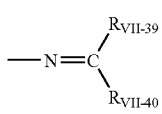

wherein $R_{VII-39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{VII-40}$ is selected from the group consisting of haloalkyl, haloalkenyl, haloalkynyl, haloaryl, halo- heteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

—N═$R_{VII-41}$, wherein $R_{VII-41}$ is heterocyclylidenyl;

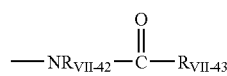

wherein $R_{VII-42}$ is selected from the group consisting of hydrogen, alkyl, alkenyl, alkynyl, aryl, heteroaryl, and heterocyclyl, and $R_{VII-43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

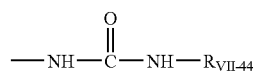

wherein $R_{VII-44}$ is selected from the group consisting of hydrogen, alkyl, cycloalkyl, alkenyl, alkynyl, aryl, heteroaryl and heterocyclyl;

—N═S═O;

—N═C═S;

—N═C═O;

—N$_3$;

—S$R_{VII-45}$ wherein $R_{VII-45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl, —S$R_{VII-46}$, and —CH$_2R_{VII-47}$, wherein $R_{VII-46}$ is selected from the group consisting of alkyl, alkenyl, alkynyl, aryl, heteroaryl and heterocyclyl, and $R_{VII-47}$ is selected from the group consisting of hydrogen, alkyl, alkenyl, alkynyl, aryl, heteroaryl and heterocyclyl; and

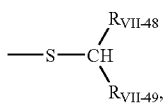

wherein $R_{VII\text{-}48}$ is selected from the group consisting of hydrogen, alkyl, cycloalkyl, alkenyl, alkynyl, aryl, heteroaryl and heterocyclyl, and $R_{VII\text{-}49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

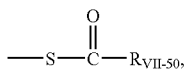

wherein $R_{VII\text{-}50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

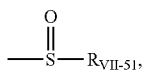

wherein $R_{VII\text{-}51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and

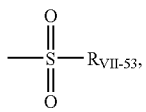

wherein $R_{VII\text{-}53}$ is selected from the group consisting of alkyl, alkenyl, alkynyl, aryl, heteroaryl and heterocyclyl;

provided that when $R_{VII\text{-}5}$ is selected from the group consisting of heterocyclylalkyl and heterocyclylalkenyl, the heterocyclyl radical of the corresponding heterocyclylalkyl or heterocyclylalkenyl is other than δ-lactone; and provided that when $R_{VII\text{-}4}$ is aryl, heteroaryl or heterocyclyl, and one of $R_{VII\text{-}2}$ and $R_{VII\text{-}6}$ is trifluoromethyl, then the other of $R_{VII\text{-}2}$ and $R_{VII\text{-}6}$ is difluoromethyl.

Compounds of Formula VII and their methods of manufacture are disclosed in PCT Publication No. WO 9941237-A1, which is incorporated herein by reference in its entirety for all purposes.

In a preferred embodiment, the CETP inhibitor of Formula VII is dimethyl 5,5-dithiobis[2-difluoromethyl-4-(2-methylpropyl)-6-(trifluoromethyl)-3-pyridine-carboxylate].

Another class of CETP inhibitors that finds utility with the present invention consists of substituted biphenyls having the Formula VIII

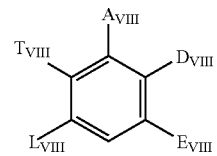

Formula VIII or a pharmaceutically acceptable salt, enantiomers, or stereoisomers thereof,
in which $A_{VIII}$ stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII\text{-}1}R_{VIII\text{-}2}$, wherein $R_{VIII\text{-}1}$ and $R_{VIII\text{-}2}$ are identical or different and denote hydrogen, phenyl, or straight-chain or branched alkyl with up to 6 carbon atoms, $D_{VIII}$ stands for straight-chain or branched alkyl with up to 8 carbon atoms, which is substituted by hydroxy, $E_{VIII}$ and $L_{VIII}$ are either identical or different and stand for straight-chain or branched alkyl with up to 8 carbon atoms, which is optionally substituted by cycloalkyl with 3 to 8 carbon atoms, or stands for cycloalkyl with 3 to 8 carbon atoms, or $E_{VIII}$ has the above-mentioned meaning and $L_{VIII}$ this case stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII\text{-}3}R_{VIII\text{-}4}$, wherein $R_{VIII\text{-}3}$ and $R_{VIII\text{-}4}$ are identical or different and have the meaning given above for $R_{VIII\text{-}1}$ and $R_{VIII\text{-}2}$, or $E_{VIII}$ stands for straight-chain or branched alkyl with up to 8 carbon atoms, or stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII\text{-}5}R_{VIII\text{-}6}$, wherein $R_{VIII\text{-}5}$ and $R_{VIII\text{-}6}$ are identical or different and have the meaning given above for $R_{VIII\text{-}1}$ and $R_{VIII\text{-}2}$, and $L_{VIII}$ in this case stands for straight-chain or branched alkoxy with up to 8 carbon atoms or for cycloalkyloxy with 3 to 8 carbon atoms, $T_{VIII}$ stands for a radical of the formula

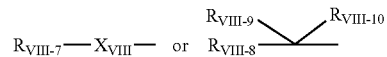

wherein $R_{VIII\text{-}7}$ and $R_{VIII\text{-}8}$ are identical or different and denote cycloalkyl with 3 to 8 carbon atoms, or aryl with 6 to 10 carbon atoms, or denote a 5- to 7-member aromatic, optionally benzo-condensed, heterocyclic compound with up to 3 heteroatoms from the series S, N and/or O, which are optionally substituted up to 3 times in an identical manner or differently by trifluoromethyl, trifluoromethoxy, halogen, hydroxy, carboxyl, by straight-chain or branched alkyl, acyl, alkoxy, or alkoxycarbonyl with up to 6 carbon atoms each, or by phenyl, phenoxy, or thiophenyl, which can in turn be substituted by halogen, trifluoromethyl, or trifluoromethoxy, and/or the rings are substituted by a group of the formula —$NR_{VIII-11}R_{VIII-12}$, wherein $R_{VIII-11}$ and $R_{VIII-12}$ are identical or different and have the meaning given above for $R_{VIII-1}$ and $R_{VIII-2}$, $X_{VIII}$ denotes a straight or branched alkyl chain or alkenyl chain with 2 to 10 carbon atoms each, which are optionally substituted up to 2 times by hydroxy, $R_{VIII-9}$ denotes hydrogen, and $R_{VIII-10}$ denotes hydrogen, halogen, azido, trifluoromethyl, hydroxy, mercapto, trifluoromethoxy, straight-chain or branched alkoxy with up to 5 carbon atoms, or a radical of the formula —$NR_{VIII-13}R_{VIII-14}$, wherein $R_{VIII-13}$ and $R_{VIII-14}$ are identical or different and have the meaning given above for $R_{VIII-1}$ and $R_{VIII-2}$, or $R_{VIII-9}$ and $R_{VIII-10}$ form a carbonyl group together with the carbon atom.

Compounds of Formula VIII are disclosed in PCT Publication No. WO 9804528, which is incorporated herein by reference in its entirety for all purposes.

Another class of CETP inhibitors that finds utility with the present invention consists of substituted 1,2,4-triazoles having the Formula IX

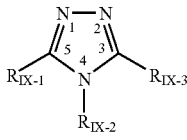

Formula IX or a pharmaceutically acceptable salt or tautomer thereof; wherein $R_{IX-1}$ is selected from higher alkyl, higher alkenyl, higher alkynyl, aryl, aralkyl, aryloxyalkyl, alkoxyalkyl, alkylthioalkyl, arylthioalkyl, and cycloalkylalkyl;

wherein $R_{IX-2}$ is selected from aryl, heteroaryl, cycloalkyl, and cycloalkenyl, wherein $R_{IX-2}$ is optionally substituted at a substitutable position with one or more radicals independently selected from alkyl, haloalkyl, alkylthio, alkylsulfinyl, alkylsulfonyl, alkoxy, halo, aryloxy, aralkyloxy, aryl, aralkyl, aminosulfonyl, amino, monoalkylamino and dialkylamino; and wherein $R_{IX-3}$ is selected from hydrido, —SH and halo; provided $R_{IX-2}$ cannot be phenyl or 4-methylphenyl when $R_{IX-1}$ is higher alkyl and when $R_{IX-3}$ is BSH.

Compounds of Formula IX and their methods of manufacture are disclosed in PCT Publication No. WO 9914204, which is incorporated herein by reference in its entirety for all purposes.

In a preferred embodiment, the CETP inhibitor is selected from the following compounds of Formula IX:

2,4-dihydro-4-(3-methoxyphenyl)-5-tridecyl-3H-1,2,4-triazole-3-thione;
2,4-dihydro-4-(2-fluorophenyl)-5-tridecyl-3H-1,2,4-triazole-3-thione;
2,4-dihydro-4-(2-methylphenyl)-5-tridecyl-3H-1,2,4-triazole-3-thione;
2,4-dihydro-4-(3-chlorophenyl)-5-tridecyl-3H-1,2,4-triazole-3-thione;
2,4-dihydro-4-(2-methoxyphenyl)-5-tridecyl-3H-1,2,4-triazole-3-thione;
2,4-dihydro-4-(3-methylphenyl)-5-tridecyl-3H-1,2,4-triazole-3-thione;
4-cyclohexyl-2,4-dihydro-5-tridecyl-3H-1,2,4-triazole-3-thione;
2,4-dihydro-4-(3-pyridyl)-5-tridecyl-3H-1,2,4-triazole-3-thione;
2,4-dihydro-4-(2-ethoxyphenyl)-5-tridecyl-3H-1,2,4-triazole-3-thione;
2,4-dihydro-4-(2,6-dimethylphenyl)-5-tridecyl-3H-1,2,4-triazole-3-thione;
2,4-dihydro-4-(4-phenoxyphenyl)-5-tridecyl-3H-1,2,4-triazole-3-thione;
4-(1,3-benzodioxol-5-yl)-2,4-dihydro-5-tridecyl-3H-1,2,4-triazole-3-thione;
4-(2-chlorophenyl)-2,4-dihydro-5-tridecyl-3H-1,2,4-triazole-3-thione;
2,4-dihydro-4-(4-methoxyphenyl)-5-tridecyl-3H-1,2,4-triazole-3-thione;
2,4-dihydro-5-tridecyl-4-(3-trifluoromethylphenyl)-3H-1,2,4-triazole-3-thione;
2,4-dihydro-5-tridecyl-4-(3-fluorophenyl)-3H-1,2,4-triazole-3-thione;
4-(3-chloro-4-methylphenyl)-2,4-dihydro-5-tridecyl-3H-1,2,4-triazole-3-thione;
2,4-dihydro-4-(2-methylthiophenyl)-5-tridecyl-3H-1,2,4-triazole-3-thione;
4-(4-benzyloxyphenyl)-2,4-dihydro-5-tridecyl-3H-1,2,4-triazole-3-thione;
2,4-dihydro-4-(2-naphthyl)-5-tridecyl-3H-1,2,4-triazole-3-thione;
2,4-dihydro-5-tridecyl-4-(4-trifluoromethylphenyl)-3H-1,2,4-triazole-3-thione;
2,4-dihydro-4-(1-naphthyl)-5-tridecyl-3H-1,2,4-triazole-3-thione;
2,4-dihydro-4-(3-methylthiophenyl)-5-tridecyl-3H-1,2,4-triazole-3-thione;
2,4-dihydro-4-(4-methylthiophenyl)-5-tridecyl-3H-1,2,4-triazole-3-thione;
2,4-dihydro-4-(3,4-dimethoxyphenyl)-5-tridecyl-3H-1,2,4-triazole-3-thione;
2,4-dihydro-4-(2,5-dimethoxyphenyl)-5-tridecyl-3H-1,2,4-triazole-3-thione;
2,4-dihydro-4-(2-methoxy-5-chlorophenyl)-5-tridecyl-3H-1,2,4-triazole-3-thione;
4-(4-aminosulfonylphenyl)-2,4-dihydro-5-tridecyl-3H-1,2,4-triazole-3-thione;
2,4-dihydro-5-dodecyl-4-(3-methoxyphenyl)-3H-1,2,4-triazole-3-thione;
2,4-dihydro-4-(3-methoxyphenyl)-5-tetradecyl-3H-1,2,4-triazole-3-thione;
2,4-dihydro-4-(3-methoxyphenyl)-5-undecyl-3H-1,2,4-triazole-3-thione; and
2,4-dihydro-(4-methoxyphenyl)-5-pentadecyl-3H-1,2,4-triazole-3-thione.

Another class of CETP inhibitors that finds utility with the present invention consists of hetero-tetrahydroquinolines having the Formula X

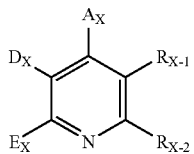

Formula X and pharmaceutically acceptable salts, enantiomers, or stereoisomers or N-oxides of said compounds;
in which
$A_X$ represents cycloalkyl with 3 to 8 carbon atoms or a 5 to 7-membered, saturated, partially saturated or unsaturated, optionally benzo-condensed heterocyclic ring containing up to 3 heteroatoms from the series comprising S, N and/or O, that in case of a saturated heterocyclic ring is bonded to a nitrogen function, optionally bridged over it, and in which the aromatic systems mentioned above are optionally substituted up to 5-times in an identical or different substituents in the form of halogen, nitro, hydroxy, trifluoromethyl, trifluoromethoxy or by a straight-chain or branched alkyl, acyl, hydroxyalkyl or alkoxy each having up to 7 carbon atoms or by a group of the formula $BNR_{X-3}R_{X-4}$,
in which
$R_{X-3}$ and $R_{X-4}$ are identical or different and denote hydrogen, phenyl or straight-chain or branched alkyl having up to 6 carbon atoms,
or
$A_X$ represents a radical of the formula

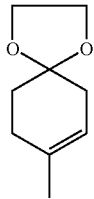

$D_X$ represents an aryl having 6 to 10 carbon atoms, that is optionally substituted by phenyl, nitro, halogen, trifluormethyl or trifluormethoxy, or it represents a radical of the formula

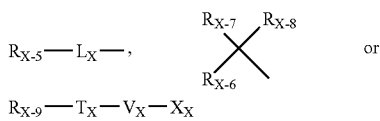

in which
$R_{X-5}$, $R_{X-6}$ and $R_{X-9}$ independently of one another denote cycloalkyl having 3 to 6 carbon atoms, or an aryl having 6 to 10 carbon atoms or a 5- to 7-membered aromatic, optionally benzo-condensed saturated or unsaturated, mono-, bi-, or tricyclic heterocyclic ring from the series consisting of S, N and/or O, in which the rings are substituted, optionally, in case of the nitrogen containing aromatic rings via the N function, with up to 5 identical or different substituents in the form of halogen, trifluoromethyl, nitro, hydroxy, cyano, carbonyl, trifluoromethoxy, straight straight-chain or branched acyl, alkyl, alkylthio, alkylalkoxy, alkoxy, or alkoxycarbonyl each having up to 6 carbon atoms, by aryl or trifluoromethyl-substituted aryl each having 6 to 10 carbon atoms or by an, optionally benzo-condensed, aromatic 5- to 7-membered heterocyclic ring having up to 3 heteroatoms from the series consisting of S, N, and/or O, and/or substituted by a group of the formula $BOR_{X-10}$, $-SR_{X-11}$, $SO_2R_{X-12}$ or $BNR_{X-13}R_{X-14}$ in which
$R_{X-10}$, $R_{X-11}$ and $R_{X-12}$ independently from each other denote aryl having 6 to 10 carbon atoms, which is in turn substituted with up to 2 identical or different substituents in the form of phenyl, halogen or a straight-chain or branched alkyl having up to 6 carbon atoms,
$R_{X-13}$ and $R_{X-14}$ are identical or different and have the meaning of $R_{X-3}$ and $R_{X-4}$ indicated above,
or
$R_{X-5}$ and/or $R_{X-6}$ denote a radical of the formula

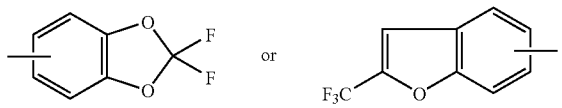

$R_{X-7}$ denotes hydrogen or halogen, and
$R_{X-8}$ denotes hydrogen, halogen, azido, trifluoromethyl, hydroxy, trifluoromethoxy, straight-chain or branched alkoxy or alkyl having up to 6 carbon atoms or a radical of the formula $BNR_{X-15}R_{X-16}$,
in which
$R_{X-15}$ and $R_{X-16}$ are identical or different and have the meaning of $R_{X-3}$ and $R_{X-4}$ indicated above,
or
$R_{X-7}$ and $R_{X-8}$ together form a radical of the formula $=O$ or $=NR_{X-17}$, in which
$R_{X-17}$ denotes hydrogen or straight chain or branched alkyl, alkoxy or acyl having up to 6 carbon atoms,
$L_X$ denotes a straight chain or branched alkylene or alkenylene chain having up to 8 carbon atoms, that are optionally substituted with up to 2 hydroxy groups,
$T_X$ and $X_X$ are identical or different and denote a straight chain or branched alkylene chain with up to 8 carbon atoms
or
$T_X$ or $X_X$ denotes a bond,
$V_X$ represents an oxygen or sulfur atom or an $BNR_{X-18}$-group, in which
$R_{X-18}$ denotes hydrogen or straight chain or branched alkyl with up to 6 carbon atoms or phenyl,
$E_X$ represents cycloalkyl with 3 to 8 carbon atoms, or straight chain or branched alkyl with up to 8 carbon atoms, that is optionally substituted by cycloalkyl with 3 to 8 carbon atoms or hydroxy, or represents a phenyl, that is optionally substituted by halogen or trifluoromethyl,
$R_{X-1}$ and $R_{X-2}$ together form a straight-chain or branched alkylene chain with up to 7 carbon atoms, that must be substituted by carbonyl group and/or by a radical with the formula

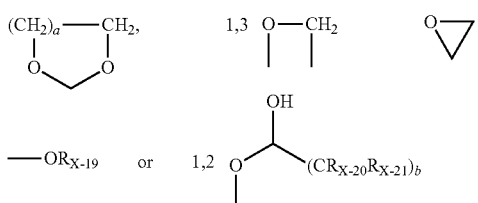

in which a and b are identical or different and denote a number equaling 1, 2, or 3, $R_{X-19}$ denotes hydrogen, cycloalkyl with 3 up to 7 carbon atoms, straight chain or branched silylalkyl with up to 8 carbon atoms or straight chain or branched alkyl with up to 8 carbon atoms, that are optionally substituted by hydroxyl, straight chain or branched alkoxy with up to 6 carbon atoms or by phenyl, which in turn might be substituted by halogen, nitro, trifluormethyl, trifluoromethoxy or by phenyl or by tetrazole-substituted phenyl, and alkyl, optionally be substituted by a group with the formula $BOR_{X-22}$, in which
$R_{X-22}$ denotes a straight chain or branched acyl with up to 4 carbon atoms or benzyl, or $R_{X-19}$ denotes straight chain or branched acyl with up to 20 carbon atoms or benzoyl, that is optionally substituted by halogen, trifluoromethyl, nitro or trifluoromethoxy, or it denotes straight chain or branched fluoroacyl with up to 8 carbon atoms and 9 fluorine atoms, $R_{X-20}$ and $R_{X-21}$ are identical or different and denote hydrogen, phenyl or straight chain or branched alkyl with up to 6 carbon atoms, or $R_{X-20}$ and $R_{X-21}$ together form a 3- to 6-membered carbocyclic ring, and the carbocyclic rings formed are optionally substituted, optionally also geminally, with up to six identical or different substituents in the form of trifluoromethyl, hydroxy, nitrile, halogen, carboxyl, nitro, azido, cyano, cycloalkyl or cycloalkyloxy with 3 to 7 carbon atoms each, by straight chain or branched alkoxycarbonyl, alkoxy or alkylthio with up to 6 carbon atoms each or by straight chain or branched alkyl with up to 6 carbon atoms, which in turn is substituted with up to 2 identically or differently by hydroxyl, benzyloxy, trifluoromethyl, benzoyl, straight chain or branched alkoxy, oxyacyl or carbonyl with up to 4 carbon atoms each and/or phenyl, which may in turn be substituted with a halogen, trifluoromethyl or trifluoromethoxy, and/or the formed carbocyclic rings are optionally substituted, also geminally, with up to 5 identical or different substituents in the form of phenyl, benzoyl, thiophenyl or sulfonylbenzyl, which in turn are optionally substituted by halogen, trifluoromethyl, trifluoromethoxy or nitro, and/or optionally are substituted by a radical with the formula

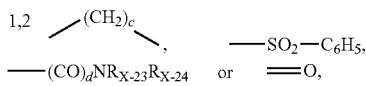

in which
c denotes a number equaling 1, 2, 3, or 4,
d denotes a number equaling 0 or 1,
$R_{X-23}$ and $R_{X-24}$ are identical or different and denote hydrogen, cycloalkyl with 3 to 6 carbon atoms, straight chain or branched alkyl with up to 6 carbon atoms, benzyl or phenyl, that is optionally substituted with up to 2 identically or differently by halogen, trifluoromethyl, cyano, phenyl or nitro, and/or the formed carbocyclic rings are substituted optionally by a spiro-linked radical with the formula

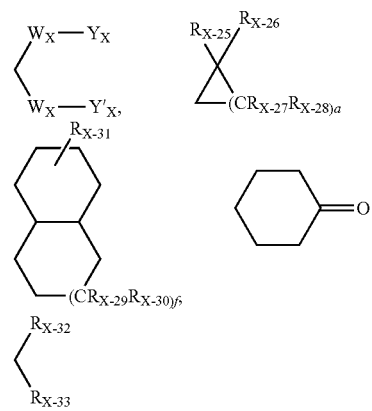

in which
$W_X$ denotes either an oxygen or a sulfur atom
$Y_X$ and $Y'_X$ together form a 2 to 6 membered straight chain or branched alkylene chain,
e denotes a number equaling 1, 2, 3, 4, 5, 6, or 7,
f denotes a number equaling 1 or 2,
$R_{X-25}$, $R_{X-26}$, $R_{X-27}$, $R_{X-28}$, $R_{X-29}$, $R_{X-30}$ and $R_{X-31}$ are identical or different and denote hydrogen, trifluoromethyl, phenyl, halogen or straight chain or branched alkyl or alkoxy with up to 6 carbon atoms each, or $R_{X-25}$ and $R_{X-26}$ or $R_{X-27}$ and $R_{X-28}$ respectively form together a straight chain or branched alkyl chain with up to 6 carbon atoms, or $R_{X-25}$ and $R_{X-26}$ or $R_{X-27}$ and $R_{X-28}$ each together form a radical with the formula

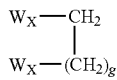

in which
$W_X$ has the meaning given above,
g denotes a number equaling 1, 2, 3, 4, 5, 6, or 7,
$R_{X-32}$ and $R_{X-33}$ form together a 3- to 7-membered heterocycle, which contains an oxygen or sulfur atom or a group with the formula SO, $SO_2$ or —$NR_{X-34}$, in which
$R_{X-34}$ denotes hydrogen, phenyl, benzyl or straight or branched alkyl with up to 4 carbon atoms.

Compounds of Formula X and their methods of manufacture are disclosed in PCT Publication No. WO 9914215, which is incorporated herein by reference in its entirety for all purposes.

In a preferred embodiment, the CETP inhibitor is selected from the following compounds of Formula X:

2-cyclopentyl-5-hydroxy-7,7-dimethyl-4-(3-thienyl)-3-(4-trifluoromethylbenxoyl)-5,6,7,8-tetrahydroquinoline;

2-cyclopentyl-3-[fluoro-(4-trifluoromethylphenyl)methyl]-5-hydroxy-7,7-dimethyl-4-(3-thienyl)-5,6,7,8-tetrahydroquinoline; and 2-cyclopentyl-5-hydroxy-7,7-dimethyl-4-(3-thienyl)-3-(trifluoromethylbenxyl)-5,6,7,8-tetrahydroquinoline.

Another class of CETP inhibitors that finds utility with the present invention consists of substituted tetrahydro naphthalines and analogous compound having the Formula XI

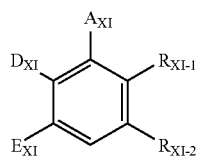

Formula XI and stereoisomers, stereoisomer mixtures, and salts thereof, in which $A_{XI}$ stands for cycloalkyl with 3 to 8 carbon atoms, or stands for aryl with 6 to 10 carbon atoms, or stands for a 5- to 7-membered, saturated, partially unsaturated or unsaturated, possibly benzocondensated, heterocycle with up to 4 heteroatoms from the series S, N and/or O, where aryl and the heterocyclic ring systems mentioned above are substituted up to 5-fold, identical or different, by cyano, halogen, nitro, carboxyl, hydroxy, trifluoromethyl, trifluoro-methoxy, or by straight-chain or branched alkyl, acyl, hydroxyalkyl, alkylthio, alkoxycarbonyl, oxyalkoxycarbonyl or alkoxy each with up to 7 carbon atoms, or by a group of the formula

—$NR_{XI-3}R_{XI-4}$, in which $R_{XI-3}$ and $R_{XI-4}$ are identical or different and denote hydrogen, phenyl, or straight-chain or branched alkyl with up to 6 carbon atoms $D_{XI}$ stands for a radical of the formula

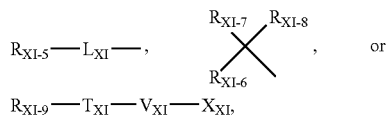

in which $R_{XI-5}$, $R_{XI-6}$ and $R_{XI-9}$, independent of each other, denote cycloalkyl with 3 to 6 carbon atoms, or denote aryl with 6 to 10 carbon atoms, or denote a 5- to 7-membered, possibly benzocondensated, saturated or unsaturated, mono-, bi- or tricyclic heterocycle with up to 4 heteroatoms of the series S, N and/or O, where the cycles are possibly substitutedCin the case of the nitrogen-containing rings also via the N-functionCup to 5-fold, identical or different, by halogen, trifluoromethyl, nitro, hydroxy, cyano, carboxyl, trifluoromethoxy, straight-chain or branched acyl, alkyl, alkylthio, alkylalkoxy, alkoxy or alkoxycarbonyl with up to 6 carbon atoms each by aryl or trifluoromethyl substituted aryl with 6 to 10 carbon atoms each, or by a possibly benzocondensated aromatic 5- to 7-membered heterocycle with up to 3 heteroatoms of the series S, N and/or O, and/or are substituted by a group of the formula —$OR_{XI-10}$, —$SR_{XI-11}$, —$SO_2R_{XI-12}$ or —$NR_{XI-13}R_{XI-14}$, in which $R_{XI-10}$, $R_{XI-11}$ and $R_{XI-12}$, independent of each other, denote aryl with 6 to 10 carbon atoms, which itself is substituted up to 2-fold, identical or different, by phenyl, halogen, or by straight-chain or branched alkyl with up to 6 carbon atoms, $R_{XI-13}$ and $R_{XI-14}$ are identical or different and have the meaning given above for $R_{XI-3}$ and $R_{XI-4}$, or $R_{XI-5}$ and/or $R_{XI-6}$ denote a radical of the formula

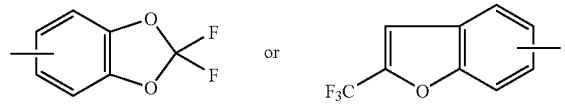

$R_{XI-7}$ denotes hydrogen, halogen or methyl, and $R_{XI-8}$ denotes hydrogen, halogen, azido, trifluoromethyl, hydroxy, trifluoromethoxy, straight-chain or branched alkoxy or alkyl with up to 6 carbon atoms each, or a radical of the formula —$NR_{XI-15}R_{XI-16}$, in which $R_{XI-15}$ and $R_{XI-16}$ are identical or different and have the meaning given above for $R_{XI-3}$ and $R_{XI-4}$, or $R_{XI-7}$ and $R_{XI-8}$ together form a radical of the formula =O or =$NR_{XI-17}$, in which $R_{XI-17}$ denotes hydrogen or straight-chain or branched alkyl, alkoxy or acyl with up to 6 carbon atoms each, $L_{XI}$ denotes a straight-chain or branched alkylene- or alkenylene chain with up to 8 carbon atoms each, which is possibly substituted up to 2-fold by hydroxy, $T_{XI}$ and $X_{XI}$ are identical or different and denote a straight-chain or branched alkylene chain with up to 8 carbon atoms, or $T_{XI}$ and $X_{XI}$ denotes a bond, $V_{XI}$ stands for an oxygen- or sulfur atom or for an —$NR_{XI-18}$ group, in which $R_{XI-18}$ denotes hydrogen or straight-chain or branched alkyl with up to 6 carbon atoms, or phenyl, $E_{XI}$ stands for cycloalkyl with 3 to 8 carbon atoms, or stands for straight-chain or branched alkyl with up to 8 carbon atoms, which is possibly substituted by cycloalkyl with 3 to 8 carbon atoms or hydroxy, or stands for phenyl, which is possibly substituted by halogen or trifluoromethyl, $R_{XI-1}$ and $R_{XI-2}$ together form a straight-chain or branched alkylene chain with up to 7 carbon atoms, which must be substituted by a carbonyl group and/or by a radical of the formula

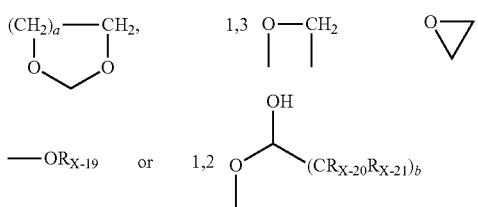

in which
a and b are identical or different and denote a number 1, 2 or 3

$R_{XI-19}$ denotes hydrogen, cycloalkyl with 3 to 7 carbon atoms, straight-chain or branched silylalkyl with up to 8 carbon atoms, or straight-chain or branched alkyl with up to 8 carbon atoms, which is possibly substituted by hydroxy, straight-chain or branched alkoxy with up to 6 carbon atoms, or by phenyl, which itself can be substituted by halogen, nitro, trifluoromethyl, trifluoromethoxy or by phenyl substituted by phenyl or tetrazol, and alkyl is possibly substituted by a group of the formula —$OR_{XI-22}$, in which
$R_{XI-22}$ denotes straight-chain or branched acyl with up to 4 carbon atoms, or benzyl, or
$R_{XI-19}$ denotes straight-chain or branched acyl with up to 20 carbon atoms or benzoyl, which is possibly substituted by halogen, trifluoromethyl, nitro or trifluoromethoxy, or denotes straight-chain or branched fluoroacyl with up to 8 carbon atoms and 9 fluorine atoms, $R_{XI-20}$ and $R_{XI-21}$ are identical or different, denoting hydrogen, phenyl or straight-chain or branched alkyl with up to 6 carbon atoms, or
$R_{XI-20}$ and $R_{XI-21}$ together form a 3- to 6-membered carbocycle, and, possibly also geminally, the alkylene chain formed by $R_{XI-1}$ and $R_{XI-2}$, is possibly substituted up to 6-fold, identical or different, by trifluoromethyl, hydroxy, nitrile, halogen, carboxyl, nitro, azido, cyano, cycloalkyl or cycloalkyloxy with 3 to 7 carbon atoms each, by straight-chain or branched alkoxycarbonyl, alkoxy or alkoxythio with up to 6 carbon atoms each, or by straight-chain or branched alkyl with up to 6 carbon atoms, which itself is substituted up to 2-fold, identical or different, by hydroxyl, benzyloxy, trifluoromethyl, benzoyl, straight-chain or branched alkoxy, oxyacyl or carboxyl with up to 4 carbon atoms each, and/or phenyl—which itself can be substituted by halogen, trifluoromethyl or trifluoromethoxy, and/or the alkylene chain formed by $R_{XI-1}$ and $R_{XI-2}$ is substituted, also geminally, possibly up to 5-fold, identical or different, by phenyl, benzoyl, thiophenyl or sulfobenzyl—which themselves are possibly substituted by halogen, trifluoromethyl, trifluoromethoxy or nitro, and/or the alkylene chain formed by $R_{XI-1}$ and $R_{XI-2}$ is possibly substituted by a radical of the formula

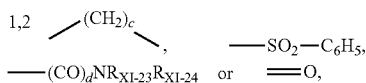

in which
c denotes a number 1, 2, 3 or 4,
d denotes a number 0 or 1, $R_{XI-23}$ and $R_{XI-24}$ are identical or different and denote hydrogen, cycloalkyl with 3 to 6 carbon atoms, straight-chain or branched alkyl with up to 6 carbon atoms, benzyl or phenyl, which is possibly substituted up to 2-fold. identical or different, by halogen, trifluoromethyl, cyano, phenyl or nitro, and/or the alkylene chain formed by $R_{XI-1}$ and $R_{XI-2}$ is possibly substituted by a spiro-jointed radical of the formula

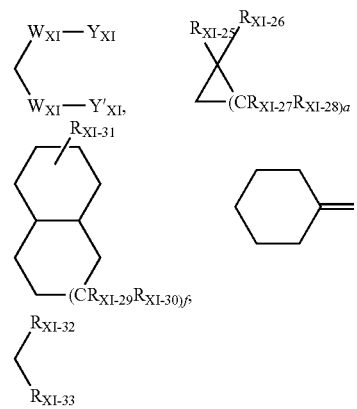

in which
$W_{XI}$ denotes either an oxygen or a sulfur atom,
$Y_{XI}$ and $Y'_{XI}$ together form a 2- to 6-membered straight-chain or branched alkylene chain,
e is a number 1, 2, 3, 4, 5, 6 or 7,
f denotes a number 1 or 2,
$R_{XI-25}$, $R_{XI-26}$, $R_{XI-27}$, $R_{XI-28}$, $R_{XI-29}$, $R_{XI-30}$ and $R_{XI-31}$ are identical or different and denote hydrogen, trifluoromethyl, phenyl, halogen, or straight-chain or branched alkyl or alkoxy with up to 6 carbon atoms each, or
$R_{XI-25}$ and $R_{XI-26}$ or $R_{XI-27}$ and $R_{XI-28}$ together form a straight-chain or branched alkyl chain with up to 6 carbon atoms, or
$R_{XI-25}$ and $R_{XI-26}$ or $R_{XI-27}$ and $R_{XI-28}$ together form a radical of the formula

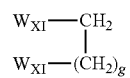

in which
$W_{XI}$ has the meaning given above,
g is a number 1, 2, 3, 4, 5, 6 or 7,
$R_{XI-32}$ and $R_{XI-33}$ together form a 3- to 7-membered heterocycle that contains an oxygen- or sulfur atom or a group of the formula SO, $SO_2$ or —$NR_{XI-34}$,
in which
$R_{XI-34}$ denotes hydrogen, phenyl, benzyl, or straight-chain or branched alkyl with up to 4 carbon atoms.

Compounds of Formula XI and their methods of manufacture are disclosed in PCT Publication No. WO 9914174, which is incorporated herein by reference in its entirety for all purposes.

Another class of CETP inhibitors that finds utility with the present invention consists of 2-aryl-substituted pyridines having the Formula (XII)

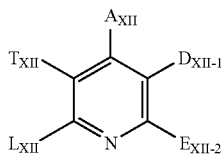

Formula XII or pharmaceutically acceptable salts, enantiomers, or stereoisomers of said compounds,
in which
$A_{XII}$ and $E_{XII}$ are identical or different and stand for aryl with 6 to 10 carbon atoms which is possibly substituted, up to 5-fold identical or different, by halogen, hydroxy, trifluoromethyl, trifluoromethoxy, nitro or by straight-chain or branched alkyl, acyl, hydroxy alkyl or alkoxy with up to 7 carbon atoms each, or by a group of the formula —$NR_{XII-1}R_{XII-2}$,
where
$R_{XII-1}$ and $R_{XII-2}$ are identical or different and are meant to be hydrogen, phenyl or straight-chain or branched alkyl with up to 6 carbon atoms,
$D_{XII}$ stands for straight-chain or branched alkyl with up to 8 carbon atoms, which is substituted by hydroxy,
$L_{XII}$ stands for cycloalkyl with 3 to 8 carbon atoms or for straight-chain or branched alkyl with up to 8 carbon atoms, which is possibly substituted by cycloalkyl with 3 to 8 carbon atoms, or by hydroxy,
$T_{XII}$ stands for a radical of the formula $R_{XII-3}$—$X_{XII}$— or

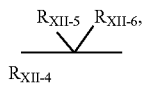

where
$R_{XII-3}$ and $R_{XII-4}$ are identical or different and are meant to be cycloalkyl with 3 to 8 carbon atoms, or aryl with 6 to 10 carbon atoms, or a 5- to 7-membered aromatic, possibly benzocondensated heterocycle with up to 3 heteroatoms from the series S, N and/or O, which are possibly substituted. up to 3-fold identical or different, by trifluoromethyl, trifluoromethoxy, halogen, hydroxy, carboxyl, nitro, by straight-chain or branched alkyl, acyl, alkoxy or alkoxycarbonyl with up to 6 carbon atoms each. or by phenyl, phenoxy or phenylthio which in turn can be substituted by halogen. trifluoromethyl or trifluoromethoxy, and/or where the cycles are possibly substituted by a group of the formula —$NR_{XII-7}R_{XII-8}$,
where
$R_{XII-7}$ and $R_{XII-8}$ are identical or different and have the meaning of $R_{XII-1}$ and $R_{XII-2}$ given above,
$X_{XII}$ is a straight-chain or branched alkyl or alkenyl with 2 to 10 carbon atoms each, possibly substituted up to 2-fold by hydroxy or halogen,
$R_{XII-5}$ stands for hydrogen, and
$R_{XII-6}$ means to be hydrogen, halogen, mercapto, azido, trifluoromethyl, hydroxy, trifluoromethoxy, straight-chain or branched alkoxy with up to 5 carbon atoms, or a radical of the formula $BNR_{XII-9}R_{XII-10}$,
where
$R_{XII-9}$ and $R_{XII-10}$ are identical or different and have the meaning of $R_{XII-1}$ and $R_{XII-2}$ given above, or
$R_{XII-5}$ and $R_{XII-6}$, together with the carbon atom, form a carbonyl group.

Compounds of Formula XII and their methods of manufacture are disclosed in EP 796846-A1, U.S. Pat. Nos. 6,127,383 and 5,925,645, all of which are incorporated herein by reference in their entireties for all purposes.

In a preferred embodiment, the CETP inhibitor is selected from the following compounds of Formula XII:
4,6-bis-(p-fluorophenyl)-2-isopropyl-3-[(p-trifluoromethylphenyl)-(fluoro)-methyl]-5-(1-hydroxyethyl)pyridine;
2,4-bis-(4-fluorophenyl)-6-isopropyl-5-[4-(trifluoromethylphenyl)-fluoromethyl]-3-hydroxymethyl)pyridine; and
2,4-bis-(4-fluorophenyl)-6-isopropyl-5-[2-(3-trifluoromethylphenyl)vinyl]-3-hydroxymethyl)pyridine.

Another class of CETP inhibitors that finds utility with the present invention consists of compounds having the Formula (XIII)

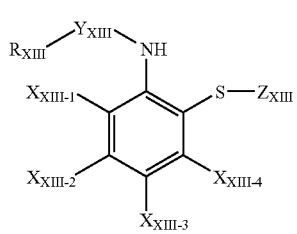

Formula XIII or pharmaceutically acceptable salts, enantiomers, stereoisomers, hydrates, or solvates of said compounds, in which
$R_{XIII}$ is a straight chain or branched $C_{1-10}$ alkyl; straight chain or branched $C_{2-10}$ alkenyl; halogenated $C_{1-4}$ lower alkyl; $C_{3-10}$ cycloalkyl that may be substituted; $C_{5-8}$ cycloalkenyl that may be substituted; $C_{3-10}$ cycloalkyl $C_{1-10}$ alkyl that may be substituted; aryl that may be substituted; aralkyl that may be substituted; or a 5- or 6-membered heterocyclic group having 1 to 3 nitrogen atoms, oxygen atoms or sulfur atoms that may be substituted,
$X_{XIII-1}$, $X_{XIII-2}$, $X_{XIII-3}$, $X_{XIII-4}$ may be the same or different and are a hydrogen atom; halogen atom; $C_{1-4}$ lower alkyl; halogenated $C_{1-4}$ lower alkyl; $C_{1-4}$ lower alkoxy; cyano group; nitro group; acyl; or aryl, respectively;
$Y_{XIII}$ is —CO—; or $BSO_2$—; and
$Z_{XIII}$ is a hydrogen atom; or mercapto protective group.

Compounds of Formula XIII and their methods of manufacture are disclosed in PCT Publication No. WO 98/35937, which is incorporated herein by reference in its entirety for all purposes.

In a preferred embodiment, the CETP inhibitor is selected from the following compounds of Formula XIII:
N,N'-(dithiodi-2,1-phenylene)bis[2,2-dimethyl-propanamide];
N,N'-(dithiodi-2,1-phenylene)bis[1-methyl-cyclohexanecarboxamide];
N,N'-(dithiodi-2,1-phenylene)bis[1-(3-methylbutyl)-cyclopentanecarboxamide];
N,N'-(dithiodi-2,1-phenylene)bis[1-(3-methylbutyl)-cyclohexanecarboxamide];
N,N'-(dithiodi-2,1-phenylene)bis[1-(2-ethylbutyl)-cyclohexanecarboxamide];
N,N'-(dithiodi-2,1-phenylene)bis-tricyclo[3.3.1.1$^{3,7}$]decane-1-carboxamide;

propanethioic acid, 2-methyl-,S-[2-[[[1-(2-ethylbutyl)cyclohexyl]carbonyl]amino]phenyl]ester;
propanethioic acid, 2,2-dimethyl-,S-[2-[[[1-(2-ethylbutyl)cyclohexyl]carbonyl]amino]phenyl]ester; and
ethanethioic acid, S-[2-[[[1-(2-ethylbutyl)cyclohexyl]carbonyl]amino]phenyl]ester.

Another class of CETP inhibitors that finds utility with the present invention consists of polycyclic aryl and heteroaryl tertiary-heteroalkylamines having the Formula XIV

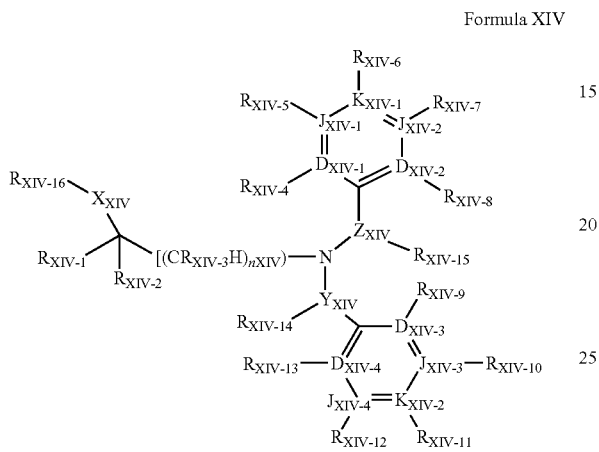

Formula XIV and pharmaceutically acceptable forms thereof, wherein:

$n_{XIV}$ is an integer selected from 0 through 5;

$R_{XIV-1}$ is selected from the group consisting of haloalkyl, haloalkenyl, haloalkoxyalkyl, and haloalkenyloxyalkyl;

$X_{XIV}$ is selected from the group consisting of O, H, F, S, S(O), NH, N(OH), N(alkyl), and N(alkoxy);

$R_{XIV-16}$ is selected from the group consisting of hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, dialkoxyphosphonoalkyl, trialkylsilyl, and a spacer selected from the group consisting of a covalent single bond and a linear spacer moiety having from 1 through 4 contiguous atoms linked to the point of bonding of an aromatic substituent selected from the group consisting of $R_{XIV-4}$, $R_{XIV-8}$, $R_{XIV-9}$, and $R_{XIV-13}$ to form a heterocyclyl ring having from 5 through 10 contiguous members with the provisos that said spacer moiety is other than a covalent single bond when $R_{XIV-2}$ is alkyl and there is no $R_{XIV-16}$ wherein X is H or F;

$D_{XIV-1}$, $D_{XIV-2}$, $J_{XIV-1}$, $J_{XIV-2}$ and $K_{XIV-1}$ are independently selected from the group consisting of C, N, O, S and a covalent bond with the provisos that no more than one of $D_{XIV-1}$, $D_{XIV-2}$, $J_{XIV-1}$, $J_{XIV-2}$ and $K_{XIV-1}$ is a covalent bond, no more than one of $D_{XIV-1}$, $D_{XIV-2}$, $J_{XIV-1}$, $J_{XIV-2}$ and $K_{XIV-1}$ is O, no more than one of $D_{XIV-1}$, $D_{XIV-2}$, $J_{XIV-1}$, $J_{XIV-2}$ and $K_{XIV-1}$ is S, one of $D_{XIV-1}$, $D_{XIV-2}$, $J_{XIV-1}$, $J_{XIV-2}$ and $K_{XIV-1}$ must be a covalent bond when two of $D_{XIV-1}$, $D_{XIV-2}$, $J_{XIV-1}$, $J_{XIV-2}$ and $K_{XIV-1}$ are O and S, and no more than four of $D_{XIV-1}$, $D_{XIV-2}$, $J_{XIV-1}$, $J_{XIV-2}$ and $K_{XIV-1}$ are N;

$D_{XIV-3}$, $D_{XIV-4}$, $J_{XIV-3}$, $J_{XIV-4}$ and $K_{XIV-2}$ are independently selected from the group consisting of C, N, O, S and a covalent bond with the provisos that no more than one of $D_{XIV-3}$, $D_{XIV-4}$, $J_{XIV-3}$, $J_{XIV-4}$ and $K_{XIV-2}$ is a covalent bond, no more than one of $D_{XIV-3}$, $D_{XIV-4}$, $J_{XIV-3}$, $J_{XIV-4}$ and $K_{XIV-2}$ is O, no more than one of $D_{XIV-3}$, $D_{XIV-4}$, $J_{XIV-3}$, $J_{XIV-4}$ and $K_{XIV-2}$ is S, one of $D_{XIV-3}$, $D_{XIV-4}$ $J_{XIV-3}$, $J_{XIV-4}$ and $K_{XIV-2}$ must be a covalent bond when two of $D_{XIV-3}$, $D_{XIV-4}$, $J_{XIV-3}$, $J_{XIV-4}$ and $K_{XIV-2}$ are O and S, and no more than four of $D_{XIV-3}$, $D_{XIV-4}$ $J_{XIV-3}$, $J_{XIV-4}$ and $K_{XIV-2}$ and $K_{XIV-2}$ are N;

$R_{XIV-2}$ is independently selected from the group consisting of hydrido, hydroxy, hydroxyalkyl, amino, aminoalkyl, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, aloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$R_{XIV-2}$ and $R_{XIV-3}$ are taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

$R_{XIV-3}$ is selected from the group consisting of hydrido, hydroxy, halo, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$Y_{XIV}$ is selected from a group consisting of a covalent single bond, $(C(R_{XIV-14})_2)_{qXIV}$ wherein $qXIV$ is an integer selected from 1 and 2 and $(CH(R_{XIV-14}))_{gXIV}$—$W_{XIV}$—$(CH(R_{XIV-14}))_{pXIV}$ wherein $gXIV$ and $pXIV$ are integers independently selected from 0 and 1;

$R_{XIV-14}$ is independently selected from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-9}$ and $R_{XIV-13}$ to form a ring selected from the group consisting of a cycloalkenyl ring having from 5 through 8 contiguous members and a heterocyclyl ring having from 5 through 8 contiguous members and a spacer selected from a moiety having a chain length of 2 to 5 atoms connected to the point of bonding selected from the group consisting of $R_{XIV-4}$ and $R_{XIV-8}$ to form a heterocyclyl having from 5 through 8 contiguous members with the proviso that, when $Y_{XIV}$ is a covalent bond, an $R_{XIV-14}$ substituent is not attached to $Y_{XIV}$;

$R_{XIV-14}$ and $R_{XIV-14}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-14}$ and $R_{XIV-14}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$W_{XIV}$ is selected from the group consisting of O, C(O), C(S), C(O)N($R_{XIV-14}$), C(S)N($R_{XIV-14}$), ($R_{XIV-14}$)NC(O), ($R_{XIV-14}$)NC(S), S, S(O), S(O)$_2$, S(O)$_2$N($R_{XIV-14}$), ($R_{XIV-14}$)NS(O)$_2$, and N($R_{XIV-14}$) with the proviso that $R_{XIV-14}$ is selected from other than halo and cyano;

$Z_{XIV}$ is independently selected from a group consisting of a covalent single bond, $(C(R_{XIV-15})_2)_{qXIV-2}$ wherein $qXIV-2$ is an integer selected from 1 and 2, $(CH(R_{XIV-15}))_{jXIV}$—W—$(CH(R_{XIV-15}))_{kXIV}$ wherein $jXIV$ and $kXIV$ are integers independently selected from 0 and 1 with the proviso that, when $Z_{XIV}$ is a covalent single bond, an $R_{XIV-15}$ substituent is not attached to $Z_{XIV}$;

$R_{XIV-15}$ is independently selected, when $Z_{XIV}$ is $(C(R_{XIV-15})_2)_{qXIV}$ wherein $qXIV$ is an integer selected from 1 and 2, from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfinyl, heteroarylsulfonyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_{XIV-9}$ and $R_{XIV-13}$ to form a heterocyclyl having from 5 through 8 contiguous members;

$R_{XIV-15}$ and $R_{XIV-15}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-15}$ and $R_{XIV-15}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$R_{XIV-15}$ is independently selected, when $Z_{XIV}$ is $(CH(R_{XIV-15}))_{jXIV}$—W—$(CH(R_{XIV-15}))_{kXIV}$ wherein $_{jXIV}$ and $_{kXIV}$ are integers independently selected from 0 and 1, from the group consisting of hydrido, halo, cyano, aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl, a spacer selected from a linear moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a linear moiety having a chain length of 2 to 5 atoms connected to the point of bonding selected from the group consisting of $R_{XIV-9}$ and $R_{XIV-13}$ to form a heterocyclyl ring having from 5 through 8 contiguous members;

$R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkylamidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocydylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl; haloalkenyl, haloalkoxy, hydroxyhaloalkyl, hydroxyaralkyl, hydroxyalkyl, hydroxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that there are one to five non-hydrido ring substituents $R_{XIV-4}$, $R_{XIV-5}$, $R_{XIV-6}$, $R_{XIV-7}$, and $R_{XIV-8}$ present, that there are one to five non-hydrido ring substituents $R_{XIV-9}$, $R_{XIV-10}$, $R_{XIV-11}$, $R_{XIV-12}$, and $R_{XIV-13}$ present, and $R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are each independently selected to maintain the tetravalent nature of carbon, trivalent nature of nitrogen, the divalent nature of sulfur, and the divalent nature of oxygen;

$R_{XIV-4}$ and $R_{XIV-5}$, $R_{XIV-5}$ and $R_{XIV-6}$, $R_{XIV-6}$ and $R_{XIV-7}$, $R_{XIV-7}$ and $R_{XIV-8}$, $R_{XIV-8}$ and $R_{XIV-9}$, $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XIV-4}$ and $R_{XIV-5}$, $R_{XIV-5}$ and $R_{XIV-6}$, $R_{XIV-6}$ and $R_{XIV-7}$, and $R_{XIV-7}$ and $R_{XIV-8}$ are used at the same time and that no more than one of the group consisting of spacer pairs $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are used at the same time;

$R_{XIV-4}$ and $R_{XIV-9}$, $R_{XIV-4}$ and $R_{XIV-13}$, $R_{XIV-8}$ and $R_{XIV-9}$, and $R_{XIV-8}$ and $R_{XIV-13}$ are independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XIV-4}$ and $R_{XIV-9}$, $R_{XIV-4}$ and $R_{XIV-13}$, $R_{XIV-8}$ and $R_{XIV-9}$, and $R_{XIV-8}$ and $R_{XIV-13}$ is used at the same time.

Compounds of Formula XIV and their methods of manufacture are disclosed in PCT Publication No. WO 00/18721, which is incorporated herein by reference in its entirety for all purposes.

In a preferred embodiment, the CETP inhibitor is selected from the following compounds of Formula XIV:

3-[[3-(3-trifluoromethoxyphenoxy)phenyl][(3-(1,1,2,2-tetrafluoroethoxy)-phenyl]methyl]amino]-1,1,1-trifluoro-2-propanol;
3-[[3-(3-isopropylphenoxy)phenyl][[3-(1,1,2,2-tetrafluoroethoxy)phenyl]-methyl]amino]-1,1,1-trifluoro-2-propanol;
3-[[3-(3-cyclopropylphenoxy)phenyl][[3-(1,1,2,2-tetrafluoroethoxy)phenyl]-methyl]amino]-1,1,1-trifluoro-2-propanol;
3-[[3-(3-(2-furyl)phenoxy)phenyl][[3-(1,1,2,2-tetrafluoroethoxy)phenyl]-methyl]amino]-1,1,1-trifluoro-2-propanol;
3-[[3-(2,3-dichlorophenoxy)phenyl][[3-(1,1,2,2-tetrafluoroethoxy)phenyl]-methyl]amino]-1,1,1-trifluoro-2-propanol;
3-[[3-(4-fluorophenoxy)phenyl][[3-(1,1,2,2-tetrafluoroethoxy)phenyl]-methyl]amino]-1,1,1-trifluoro-2-propanol;
3-[[3-(4-methlylphenoxy)phenyl][[3-(1,1,2,2-tetrafluoroethoxy)phenyl]-methyl]amino]-1,1,1-trifluoro-2-propanol;
3-[[3-(2-fluoro-5-bromophenoxy)phenyl][[3-(1,1,2,2-tetrafluoroethoxy)phenyl]-methyl]amino]-1,1,1-trifluoro-2-propanol;
3-[[3-(4-chloro-3-ethylphenoxy)phenyl][[3-(1,1,2,2-tetrafluoroethoxy)phenyl]-methyl]amino]-1,1,1-trifluoro-2-propanol;
3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;
3-[[3-[3-(pentafluoroethyl)phenoxy]phenyl][[3-(1,1,2,2-tetrafluoroethoxy)-phenyl]methyl]amino]-1,1,1-trifluoro-2-propanol;
3-[[3-(3,5-dimethylphenoxy)phenyl][[3-(1,1,2,2-tetrafluoroethoxy)phenyl]-methyl]amino]-1,1,1-trifluoro-2-propanol;
3-[[3-(3-ethylphenoxy)phenyl][[3-(1,1,2,2-tetrafluoroethoxy)phenyl]-methyl]amino]-1,1,1-trifluoro-2-propanol;
3-[[3-(3-t-butylphenoxy)phenyl][[3-(1,1,2,2-tetrafluoroethoxy)phenyl]-methyl]amino]1,1,1-trifluoro-2-propanol;
3-[[3-(3-methylphenoxy)phenyl][[3-(1,1,2,2-tetrafluoroethoxy)phenyl]-methyl]amino]-1,1,1-trifluoro-2-propanol;
3-[[3-(5,6,7,8-tetrahydro-2-naphthoxy)phenyl][[3-(1,1,2,2-tetrafluoroethoxy)phenyl]methyl]amino]-1,1,1-trifluoro-2-propanol;
3-[[3-(phenoxy)phenyl][[3-(1,1,2,2-tetrafluoroethoxy)phenyl]methyl]amino]-1,1,1-trifluoro-2-propanol;
3-[[3-[3-(N,N-dimethylamino)phenoxy]phenyl][[3-(1,1,2,2-tetrafluoroethoxy)phenyl]methyl]amino]-1,1,1-trifluoro-2-propanol;
3-[[[3-(1,1,2,2-tetrafluoroethoxy)phenyl]methyl][3-[[3-(trifluoromethoxy)-phenyl]methoxy]phenyl]amino]-1,1,1-trifluoro-2-propanol;
3-[[[3-(1,1,2,2-tetrafluoroethoxy)phenyl]methyl][3-[[3-(trifluoromethyl)-phenyl]methoxy]phenyl]amino]-1,1,1-trifluoro-2-propanol;
3-[[[3-(1,1,2,2-tetrafluoroethoxy)phenyl]methyl][3-[[3,5-dimethylphenyl]-methoxy]phenyl]amino]-1,1,1-trifluoro-2-propanol;
3-[[[3-(1,1,2,2-tetrafluoroethoxy)phenyl]methyl][3-[[3-(trifluoromethylthio)-phenyl]methoxy]phenyl]amino]-1,1,-trifluoro-2-propanol;
3-[[[3-(1,1,2,2-tetrafluoroethoxy)phenyl]methyl][3-[[3,5-difluorophenyl]-methoxy]phenyl]amino]-1,1,1-trifluoro-2-propanol;
3-[[[3-(1,1,2,2-tetrafluoroethoxy)phenyl]methyl][3-[cyclohexylmethoxy]-phenyl]amino]-1,1,1-trifluoro-2-propanol;
3-[[3-(2-difluoromethoxy-4-pyridyloxy)phenyl][[3-(1,1,2,2-tetrafluoroethoxy)-phenyl]methyl]amino]-1,1,1-trifluoro-2-propanol;
3-[[3-(2-trifluoromethyl-4-pyridyloxy)phenyl][[3-(1,1,2,2-tetrafluoroethoxy)-phenyl]methyl]amino]-1,1,1-trifluoro-2-propanol;
3-[[3-(3-difluoromethoxyphenoxy)phenyl][[3-(1,1,2,2-tetrafluoroethoxy)-phenyl]methyl]amino]-1,1,1-trifluoro-2-propanol;
3-[[[3-(3-trifluoromethylthio)phenoxy]phenyl][[3-(1,1,2,2-tetrafluoroethoxy)-phenyl]methyl]amino]-1,1,1-trifluoro-2-propanol;
3-[[3-(4-chloro-3-trifluoromethylphenoxy)phenyl][[3-(1,1,2,2-tetrafluoroethoxy)-phenyl]methyl]amino]-1,1,1-trifluoro-2-propanol;
3-[[3-(trifluoromethoxyphenoxy)phenyl][[3-(pentafluoroethymethyl]amino]-1,1,1-trifluoro-2-propanol;
3-[[3-(3-isopropylphenoxy)phenyl][[3-(pentafluoroethyl)phenyl]methyl]-amino]-1,1,1-trifluoro-2-propanol;

3-[[3-(3-cyclopropylphenoxy)phenyl][[3-(pentafluoroethyl)phenyl]methyl]-amino]-1,1,1-trifluoro-2-propanol;
3-[[3-(3-(2-furyl)phenoxy)phenyl][[3-(pentafluoroethyl)phenyl]methyl]-amino]-1,1,1-trifluoro-2-propanol;
3-[[3-(2,3-dichlorophenoxy)phenyl][[3-(pentafluoroethyl)phenyl]methyl]-amino]-1,1,1-trifluoro-2-propanol;
3-[[3-(4-fluorophenoxy)phenyl][[3-(pentafluoroethyl)phenyl]methyl]amino]-1,1,1-trifluoro-2-propanol;
3-[[3-(4-methylphenoxy)phenyl][[3-(pentafluoroethyl)phenyl]methyl]amino]-1,1,1-trifluoro-2-propanol;
3-[[3-(2-fluoro-5-bromophenoxy)phenyl][[3-(pentafluoroethyl)phenyl]methyl]-amino]-1,1,1-trifluoro-2-propanol;
3-[[3-(4-chloro-3-ethylphenoxy)phenyl][[3-(pentafluoroethyl)phenyl]methyl]-amino]-1,1,1-trifluoro-2-propanol;
3-[[3-[3-(1,1,2,2-tetrafluoroethoxy)phenoxy]phenyl][[3-(pentafluoroethyl)-phenyl]methyl]amino]-1,1,1-trifluoro-2-propanol;
3-[[3-[3-(pentafluoroethyl)phenoxy]phenyl][[3-(pentafluoroethyl)phenyl]-methyl]amino]-1,1,1-trifluoro-2-propanol;
3-[[3-(3,5-dimethylphenoxy)phenyl][[3-(pentafluoroethyl)phenyl]methyl]-amino]-1,1,1-trifluoro-2-propanol;
3-[[3-(3-ethylphenoxy)phenyl][[3-(pentafluoroethyl)phenyl]methyl]amino]-1,1,1-trifluoro-2-propanol;
3-[[3-(3-t-butylphenoxy)phenyl][[3-(pentafluoroethyl)phenyl]methyl]amino]-1,1,1-trifluoro-2-propanol;
3-[[3-(3-methylphenoxy)phenyl][[3-pentafluoroethyl)phenyl]methyl]amino]-1,1,1-trifluoro-2-propanol;
3-[[3-(5,6,7,8-tetrahydro-2-naphthoxy)phenyl][[3-(pentafluoroethyl)phenyl]-methyl]amino]-1,1,1-trifluoro-2-propanol;
3-[[3-(phenoxy)phenyl][[3-(pentafluoroethyl)phenyl]methyl]amino]-1,1,1-trifluoro-2-propanol;
3-[[3-[3-(N,N-dimethylamino)phenoxy]phenyl][[3-(pentafluoroethyl)phenyl]-methyl]amino]-1,1,1-trifluoro-2-propanol;
3-[[[3-(pentafluoroethyl)phenyl]methyl][3-[[3-(trifluoromethoxy)phenyl]-methoxy]phenyl]amino]-1,1,1-trifluoro-2-propanol;
3-[[[3-(pentafluoroethyl)phenyl]methyl][3-[[3-(trifluoromethyl)phenyl]-methoxy]phenyl]amino]-1,1,1-trifluoro-2-propanol;
3-[[[3-(pentafluoroethyl)phenyl]methyl][3-[[3,5-dimethylphenyl]methoxy]-phenyl]amino]-1,1,1-trifluoro-2-propanol;
3-[[[3-(pentafluoroethyl)phenyl]methyl][3-[[3-(trifluoromethylthio)phenyl]-methoxy]phenyl]amino]-1,1,1-trifluoro-2-propanol;
3-[[[3-(pentafluoroethyl)phenyl]methyl][3-[[3,5-difluorophenyl]methoxy]-phenyl]amino]-1,1,1-trifluoro-2-propanol;
3-[[[3-(pentafluoroethyl)phenyl]methyl][3-[cyclohexylmethoxy]phenyl]-amino]-1,1,1-trifluoro-2-propanol;
3-[[3-(2-difluoromethoxy-4-pyridyloxy)phenyl][[3-(pentafluoroethyl)phenyl]-methyl]amino]-1,1,1-trifluoro-2-propanol;
3-[[3-(2-trifluoromethyl-4-pyridyloxy)phenyl][[3-(pentafluoroethyl)phenyl]-methyl]amino]-1,1,1-trifluoro-2-propanol;
3-[[3-(3-difluoromethoxyphenoxy)phenyl][[3-(pentafluoroethyl)phenyl]-methyl]amino]-1,1,1-trifluoro-2-propanol;
3-[[[3-(3-trifluoromethylthio)phenoxy)phenyl][[3-(pentafluoroethyl)phenyl]-methyl]amino]-1,1,1-trifluoro-2-propanol;
3-[[3-(4-chloro-3-trifluoromethylphenoxy)phenyl][[3-(pentafluoroethyl)-phenyl]methyl]amino]-1,1,1-trifluoro-2-propanol;
3-[[3-(3-trifluoromethoxyphenoxy)phenyl][[3-(heptafluoropropyl)phenyl]-methyl]amino]-1,1,1-trifluoro-2-propanol;
3-[[3-(3-isopropylphenoxy)phenyl][[3-(heptafluoropropyl)phenyl]methyl]-amino]-1,1,1-trifluoro-2-propanol;
3-[[3-(3-cyclopropylphenoxy)phenyl][[3-(heptafluoropropyl)phenyl]methyl]-amino]-1,1,1-trifluoro-2-propanol;
3-[[3-(3-(2-furyl)phenoxy)phenyl][[3-(heptafluoropropyl)phenyl]methyl]-amino]-1,1,1-trifluoro-2-propanol;
3-[[3-(2,3-dichlorophenoxy)phenyl][[3-(heptafluoropropyl)phenyl]methyl]amino]-1,1,1-trifluoro-2-propanol;
3-[[3-(4-fluorophenoxy)phenyl][[3-(heptafluoropropyl)phenyl]methyl]amino]-1,1,1-trifluoro-2-propanol;
3-[[3-(4-methylphenoxy)phenyl][[3-(heptafluoropropyl)phenyl]methyl]amino]-1,1,1-trifluoro-2-propanol;
3-[[3-(2-fluoro-5-bromophenoxy)phenyl][[3-(heptafluoropropyl)phenyl]methyl]-amino]-1,1,1-trifluoro-2-propanol;
3-[[3-(4-chloro-3-ethylphenoxy)phenyl][[3-(heptafluoropropyl)phenyl]methyl]-amino]-1,1,1-trifluoro-2-propanol;
3-[[3-[3-(1,1,2,2-tetrafluoroethoxy)phenoxy]phenyl][[3-(heptafluoropropyl)-phenyl]methyl]amino]-1,1,1-trifluoro-2-propanol;
3-[[3-[3-(pentafluoroethyl)phenoxy]phenyl][[3-(heptafluoropropyl)phenyl]-methyl]amino]-1,1,1-trifluoro-2-propanol;
3-[[3-(3,5-dimethylphenoxy)phenyl][[3-(heptafluoropropyl)phenyl]methyl]-amino]-1,1,1-trifluoro-2-propanol;
3-[[3-(3-ethylphenoxy)phenyl][[3-(heptafluoropropyl)phenyl]methyl]amino]-1,1,1-trifluoro-2-propanol;
3-[[3-(3-t-butylphenoxy)phenyl][[3-(heptafluoropropyl)phenyl]methyl]amino]-1,1,1-trifluoro-2-propanol;
3-[[3-(3-methylphenoxy)phenyl][[3-(heptafluoropropyl)phenyl]methyl]amino]-1,1,1-trifluoro-2-propanol;
3-[[3-(5,6,7,8-tetrahydro-2-naphthoxy)phenyl][[3-(heptafluoropropyl)phenyl]-methyl]amino]-1,1,1-trifluoro-2-propanol;
3-[[3-(phenoxy)phenyl][[3-(heptafluoropropyl)phenyl]methyl]amino]-1,1,1-trifluoro-2-propanol;
3-[[3-[3-(N,N-dimethylamino)phenoxy]phenyl][[3-(heptafluoropropyl)phenyl]-methyl]amino]-1,1,1-trifluoro-2-propanol;
3-[[[3-(heptafluoropropyl)phenyl]methyl][3-[[3-(trifluoromethoxy)phenyl]-methoxy]phenyl]amino]-1,1,1-trifluoro-2-propanol;
3-[[[3-(heptafluoropropyl)phenyl]methyl][3-[[3-(trifluoromethyl)phenyl]-methoxy]phenyl]amino]-1,1,1-trifluoro-2-propanol;
3-[[[3-(heptafluoropropyl)phenyl]methyl][3-[[3,5-dimethylphenyl]methoxy]-phenyl]amino]-1,1,1-trifluoro-2-propanol;
3-[[[3-(heptafluoropropyl)phenyl]methyl][3-[[3-(trifluoromethylthio)phenyl]-methoxy]phenyl]amino]-1,1,1-trifluoro-2-propanol;
3-[[[3-(heptafluoropropyl)phenyl]methyl](3-[[3,5-difluorophenyl]methoxy]-phenyl]amino]-1,1,1-trifluoro-2-propanol;
3-[[[3-(heptafluoropropyl)phenyl]methyl][3-[cyclohexylmethoxy]phenyl]-amino]-1,1,1-trifluoro-2-propanol;
3-[[3-(2-difluoromethoxy-4-pyridyloxy)phenyl][[3-(heptafluoropropyl)phenyl]-methyl]amino]-1,1,1-trifluoro-2-propanol;
3-[[3-(2-trifluoromethyl-4-pyridyloxy)phenyl][[3-(heptafluoropropyl)phenyl]-methyl]amino]-1,1,1-trifluoro-2-propanol;

3-[[3-(3-difluoromethoxyphenoxy)phenyl][[3-(heptafluoropropyl)phenyl]-methyl]amino]-1,1,1-trifluoro-2-propanol;
3-[[[3-(3-trifluoromethylthio)phenoxy]phenyl][[3-(heptafluoropropyl)phenyl]-methyl]amino]-1,1,1-trifluoro-2-propanol;
3-[[3-(4-chloro-3-trifluoromethylphenoxy)phenyl][[3-(heptafluoropropyl)-phenyl]-methyl]amino]-1,1,1-trifluoro-2-propanol;
3-[[3-(3-trifluoromethoxyphenoxy)phenyl][[2-fluoro-5-(trifluoromethyl)-phenyl]-methyl]amino]-1,1,1-trifluoro-2-propanol;
3-[[3-(3-isopropylphenoxy)phenyl][[2-fluoro-5-(trifluoromethyl)phenyl]-methyl]amino]-1,1,1-trifluoro-2-propanol;
3-[[3-(3-cyclopropylphenoxy)phenyl][[2-fluoro-5-(trifluoromethyl)phenyl]-methyl]amino]-1,1,1-trifluoro-2-propanol;
3-[[3-(3-(2-furyl)phenoxy)phenyl][[2-fluoro-5-(trifluoromethyl)phenyl]-methyl]amino]-1,1,1-trifluoro-2-propanol;
3-[[3-(2,3-dichlorophenoxy)phenyl][[2-fluoro-5-(trifluoromethyl)phenyl]-methyl]amino]-1,1,1-trifluoro-2-propanol;
3-[[3-(4-fluorophenoxy)phenyl][[2-fluoro-5-(trifluoromethyl)phenyl]-methyl]amino]-1,1,1-trifluoro-2-propanol;
3-[[3-(4-methylphenoxy)phenyl][[2-fluoro-5-(trifluoromethyl)phenyl]-methyl]amino]-1,1,1-trifluoro-2-propanol;
3-[[3-(2-fluoro-5-bromophenoxy)phenyl][[2-fluoro-5-(trifluoromethyl)-phenyl]methyl]amino]-1,1,1-trifluoro-2-propanol;
3-[[3-(4-chloro-3-ethylphenoxy)phenyl][[2-fluoro-5-(trifluoromethyl)-phenyl]methyl]amino]-1,1,1-trifluoro-2-propanol;
3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;
3-[[3-[3-(pentafluoroethyl)phenoxy]phenyl][[2-fluoro-5-(trifluoromethyl)-phenyl]-methyl]amino]-1,1,1-trifluoro-2-propanol;
3-[[3-(3,5-dimethylphenoxy)phenyl][[2-fluoro-5-(trifluoromethyl)phenyl]-methyl]amino]-1,1,1-trifluoro-2-propanol;
3-[[3-(3-ethylphenoxy)phenyl][[2-fluoro-5-(trifluoromethyl)phenyl]methyl]-amino]-1,1,1-trifluoro-2-propanol;
3-[[3-(3-t-butylphenoxy)phenyl][[2-fluoro-5-(trifluoromethyl)phenyl]methyl]-amino]-1,1,1-trifluoro-2-propanol;
3-[[3-(3-methylphenoxy)phenyl][[2-fluoro-5-(trifluoromethyl)phenyl]methyl]-amino]-1,1,1-trifluoro-2-propanol;
3-[[3-(5,6,7,8-tetrahydro-2-naphthoxy)phenyl][[2-fluoro-5-(trifluoromethyl)-phenyl]methyl]amino]-1,1,1-trifluoro-2-propanol;
3-[[3-(phenoxy)phenyl][[2-fluoro-5-(trifluoromethyl)phenyl]methyl]amino]-1,1,1-trifluoro-2-propanol;
3-[[3-[3-(N,N-dimethylamino)phenoxy]phenyl][[2-fluoro-5-(trifluoromethyl)-phenyl]methyl]amino]-1,1,1-trifluoro-2-propanol;
3-[[[2-fluoro-5-(trifluoromethyl)phenyl]methyl][3-[[3-(trifluoromethoxy)-phenyl]methoxy]phenyl]amino]-1,1,1-trifluoro-2-propanol;
3-[[[2-fluoro-5-(trifluoromethyl)phenyl]methyl][3-[[3-(trifluoromethyl)-phenyl]methoxy]phenyl]amino]-1,1,1-trifluoro-2-propanol;
3-[[[2-fluoro-5-(trifluoromethyl)phenyl]methyl][3-[[3,5-dimethylphenyl]-methoxy]phenyl]amino]-1,1,1-trifluoro-2-propanol;
3-[[[2-fluoro-5-(trifluoromethyl)phenyl]methyl][3-[[3-(trifluoromethylthio)-phenyl]methoxy]phenyl]amino]-1,1,1-trifluoro-2-propanol;
3-[[[2-fluoro-5-(trifluoromethyl)phenyl]methyl][3-[[3,5-difluorophenyl]-methoxy]phenyl]amino]-1,1,1-trifluoro-2-propanol;
3-[[[2-fluoro-5-(trifluoromethyl)phenyl]methyl][3-[cyclohexylmethoxy]-phenyl]amino]-1,1,1-trifluoro-2-propanol;
3-[[3-(2-difluoromethoxy-4-pyridyloxy)phenyl][[2-fluoro-5-(trifluoromethyl)-phenyl]methyl]amino]-1,1,1-trifluoro-2-propanol;
3-[[3-(2-trifluoromethyl-4-pyridyloxy)phenyl][[2-fluoro-5-(trifluoromethyl)-phenyl]methyl]amino]-1,1,1-trifluoro-2-propanol;
3-[[3-(3-difluoromethoxyphenoxy)phenyl][[2-fluoro-5-(trifluoromethyl)-phenyl]methyl]amino]-1,1,1-trifluoro-2-propanol;
3-[[[3-(3-trifluoromethylthio)phenoxy]phenyl][[2-fluoro-5-(trifluoromethyl)-phenyl]methyl]amino]-1,1,1-trifluoro-2-propanol;
3-[[3-(4-chloro-3-trifluoromethylphenoxy)phenyl][[2-fluoro-5-(trifluoromethyl)phenyl]methyl]amino]-1,1,1-trifluoro-2-propanol;
3-[[3-(3-trifluoromethoxyphenoxy)phenyl][[2-fluoro-4-(trifluoromethyl)-phenyl]methyl]amino]-1,1,1-trifluoro-2-propanol;
3-[[3-(3-isopropylphenoxy)phenyl][[2-fluoro-4-(trifluoromethyl)phenyl]-methyl]amino]-1,1,1-trifluoro-2-propanol;
3-[[3-(3-cyclopropylphenoxy)phenyl][[2-fluoro-4-(trifluoromethyl)phenyl]-methyl]amino]-1,1,1-trifluoro-2-propanol;
3-[[3-(3-(2-furyl)phenoxy)phenyl][[2-fluoro-4-(trifluoromethyl)phenyl]-methyl]amino]-1,1,1-trifluoro-2-propanol;
3-[[3-(2,3-dichlorophenoxy)phenyl][[2-fluoro-4-(trifluoromethyl)phenyl]-methyl]amino]-1,1,1-trifluoro-2-propanol;
3-[[3-(4-fluorophenoxy)phenyl][[2-fluoro-4-(trifluoromethyl)phenyl]-methyl]amino]-1,1,1-trifluoro-2-propanol;
3-[[3-(4-methylphenoxy)phenyl][[2-fluoro-4-(trifluoromethyl)phenyl]-methyl]amino]-1,1,1-trifluoro-2-propanol;
3-[[3-(2-fluoro-5-bromophenoxy)phenyl][[2-fluoro-4-(trifluoromethyl)-phenyl]methyl]amino]-1,1,1-trifluoro-2-propanol;
3-[[3-(4-chloro-3-ethylphenoxy)phenyl][[2-fluoro-4-(trifluoromethyl)-phenyl]methyl]amino]-1,1,1-trifluoro-2-propanol;
3-[[3-[3-(1,1,2,2-tetrafluoroethoxy)phenoxy]phenyl][[2-fluoro-4-(trifluoro-methyl)phenyl]methyl]amino]-1,1,1-trifluoro-2-propanol;
3-[[3-[3-(pentafluoroethyl)phenoxy]phenyl][[2-fluoro-4-(trifluoromethyl)-phenyl]-methyl]amino]-1,1,1-trifluoro-2-propanol;
3-[[3-(3,5-dimethylphenoxy)phenyl][[2-fluoro-4-(trifluoromethyl)phenyl]-methyl]amino]-1,1,1-trifluoro-2-propanol;
3-[[3-(3-ethylphenoxy)phenyl][[2-fluoro-4-(trifluoromethyl)phenyl]methyl]-amino]-1,1,1-trifluoro-2-propanol;
3-[[3-(3-t-butylphenoxy)phenyl][[2-fluoro-4-(trifluoromethyl)phenyl]methyl]-amino]-1,1,1-trifluoro-2-propanol;
3-[[3-(3-methylphenoxy)phenyl][[2-fluoro-4-(trifluoromethyl)phenyl]methyl]-amino]-1,1,1-trifluoro-2-propanol;
3-[[3-(5,6,7,8-tetrahydro-2-naphthoxy)phenyl][[2-fluoro-4-(trifluoromethyl)-phenyl]methyl]amino]-1,1,1-trifluoro-2-propanol;
3-[[3-(phenoxy)phenyl][[2-fluoro-4-(trifluoromethyl)phenyl]methyl]amino]-1,1,1-trifluoro-2-propanol;
3-[[3-[3-(N,N-dimethylamino)phenoxy]phenyl][[2-fluoro-4-(trifluoromethyl)-phenyl]methyl]amino]-1,1,1-trifluoro-2-propanol;

3-[[[2-fluoro-4-(trifluoromethyl)phenyl]methyl][3-[[3-(trifluoromethoxy)-phenyl]methoxy]phenyl]amino]-1,1,1-trifluoro-2-propanol;

3-[[[2-fluoro-4-(trifluoromethyl)phenyl]methyl][3-[[3-(trifluoromethyl)-phenyl]methoxy]phenyl]amino]-1,1,1-trifluoro-2-propanol;

3-[[[2-fluoro-4-(trifluoromethyl)phenyl]methyl][3-[[3,5-dimethylphenyl]-methoxy]phenyl]amino]-1,1,1-trifluoro-2-propanol;

3-[[[2-fluoro-4-(trifluoromethyl)phenyl]methyl][3-[[3-(trifluoromethylthio)-phenyl]methoxy]phenyl]amino]-1,1,1-trifluoro-2-propanol;

3-[[[2-fluoro-4-(trifluoromethyl)phenyl]methyl][3-[[3,5-difluorophenyl]-methoxy]phenyl]amino]-1,1,1-trifluoro-2-propanol;

3-[[[2-fluoro-4-(trifluoromethyl)phenyl]methyl][3-[cyclohexylmethoxy]-phenyl]amino]-1,1,1-trifluoro-2-propanol;

3-[[3-(2-difluoromethoxy-4-pyridyloxy)phenyl][[2-fluoro-4-(trifluoromethyl)-phenyl]methyl]amino]-1,1,1-trifluoro-2-propanol;

3-[[3-(2-trifluoromethyl-4-pyridyloxy)phenyl][[2-fluoro-4-(trifluoromethyl)-phenyl]methyl]amino]-1,1,1-trifluoro-2-propanol;

3-[[3-(3-difluoromethoxyphenoxy)phenyl][[2-fluoro-4-(trifluoromethyl)-phenyl]methyl]amino]-1,1,1-trifluoro-2-propanol;

3-[[[3-(3-trifluoromethylthio)phenoxy)phenyl][[2-fluoro-4-(trifluoromethyl)-phenyl]methyl]amino]-1,1,1-trifluoro-2-propanol; and 3-[[3-(4-chloro-3-trifluoromethylphenoxy)phenyl][[2-fluoro-4-(trifluoro-methyl)phenyl]methyl]amino]-1,1,1-trifluoro-2-propanol.

Another class of CETP inhibitors that finds utility with the present invention consists of substituted N-Aliphatic-N-Aromatic tertiary-Heteroalkylamines having the Formula XV

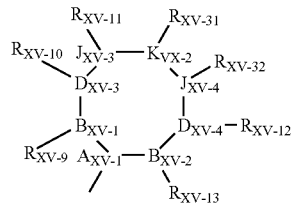

Formula XV and pharmaceutically acceptable forms thereof, wherein:

$n_{XV}$ is an integer selected from 1 through 2;

$A_{XV}$ and $Q_{XV}$ are independently selected from the group consisting of

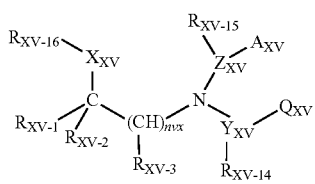

AQ-1 and

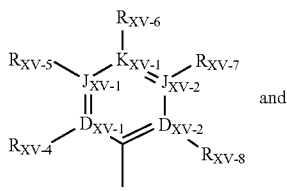

AQ-2

—CH$_2$(CR$_{XV\text{-}37}$R$_{XV\text{-}38}$)$_{vXV}$—(CR$_{XV\text{-}33}$R$_{XV\text{-}34}$)$_{uXV}$-T$_{XV}$—(CR$_{XV\text{-}35}$R$_{XV\text{-}36}$)$_{wXV}$—H, with the provisos that one of $A_{XV}$ and $Q_{XV}$ must be AQ-1 and that one of $A_{XV}$ and $Q_{XV}$ must be selected from the group consisting of AQ-2 and —CH$_2$(CR$_{XV\text{-}37}$R$_{XV\text{-}38}$)$_{vXV}$—(CR$_{XV\text{-}33}$R$_{XV\text{-}34}$)$_{uXV}$-T$_{XV}$-(CR$_{XV\text{-}35}$R$_{XV\text{-}36}$)$_{wXV}$—H;

$T_{XV}$ is selected from the group consisting of a single covalent bond, O, S, S(O), S(O)$_2$, C(R$_{XV\text{-}33}$)═C(R$_{XV\text{-}35}$), and C≡C;

$_{vXV}$ is an integer selected from 0 through 1 with the proviso that $_{vXV}$ is 1 when any one of R$_{XV\text{-}33}$, R$_{XV\text{-}34}$, R$_{XV\text{-}35}$, and R$_{XV\text{-}36}$ is aryl or heteroaryl;

$_{uXV}$ and $_{wXV}$ are integers independently selected from 0 through 6;

$A_{XV\text{-}1}$ is C(R$_{XV\text{-}30}$);

$D_{XV\text{-}1}$ $D_{XV\text{-}2}$, $J_{XV\text{-}1}$, $J_{XV\text{-}2}$, and $K_{XV\text{-}1}$ are independently selected from the group consisting of C, N, O, S and a covalent bond with the provisos that no more than one of $D_{XV\text{-}1}$. $D_{XV\text{-}2}$, $J_{XV\text{-}1}$, $J_{XV\text{-}2}$, and $K_{XV\text{-}1}$ is a covalent bond, no more than one of $D_{XV\text{-}1}$, $D_{XV\text{-}2}$, $J_{XV\text{-}1}$, $J_{XV\text{-}2}$, and $K_{XV\text{-}1}$ is O, no more than one of $D_{XV\text{-}1}$, $D_{XV\text{-}2}$, $J_{XV\text{-}1}$, $J_{XV\text{-}2}$, and $K_{XV\text{-}1}$ is S, one of $D_{XV\text{-}1}$, $D_{XV\text{-}2}$, $J_{XV\text{-}1}$, $J_{XV\text{-}2}$, and $K_{XV\text{-}1}$ must be a covalent bond when two of $D_{XV\text{-}1}$, $D_{XV\text{-}2}$, $J_{XV\text{-}1}$, $J_{XV\text{-}2}$, and $K_{XV\text{-}1}$ are O and S, and no more than four of $D_{XV\text{-}1}$, $D_{XV\text{-}2}$, $J_{XV\text{-}1}$, $J_{XV\text{-}2}$, and $K_{XV\text{-}1}$ are N;

$B_{XV\text{-}1}$, $B_{XV\text{-}2}$, $D_{XV\text{-}3}$, $D_{XV\text{-}4}$, $J_{XV\text{-}3}$, $J_{XV\text{-}4}$ and $K_{XV\text{-}2}$ are independently selected from the group consisting of C, C(R$_{XV\text{-}30}$), N, O, S and a covalent bond with the provisos that no more than 5 of $B_{XV\text{-}1}$, $B_{XV\text{-}2}$, $D_{XV\text{-}3}$, $D_{XV\text{-}4}$, $J_{XV\text{-}3}$, $J_{XV\text{-}4}$, and $K_{XV\text{-}2}$ are a covalent bond, no more than two of $B_{XV\text{-}1}$, $B_{XV\text{-}2}$, $D_{XV\text{-}3}$, $D_{XV\text{-}4}$, $J_{XV\text{-}3}$, $J_{XV\text{-}4}$, and $K_{XV\text{-}2}$ are 0, no more than two of $B_{XV\text{-}1}$, $B_{XV\text{-}2}$, $D_{XV\text{-}3}$, $D_{XV\text{-}4}$ $J_{XV\text{-}3}$, $J_{XV\text{-}4}$, and $K_{XV\text{-}2}$ are S, no more than two of $B_{XV\text{-}1}$, $B_{XV\text{-}2}$, $D_{XV\text{-}3}$, $D_{XV\text{-}4}$, $J_{XV\text{-}3}$, $J_{XV\text{-}4}$, and $K_{XV\text{-}2}$ are simultaneously O and S, and no more than two of $B_{XV\text{-}1}$, $B_{XV\text{-}2}$, $D_{XV\text{-}3}$, $D_{XV\text{-}4}$, $J_{XV\text{-}3}$, $J_{XV\text{-}4}$, and $K_{XV\text{-}2}$ are N;

$B_{XV\text{-}1}$ and $D_{XV\text{-}3}$, $D_{XV\text{-}3}$ and $J_{XV\text{-}3}$, $J_{XV\text{-}3}$ and $K_{XV\text{-}2}$, $K_{XV\text{-}2}$ and $J_{XV\text{-}4}$, $J_{XV\text{-}4}$ and $D_{XV\text{-}4}$, and $D_{XV\text{-}4}$ and $B_{XV\text{-}2}$ are independently selected to form an in-ring spacer pair wherein said spacer pair is selected from the group consisting of C(R$_{XV\text{-}33}$)═C(R$_{XV\text{-}35}$) and N═N with the provisos that AQ-2 must be a ring of at least five contiguous members, that no more than two of the group of said spacer pairs are simultaneously C(R$_{XV\text{-}33}$)═C(R$_{XV\text{-}35}$) and that no more than one of the group of said spacer pairs can be N═N unless the other spacer pairs are other than C(R$_{XV\text{-}33}$)═C(R$_{XV\text{-}35}$), O, N, and S;

$R_{XV\text{-}1}$ is selected from the group consisting of haloalkyl and haloalkoxymethyl;

$R_{XV\text{-}2}$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl and heteroaryl;

$R_{XV-3}$ is selected from the group consisting of hydrido, aryl, alkyl, alkenyl, haloalkyl, and haloalkoxyalkyl;

$Y_{XV}$ is selected from the group consisting of a covalent single bond, $(CH_2)_q$ wherein q is an integer selected from 1 through 2 and $(CH_2)_j$—O—$(CH_2)_k$ wherein j and k are integers independently selected from 0 through 1;

$Z_{XV}$ is selected from the group consisting of covalent single bond, $(CH_2)_q$ wherein q is an integer selected from 1 through 2, and $(CH_2)_j$—O—$(CH_2)_k$ wherein j and k are integers independently selected from 0 through 1;

$R_{xv-4}$, $R_{xv-8}$, $R_{xv-9}$ and $R_{xv-13}$ are independently selected from the group consisting of hydrido, halo, haloalkyl, and alkyl;

$R_{XV-30}$ is selected from the group consisting of hydrido, alkoxy, alkoxyalkyl, halo, haloalkyl, alkylamino, alkylthio, alkylthioalkyl, alkyl, alkenyl, haloalkoxy, and haloalkoxyalkyl with the proviso that $R_{xv-30}$ is selected to maintain the tetravalent nature of carbon, trivalent nature of nitrogen, the divalent nature of sulfur, and the divalent nature of oxygen;

$R_{XV-30}$, when bonded to $A_{XV-1}$, is taken together to form an intra-ring linear spacer connecting the $A_{XV-1}$-carbon at the point of attachment of $R_{XV-30}$ to the point of bonding of a group selected from the group consisting of $R_{XV-10}$, $R_{XV-11}$, $R_{XV-12}$, $R_{XV-31}$, and $R_{XV-32}$ wherein said intra-ring linear spacer is selected from the group consisting of a covalent single bond and a spacer moiety having from 1 through 6 contiguous atoms to form a ring selected from the group consisting of a cycloalkyl having from 3 through 10 contiguous members, a cycloalkenyl having from 5 through 10 contiguous members, and a heterocyclyl having from 5 through 10 contiguous members;

$R_{XV-30}$, when bonded to $A_{XV-1}$, is taken together to form an intra-ring branched spacer connecting the $A_{XV-1}$-carbon at the point of attachment of $R_{XV-30}$ to the points of bonding of each member of any one of substituent pairs selected from the group consisting of substituent pairs $R_{XV-10}$ and $R_{XV-11}$, $R_{XV-10}$ and $R_{XV-31}$, $R_{XV-10}$ and $R_{XV-32}$, $R_{XV-10}$ and $R_{XV}$-12, $R_{XV-11}$ and $R_{XV-31}$, $R_{XV-11}$ and $R_{XV-32}$, $R_{XV-11}$ and $R_{XV}$-12, $R_{XV-31}$ and $R_{XV-32}$, $R_{XV-31}$ and $R_{XV-12}$, and $R_{XV-32}$ and $R_{XV-12}$ and wherein said intra-ring branched spacer is selected to form two rings selected from the group consisting of cycloalkyl having from 3 through 10 contiguous members, cycloalkenyl having from 5 through 10 contiguous members, and heterocyclyl having from 5 through 10 contiguous members;

$R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$, and $R_{XV-36}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkylamidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydroxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, alkylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the provisos that $R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$ and $R_{XV-36}$ are each independently selected to maintain the tetravalent nature of carbon, trivalent nature of nitrogen, the divalent nature of sulfur, and the divalent nature of oxygen, that no more than three of the $R_{XV-33}$ and $R_{XV-34}$ substituents are simultaneously selected from other than the group consisting of hydrido and halo, and that no more than three of the $R_{XV-35}$ and $R_{XV-36}$ substituents are simultaneously selected from other than the group consisting of hydrido and halo;

$R_{XV-9}$, $R_{XV-10}$, $R_{XV-11}$, $R_{XV-12}$, $R_{XV-13}$, $R_{XV-31}$, and $R_{XV-32}$ are independently selected to be oxo with the provisos that $B_{XV-1}$, $B_{XV-2}$, $D_{XV-3}$, $D_{XV-4}$, $J_{XV-3}$, $J_{XV-4}$, and $K_{XV-2}$ are independently selected from the group consisting of C and S, no more than two of $R_{XV-9}$, $R_{XV-10}$, $R_{XV-11}$, $R_{XV-12}$, $R_{XV-13}$, $R_{XV-31}$, and $R_{XV-32}$ are simultaneously oxo, and that $R_{XV-9}$, $R_{XV-10}$, $R_{XV-11}$, $R_{XV-12}$, $R_{XV-13}$, $R_{XV-31}$ and $R_{XV-32}$ are each independently selected to maintain the tetravalent nature of carbon, trivalent nature of nitrogen, the divalent nature of sulfur, and the divalent nature of oxygen;

$R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$, $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$ is used at the same time and that no more than one of the group consisting of spacer pairs $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are used at the same time;

$R_{XV-9}$ and $R_{XV-11}$, $R_{XV-9}$ and $R_{XV-12}$, $R_{XV-9}$ and $R_{XV-13}$ $R_{XV-9}$ and $R_{XV-31}$, $R_{XV-9}$ and $R_{XV-32}$, $R_{XV-10}$ and $R_{XV-12}$, $R_{XV-10}$ and $R_{XV-13}$, $R_{XV-10}$ and $R_{XV-31}$, $R_{XV-10}$ and $R_{XV-32}$, $R_{XV-11}$ and $R_{XV-12}$, $R_{XV-11}$ and $R_{XV-13}$, $R_{XV-11}$ and $R_{XV-32}$, $R_{XV-12}$ and $R_{XV-31}$, $R_{XV-13}$ and $R_{XV-31}$, and $R_{XV-13}$ and $R_{XV-32}$ are independently selected to form a spacer pair wherein said spacer pair is taken together to form a linear spacer moiety selected from the group consisting of a covalent single bond and a moiety having from 1 through 3 contiguous atoms to form a ring selected from the group consisting of a cycloalkyl having from 3 through 8 contiguous members, a cycloalkenyl having from 5 through 8 contiguous members, a saturated heterocyclyl having from 5 through 8 contiguous members and a partially saturated heterocyclyl having from 5 through 8 contiguous members with the provisos that no more than one of said group of spacer pairs is used at the same time;

$R_{XV-37}$ and $R_{XV-38}$ are independently selected from the group consisting of hydrido, alkoxy, alkoxyalkyl, hydroxy, amino, thio, halo, haloalkyl, alkylamino, alkylthio, alkylthioalkyl, cyano, alkyl, alkenyl, haloalkoxy, and haloalkoxyalkyl.

Compounds of Formula XV and their methods of manufacture are disclosed in PCT Publication No. WO 00/18723, which is incorporated herein by reference in its entirety for all purposes.

In a preferred embodiment, the CETP inhibitor is selected from the following compounds of Formula XV:

3-[[3-(4-chloro-3-ethylphenoxy)phenyl](cyclohexylmethyl)amino]-1,1,1-trifluoro-2-propanol;
3-[[3-(4-chloro-3-ethylphenoxy)phenyl](cyclopentylmethyl)amino]-1,1,1-trifluoro-2-propanol;
3-[[3-(4-chloro-3-ethylphenoxy)phenyl](cyclopropylmethyl)amino]-1,1,1-trifluoro-2-propanol;
3-[[3-(4-chloro-3-ethylphenoxy)phenyl][(3-trifluoromethyl)cyclohexyl-methyl]amino]-1,1,1-trifluoro-2-propanol;
3-[[3-(4-chloro-3-ethylphenoxy)phenyl][(3-pentafluoroethyl)cyclohexyl-methyl]amino]-1,1,1-trifluoro-2-propanol;
3-[[3-(4-chloro-3-ethylphenoxy)phenyl][(3-trifluoromethoxy)cyclohexyl-methyl]amino]-1,1,1-trifluoro-2-propanol;
3-[[3-(4-chloro-3-ethylphenoxy)phenyl][3-(1,1,2,2-tetrafluoroethoxy)cyclo-hexylmethyl]amino]-1,1,1-trifluoro-2-propanol;
3-[[3-(3-trifluoromethoxyphenoxy)phenyl](cyclohexylmethyl)amino]-1,1,1-trifluoro-2-propanol;
3-[[3-(3-trifluoromethoxyphenoxy)phenyl](cyclopentylmethyl)amino]-1,1,1-trifluoro-2-propanol;
3-[[3-(3-trifluoromethoxyphenoxy)phenyl](cyclopropylmethyl)amino]-1,1,1-trifluoro-2-propanol;
3-[[3-(3-trifluoromethoxyphenoxy)phenyl][(3-trifluoromethyl)cyclohexyl-methyl]amino]-1,1,1-trifluoro-2-propanol;
3-[[3-(3-trifluoromethoxyphenoxy)phenyl][(3-pentafluoroethyl)cyclohexyl-methyl]amino]-1,1,1-trifluoro-2-propanol;
3-[[3-(3-trifluoromethoxyphenoxy)phenyl][(3-trifluoromethoxy)cyclohexyl-methyl]amino]-1,1,1-trifluoro-2-propanol;
3-[[3-(3-trifluoromethoxyphenoxy)phenyl][3-(1,1,2,2-tetrafluoroethoxy)cyclohexyl-methyl]amino]-1,1,1-trifluoro-2-propanol;
3-[[3-(3-isopropylphenoxy)phenyl](cyclohexylmethyl)amino]-1,1,1-trifluoro-2-propanol;
3-[[3-(3-isopropylphenoxy)phenyl](cyclopentylmethyl)amino]-1,1,1-trifluoro-2-propanol;
3-[[3-(3-isopropylphenoxy)phenyl](cyclopropylmethyl)amino]-1,1,1-trifluoro-2-propanol;
3-[[3-(3-isopropylphenoxy)phenyl][(3-trifluoromethyl)cyclohexyl-methyl]amino]-1,1,1-trifluoro-2-propanol;
3-[[3-(3-isopropylphenoxy)phenyl][(3-pentafluoroethyl)cyclohexyl-methyl]amino]-1,1,1-trifluoro-2-propanol;
3-[[3-(3-isopropylphenoxy)phenyl][(3-trifluoromethoxy)cyclohexyl-methyl]amino]-1,1,1-trifluoro-2-propanol;
3-[[3-(3-isopropylphenoxy)phenyl][3-(1,1,2,2-tetrafluoroethoxy)cyclohexyl-methyl]amino]-1,1,1-trifluoro-2-propanol;
3-[[3-(2,3-dichlorophenoxy)phenyl](cyclohexylmethyl)amino]-1,1,1-trifluoro-2-propanol;
3-[[3-(2,3-dichlorophenoxy)phenyl](cyclopentylmethyl)amino]-1,1,1-trifluoro-2-propanol;
3-[[3-(2,3-dichlorophenoxy)phenyl](cyclopropylmethy)amino]-1,1,1-trifluoro-2-propanol;
3-[[3-(2,3-dichlorophenoxy)phenyl][(3-trifluoromethyl)cyclohexyl-methyl]amino]-1,1,1-trifluoro-2-propanol;
3-[[3-(2,3-dichlorophenoxy)phenyl][(3-pentafluoroethyl)cyclohexyl-methyl]amino]-1,1,1-trifluoro-2-propanol;
3-[[3-(2,3-dichlorophenoxy)phenyl][(3-trifluoromethoxy)cyclohexyl-methyl]amino]-1,1,1-trifluoro-2-propanol;
3-[[3-(2,3-dichlorophenoxy)phenyl][3-(1,1,2,2-tetrafluoroethoxy)cyclo-hexyl-methyl]amino]-1,1,1-trifluoro-2-propanol;
3-[[3-(4-fluorophenoxy)phenyl](cyclohexylmethyl)amino]-1,1,1-trifluoro-2-propanol;
3-[[3-(4-fluorophenoxy)phenyl](cyclopentylmethyl)amino]-1,1,1-trifluoro-2-propanol;
3-[[3-(4-fluorophenoxy)phenyl](cyclopropylmethyl)amino]-1,1,1-trifluoro-2-propanol;
3-[[3-(4-fluorophenoxy)phenyl][(3-trifluoromethyl)cyclohexyl-methyl]amino]-1,1,1-trifluoro-2-propanol;
3-[[3-(4-fluorophenoxy)phenyl][(3-pentafluoroethyl)cyclohexyl-methyl]amino]-1,1,1-trifluoro-2-propanol;
3-[[3-(4-fluorophenoxy)phenyl][(3-trifluoromethoxy)cyclohexyl-methyl]amino]-1,1,1-trifluoro-2-propanol;
3-[[3-(4-fluorophenoxy)phenyl][3-(1,1,2,2-tetrafluoroethoxy)cyclohexyl-methyl]amino]-1,1,1-trifluoro-2-propanol;
3-[[3-(3-trifluoromethoxybenzyloxy]phenyl](cyclohexylmethyl)amino]-1,1,1-trifluoro-2-propanol;
3-[[3-(3-trifluoromethoxybenzyloxy)phenyl](cyclopentylmethyl)amino]-1,1,1-trifluoro-2-propanol;
3-[[3-(3-trifluoromethoxybenzyloxy)phenyl](cyclopropylmethyl)amino]-1,1,1-trifluoro-2-propanol;
3-[[3-(3-trifluoromethoxybenzyloxy)phenyl][(3-trifluoromethyl)cyclohexyl-methyl]amino]-1,1,1-trifluoro-2-propanol;
3-[[3-(3-trifluoromethoxybenzyloxy)phenyl][(3-pentafluoroethyl)cyclohexyl-methyl]amino]-1,1,1-trifluoro-2-propanol;

3-[[3-(3-trifluoromethoxybenzyloxy]phenyl][(3-trifluoromethoxy)cyclohexyl-methyl]amino]-1,1,1-trifluoro-2-propanol;

3-[[3-(3-trifluoromethoxybenzyloxy)phenyl][3-(1,1,2,2-tetrafluoroethoxy)-cyclohexylmethyl]amino]-1,1,1-trifluoro-2-propanol;

3-[[3-(3-trifluoromethylbenzyloxy)phenyl](cyclohexylmethyl)amino]-1,1,1-trifluoro-2-propanol;

3-[[3-(3-trifluoromethylbenzyloxy)phenyl](cyclopentylmethyl)amino]-1,1,1-trifluoro-2-propanol;

3-[[3-(3-trifluoromethylbenzyloxy)phenyl](cyclopropylmethyl)amino]-1,1,1-trifluoro-2-propanol;

3-[[3-(3-trifluoromethylbenzyloxy)phenyl][(3-trifluoromethyl)cyclohexyl-methyl]amino]-1,1,1-trifluoro-2-propanol;

3-[[3-(3-trifluoromethylbenzyloxy)phenyl][(3-pentafluoroethyl)cyclohexyl-methyl]amino]-1,1,1-trifluoro-2-propanol;

3-[[3-(3-trifluoromethylbenzyloxy)phenyl][(3-trifluoromethoxy)cyclohexyl-methyl]amino]-1,1,1-trifluoro-2-propanol;

3-[[3-(3-trifluoromethylbenzyloxy)phenyl][3-(1,1,2,2-tetrafluoroethoxy)cyclohexyl-methyl]amino]-1,1,1-trifluoro-2-propanol;

3-[[[(3-trifluoromethyl)phenyl]methyl](cyclohexyl)amino]-1,1,1-trifluoro-2-propanol;

3-[[[(3-pentafluoroethyl)phenyl]methyl](cyclohexyl)amino]-1,1,1-trifluoro-2-propanol;

3-[[[(3-trifluoromethoxy)phenyl]methyl](cyclohexyl)amino]-1,1,1-trifluoro-2-propanol;

3-[[[3-(1,1,2,2-tetrafluoroethoxy)phenyl]methyl](cyclohexyl)amino]-1,1,1-trifluoro-2-propanol;

3-[[[(3-trifluoromethyl)phenyl]methyl](4-methylcyclohexyl)amino]-1,1,1-trifluoro-2-propanol;

3-[[[(3-pentafluoroethyl)phenyl]methyl](4-methylcyclohexyl)amino]-1,1,1-trifluoro-2-propanol;

3-[[[(3-trifluoromethoxy)phenyl]methyl](4-methylcyclohexyl)amino]-1,1,1-trifluoro-2-propanol;

3-[[[3-(1,1,2,2-tetrafluoroethoxy)phenyl]methyl](4-methylcyclohexyl)amino]-1,1,1-trifluoro-2-propanol;

3-[[[(3-trifluoromethyl)phenyl]methyl](3-trifluoromethylcyclohexyl)amino]-1,1,1-trifluoro-2-propanol;

3-[[[(3-pentafluoroethyl)phenyl]methyl](3-trifluoromethylcyclohexyl)amino]-1,1,1-trifluoro-2-propanol;

3-[[[(3-trifluoromethoxy)phenyl]methyl](3-trifluoromethylcyclohexyl)amino]-1,1,1-trifluoro-2-propanol;

3-[[[3-(1,1,2,2-tetrafluoroethoxy)phenyl]methyl](3-trifluoromethylcyclohexyl)amino]-1,1,1-trifluoro-2-propanol;

3-[[[(3-trifluoromethyl)phenyl]methyl][3-(4-chloro-3-ethylphenoxy)cyclo-hexyl]amino]-1,1,1-trifluoro-2-propanol;

3-[[[(3-pentafluoroethyl)phenyl]methyl][3-(4-chloro-3-ethylphenoxy)cyclo-hexyl]amino]-1,1,1-trifluoro-2-propanol;

3-[[[(3-trifluoromethoxy)phenyl]methyl][3-(4-chloro-3-methylphenoxy)cyclo-hexyl]amino]-1,1,1-trifluoro-2-propanol;

3-[[[3-(1,1,2,2-tetrafluoroethoxy)phenyl]methyl][3-(4-chloro-3-ethylphenoxy)-cyclohexyl]amino]-1,1,1-trifluoro-2-propanol;

3-[[[(3-trifluoromethyl)phenyl]methyl](3-phenoxycyclohexyl)amino]-1,1,1-trifluoro-2-propanol;

3-[[[(3-pentafluoroethyl)phenyl]methyl](3-phenoxycyclohexyl)amino]-1,1,1-trifluoro-2-propanol;

3-[[[(3-trifluoromethoxy)phenyl]methyl](3-phenoxycyclohexyl)amino]-1,1,1-trifluoro-2-propanol;

3-[[[3-(1,1,2,2-tetrafluoroethoxy)phenyl]methyl](3-phenoxycyclohexyl)amino]-1,1,1-trifluoro-2-propanol;

3-[[[(3-trifloromethyl)phenyl]methyl](3-isopropoxycyclohexyl)amino]-1,1,1-trifluoro-2-propanol;

3-[[[(3-pentafluoroethyl)phenyl]methyl](3-isopropoxycyclohexyl)amino]-1,1,1-trifluoro-2-propanol;

3-[[[(3-trifluoromethoxy)phenyl]methyl](3-isopropoxycyclohexyl)amino]-1,1,1-trifluoro-2-propanol;

3-[[[3-(1,1,2,2-tetrafluoroethoxy)phenyl]methyl](3-isopropoxycyclohexyl)-amino]-1,1,1-trifluoro-2-propanol;

3-[[[(3-trifluoromethyl)phenyl]methyl](3-cyclopentyloxycyclohexyl]amino]-1,1,1-trifluoro-2-propanol;

3-[[[(3-pentafluoroethyl)phenyl]methyl](3-cyclopentyloxycyclohexyl)amino]-1,1,1-trifluoro-2-propanol;

3-[[[(3-trifluoromethoxy)phenyl]methyl](3-cyclopentyloxycyclohexyl)amino]-1,1,1-trifluoro-2-propanol;

3-[([3-(1,1,2,2-tetrafluoroethoxy)phenyl]methyl](3-cyclopentyloxycyclohexyl)-amino]-1,1,1-trifluoro-2-propanol;

3-[[[(2-trifluoromethyl)pyrid-6-yl]methyl](3-isopropoxycyclohexyl)amino]-1,1,1-trifluoro-2-propanol;

3-[[[(2-trifluoromethyl)pyrid-6-yl]methyl](3-cyclopentyloxycyclohexyl)-amino]-1,1,1-trifluoro-2-propanol;

3-[[[(2-trifluoromethyl)pyrid-6-yl]methyl](3-phenoxycyclohexyl)amino]-1,1,1-trifluoro-2-propanol;

3-[[[(2-trifluoromethyl)pyrid-6-yl]methyl](3-trifluoromethylcyclohexyl)amino]-1,1,1-trifluoro-2-propanol;

3-[[[(2-trifluoromethyl)pyrid-6-yl]methyl][3-(4-chloro-3-ethylphenoxy)cyclo-hexyl]amino]-1,1,1-trifluoro-2-propanol;

3-[[[(2-trifluoromethyl)pyrid-6-yl]methyl][3-(1,1,2,2-tetrafluoroethoxy)cyclo-hexyl]amino]-1,1,1-trifluoro-2-propanol;

3-[[[(2-trifluoromethyl)pyrid-6-yl]methyl](3-pentafluoroethylcyclohexyl)-amino]-1,1,1-trifluoro-2-propanol;

3-[[[(2-trifluoromethyl)pyrid-6-yl]methyl](3-trifluoromethoxycyclohexyl)-amino]-1,1,1-trifluoro-2-propanol;

3-[[[(3-trifluoromethyl)phenyl]methyl][3-(4-chloro-3-ethylphenoxy)propyl]-amino]-1,1,1-trifluoro-2-propanol;

3-[[[(3-pentafluoroethyl)phenyl]methyl][3-(4-chloro-3-ethylphenoxy)propyl]-amino]-1,1,1-trifluoro-2-propanol;

3-[[[(3-trifluoromethoxy)phenyl]methyl][3-(4-chloro-3-ethylphenoxy)propyl]-amino]-1,1,1-trifluoro-2-propanol;

3-[[[3-(1,1,2,2-tetrafluoroethoxy)phenyl]methyl][3-(4-chloro-3-ethylphenoxy)-propyl]amino]-1,1,1-trifluoro-2-propanol;

3-[[[(3-trifluoromethyl)phenyl]methyl][3-(4-chloro-3-ethylphenoxy)-2,2,-di-fluoropropyl]amino]-1,1,1-trifluoro-2-propanol;

3-[[[(3-pentafluoroethyl)phenyl]methyl][3-(4-chloro-3-ethylphenoxy)-2,2-di-fluropropyl]amino]-1,1,1-trifluoro-2-propanol;

3-[[[(3-trifluoromethoxy)phenyl]methyl][3-(4-chloro-3-ethylphenoxy)-2,2,-di-fluoropropyl]amino]-1,1,1-trifluoro-2-propanol;

3-[[[3-(1,1,2,2-tetrafluoroethoxy)phenyl]methyl][3-(4-chloro-3-ethylphenoxy)-2,2,-difluoropropyl]amino]-1,1,1-trifluoro-2-propanol;

3-[[[(3-trifluoromethyl)phenyl]methyl][3-(isopropoxy)propyl]amino]-1,1,1-trifluoro-2-propanol;

3-[[[(3-pentafluoroethyl)phenyl]methyl][3-(isopropoxy)propyl]amino]-1,1,1-trifluoro-2-propanol;

3-[[[(3-trifluoromethoxy)phenyl]methyl][3-(isopropoxy)propyl]amino]-1,1,1-trifluoro-2-propanol;

3-[[[3-(1,1,2,2-tetrafluoroethoxy)phenyl]methyl][3-(isopropoxy)propyl]amino]-1,1,1-trifluoro-2-propanol; and 3-[[[3-(1,1,2,2-tetrafluoroethoxy)phenyl]methyl][3-(phenoxy)propyl]amino]-1,1,1-trifluoro-2-propanol.

Another class of CETP inhibitors that finds utility with the present invention consists of (R)-chiral halogenated 1-substituted amino-(n+1)-alkanols having the Formula XVI Formula XVI

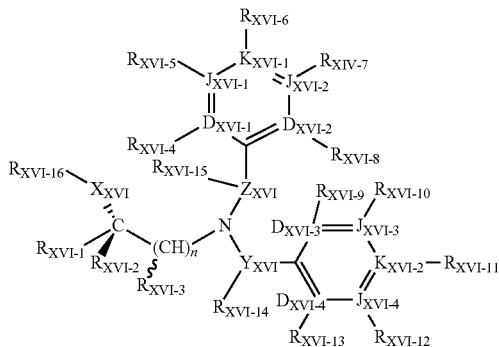

and pharmaceutically acceptable forms thereof, wherein:

$n_{XVI}$ is an integer selected from 1 through 4;

$X_{XVI}$ is oxy;

$R_{XVI-1}$ is selected from the group consisting of haloalkyl, haloalkenyl, haloalkoxymethyl, and haloalkenyloxymethyl with the proviso that $R_{XVI-1}$ has a higher Cahn-Ingold-Prelog stereochemical system ranking than both $R_{XVI-2}$ and $(CHR_{XVI-3})_n$—$N(A_{XVI})Q_{XVI}$ wherein $A_{XVI}$ is Formula XVI-(II) and Q is Formula XVI-(III);

XVI-II

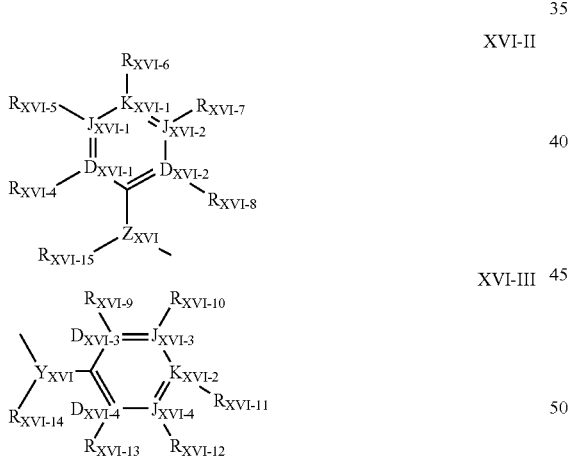

XVI-III $R_{XVI-16}$ is selected from the group consisting of hydrido, alkyl, acyl, aroyl, heteroaroyl, trialkylsilyl, and a spacer selected from the group consisting of a covalent single bond and a linear spacer moiety having a chain length of 1 to 4 atoms linked to the point of bonding of any aromatic substituent selected from the group consisting of $R_{XVI-4}$, $R_{XVI-8}$, $R_{XVI-9}$, and $R_{XVI-13}$ to form a heterocyclyl ring having from 5 through 10 contiguous members;

$D_{XVI-1}$, $D_{XVI-2}$, $J_{XVI-1}$, $J_{XVI-2}$ and $K_{XVI-1}$ are independently selected from the group consisting of C, N, O, S and covalent bond with the provisos that no more than one of $D_{XVI-1}$, $D_{XVI-2}$, $J_{XVI-1}$, $J_{XVI-2}$ and $K_{XVI-1}$ is a covalent bond, no more than one $D_{XVI-1}$, $D_{XVI-2}$, $J_{XVI-1}$, $J_{XVI-2}$ and $K_{XVI-1}$ is be O, no more than one of $D_{XVI-1}$, $D_{XVI-2}$, $J_{XVI-1}$, $J_{XVI-2}$ and $K_{XVI-1}$ is S, one of $D_{XVI-1}$, $D_{XVI-2}$, $J_{XVI-1}$, $J_{XVI-2}$ and $K_{XVI-1}$ must be a covalent bond when two of $D_{XVI-1}$, $D_{XVI-2}$, $J_{XVI-1}$, $J_{XVI-2}$ and $K_{XVI-1}$ are O and S, and no more than four of $D_{XVI-1}$, $D_{XVI-2}$, $J_{XVI-1}$, $J_{XVI-2}$ and $K_{XVI-1}$ is N;

$D_{XVI-3}$, $D_{XVI-4}$, $J_{XVI-3}$, $J_{XVI-4}$ and $K_{XVI-2}$ are independently selected from the group consisting of C, N, O, S and covalent bond with the provisos that no more than one is a covalent bond, no more than one of $D_{XVI-3}$, $D_{XVI-4}$, $J_{XVI-3}$, $J_{XVI-4}$ and $K_{XVI-2}$ is O, no more than one of $D_{XVI-3}$, $D_{XVI-4}$, $J_{XVI-3}$, $J_{XVI-4}$ and $K_{XVI-2}$ is S, no more than two of $D_{XVI-3}$, $D_{XVI-4}$, $J_{XVI-3}$, $J_{XVI-4}$ and $K_{XVI-2}$ is O and S, one of $D_{XVI-3}$, $D_{XVI-4}$, $J_{XVI-3}$, $J_{XVI-4}$ and $K_{XVI-2}$ must be a covalent bond when two of $D_{XVI-3}$, $D_{XVI-4}$, $J_{XVI-3}$, $J_{XVI-4}$ and $K_{XVI-2}$ are O and S, and no more than four of $D_{XVI-3}$, $D_{XVI-4}$, $J_{XVI-3}$, $J_{XVI-4}$ and $K_{XVI-2}$ are N;

$R_{XVI-2}$ is selected from the group consisting of hydrido, aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl, with the proviso that $R_{XVI-2}$ has a lower Cahn-Ingold-Prelog system ranking than both $R_{XVI-1}$ and $(CHR_{XVI-3})_n$—$N(A_{XVI})Q_{XVI}$;

$R_{XVI-3}$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl, with the provisos that $(CHR_{XVI-3})_n$—$N(A_{XVI})Q_{XVI}$ has a lower Cahn-Ingold-Prelog stereochemical system ranking than $R_{XVI-1}$ and a higher Cahn-Ingold-Prelog stereochemical system ranking than $R_{XVI-2}$;

$Y_{XVI}$ is selected from a group consisting of a covalent single bond, $(C(R_{XVI-14})_2)_q$ wherein q is an integer selected from 1 and 2 and $(CH(R_{XVI-14}))_g$—$W_{XVI}$—$(CH(R_{XVI-14}))_p$ wherein g and p are integers independently selected from 0 and 1;

$R_{XVI-14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$Z_{XVI}$ is selected from a group consisting of a covalent single bond, $(C(R_{XVI-15})_2)_q$, wherein q is an integer selected from 1 and 2, and $(CH(R_{XVI-15}))_j$—$W_{XVI}$—$(CH(R_{XVI-15}))_k$ wherein j and k are integers independently selected from 0 and 1;

$W_{XVI}$ is selected from the group consisting of O, C(O), C(S), C(O)N($R_{XVI-14}$), C(S)N($R_{XVI-14}$), ($R_{XVI-14}$)NC(O), ($R_{XVI-14}$)NC(S), S, S(O), S(O)$_2$, S(O)$_2$N($R_{XVI-14}$), ($R_{XVI-14}$)NS(O)$_2$, and N($R_{XVI-14}$) with the proviso that $R_{XVI-14}$ is other than cyano;

$R_{XVI-15}$ is selected, from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkyl, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl, amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydroxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that $R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are each independently selected to maintain the tetravalent nature of carbon, trivalent nature of nitrogen, the divalent nature of sulfur, and the divalent nature of oxygen;

$R_{XVI-4}$ and $R_{XVI-5}$, $R_{XVI-5}$ and $R_{XVI-6}$, $R_{XVI-6}$ and $R_{XVI-7}$, $R_{XVI-7}$ and $R_{XVI-8}$, $R_{XVI-9}$ and $R_{XVI-10}$, $R_{XVI-10}$ and $R_{XVI-11}$, $R_{XVI-11}$ and $R_{XVI-12}$, and $R_{XVI-12}$ and $R_{XIV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XVI-4}$ and $R_{XVI-5}$, $R_{XVI-5}$ and $R_{XVI-6}$, $R_{XVI-6}$ and $R_{XVI-7}$, and $R_{XVI-7}$ and $R_{XVI-8}$ is used at the same time and that no more than one of the group consisting of spacer pairs $R_{XIV-9}$ and $R_{XVI-10}$, $R_{XVI-10}$ and $R_{XVI-11}$, $R_{XVI-11}$ and $R_{XVI-12}$, and $R_{XVI-12}$ and $R_{XVI-13}$ can be used at the same time;

$R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is used at the same time.

Compounds of Formula XVI and their methods of manufacture are disclosed in PCT Publication No. WO 00/18724, which is incorporated herein by reference in its entirety for all purposes.

In a preferred embodiment, the CETP inhibitor is selected from the following compounds of Formula XVI:

(2R)-3-[[3-(3-trifluoromethoxyphenoxy)phenyl][[3-(1,1,2,2-tetrafluoroethoxy)phenyl]methyl]amino]-1,1,1-trifluoro-2-propanol;

(2R)-3-[[3-(3-isopropylphenoxy)phenyl][[3-(1,1,2,2-tetrafluoroethoxy)phenyl]-methyl]amino]-1,1,1-trifluoro-2-propanol;

(2R)-3-[[3-(3-cyclopropylphenoxy)phenyl][[3-(1,1,2,2-tetrafluoroethoxy)phenyl]-methyl]amino]-1,1,1-trifluoro-2-propanol;

(2R)-3-[[3-(3-(2-furyl)phenoxy)phenyl][[3-(1,1,2,2-tetrafluoroethoxy)phenyl]-methyl]amino]-1,1,1-trifluoro-2-propanol;

(2R)-3-[[3-(2,3-dichlorophenoxy)phenyl][[3-(1,1,2,2-tetrafluoroethoxy)phenyl]-methyl]amino]-1,1,1-trifluoro-2-propanol;

(2R)-3-[[3-(4-fluorophenoxy)phenyl][[3-(1,1,2,2-tetrafluoroethoxy)phenyl]-methyl]amino]-1,1,1-trifluoro-2-propanol;

(2R)-3-[[3-(4-methylphenoxy)phenyl][[3-(1,1,2,2-tetrafluoroethoxy)phenyl]-methyl]amino]-1,1,1-trifluoro-2-propanol;

(2R)-3-[[3-(2-fluoro-5-bromophenoxy)phenyl][[3-(1,1,2,2-tetrafluoroethoxy)phenyl]-methyl]amino]-1,1,1-trifluoro-2-propanol;

(2R)-3-[[3-(4-chloro-3-ethylphenoxy)phenyl][[3-(1,1,2,2-tetrafluoroethoxy)phenyl]-methyl]amino]-1,1,1-trifluoro-2-propanol;

(2R)-3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

(2R)-3-[[3-[3-(pentafluoroethyl)phenoxy]phenyl][[3-(1,1,2,2-tetrafluoroethoxy)-phenyl]methyl]amino]-1,1,1-trifluoro-2-propanol;

(2R)-3-[[3-(3,5-dimethylphenoxy)phenyl][[3-(1,1,2,2-tetrafluoroethoxy)phenyl]-methyl]amino]-1,1,1-trifluoro-2-propanol;

(2R)-3-[[3-(3-ethylphenoxy)phenyl][[3-(1,1,2,2-tetrafluoroethoxy)phenyl]-methyl]amino]-1,1,1-trifluoro-2-propanol;

(2R)-3-[[3-(3-t-butylphenoxy)phenyl][[3-(1,1,2,2-tetrafluoroethoxy)phenyl]-methyl]amino]-1,1,1-trifluoro-2-propanol;

(2R)-3-[[3-(3-methylphenoxy)phenyl][[3-(1,1,2,2-tetrafluoroethoxy)phenyl]-methyl]amino]-1,1,1-trifluoro-2-propanol;
(2R)-3-[[3-(5,6,7,8-tetrahydro-2-naphthoxy)phenyl][[3-(1,1,2,2-tetrafluoro-ethoxy)phenyl]methyl]amino]-1,1,1-trifluoro-2-propanol;
(2R)-3-[[3-(phenoxy)phenyl][[3-(1,1,2,2-tetrafluoroethoxy)phenyl]methyl]amino]-1,1,1-trifluoro-2-propanol;
(2R)-3-[[3-[3-(N,N-dimethylamino)phenoxy]phenyl][[3-(1,1,2,2-tetrafluoro-ethoxy)phenyl]methyl]amino]-1,1,1-trifluoro-2-propanol;
(2R)-3-[[[3-(1,1,2,2,-tetrafluoroethoxy)phenyl]methyl][3-[[3-(trifluoromethoxy)-phenyl]methoxy]phenyl]amino]-1,1,1-trifluoro-2-propanol;
(2R)-3-[[[3-(1,1,2,2-tetrafluoroethoxy)phenyl]methyl][3-[[3-(trifluoro-methyl)phenyl]methoxy]phenyl]amino]-1,1,1-trifluoro-2-propanol;
(2R)-3-[[[3-(1,1,2,2-tetrafluoroethoxy)phenyl]methyl][3-[[3,5-dimethylphenyl]-methoxy]phenyl]amino]-1,1,1-trifluoro-2-propanol;
(2R)-3-[[[3-(1,1,2,2-tetrafluoroethoxy)phenyl]methyl][3-[[3-(trifluoromethylthio)-phenyl]methoxy]phenyl]amino]-1,1,1-trifluoro-2-propanol;
(2R)-3-[[[3-(1,1,2,2-tetrafluoroethoxy)phenyl]methyl][3-[[3,5-difluorophenyl]-methoxy]phenyl]amino]-1,1,1-trifluoro-2-propanol;
(2R)-3-[[[3-(1,1,2,2-tetrafluoroethoxy)phenyl]methyl][3-[cyclohexylmethoxy]-phenyl]amino]-1,1,1-trifluoro-2-propanol;
(2R)-3-[[3-(2-difluoromethoxy-4-pyridyloxy)phenyl][[3-(1,1,2,2-tetrafluoroethoxy)-phenyl]methyl]amino]-1,1,1-trifluoro-2-propanol;
(2R)-3-[[3-(2-trifluoromethyl-4-pyridyloxy)phenyl][[3-(1,1,2,2-tetrafluoroethoxy)-phenyl]methyl]amino]-1,1,1-trifluoro-2-propanol;
(2R)-3-[[3-(3-difluoromethoxyphenoxy)phenyl][[3-(1,1,2,2-tetrafluoroethoxy)-phenyl]methyl]amino]-1,1,1-trifluoro-2-propanol;
(2R)-3-[[[3-(3-trifluoromethylthio)phenoxy]phenyl][[3-(1,1,2,2-tetrafluoroethoxy)-phenyl]methyl]amino]-1,1,1-trifluoro-2-propanol;
(2R)-3-[[3-(4-chloro-3-trifluoromethylphenoxy)phenyl][[3-(1,1,2,2-tetrafluoroethoxy)-phenyl]methyl]amino]-1,1,1-trifluoro-2-propanol;
(2R)-3-[[3-(3-trifluoromethoxyphenoxy)phenyl][[3-(pentafluoroethyl)phenyl]-methyl]amino]-1,1,1-trifluoro-2-propanol;
(2R)-3-[[3-(3-isopropylphenoxy)phenyl][[3-(pentafluoroethyl)phenyl]methyl]-amino]-1,1,1-trifluoro-2-propanol;
(2R)-3-[[3-(3-cyclopropylphenoxy)phenyl][[3-(pentafluoroethyl)phenyl]methyl]-amino]-1,1,1-trifluoro-2-propanol;
(2R)-3-[[3-(3-(2-furyl)phenoxy)phenyl][[3-(pentafluoroethyl)phenyl]methyl]-amino]-1,1,1-trifluoro-2-propanol;
(2R)-3-[[3-(2,3-dichlorophenoxy)phenyl][[3-(pentafluoroethyl)phenyl]methyl]-amino]-1,1,1-trifluoro-2-propanol;
(2R)-3-[[3-(4-fluorophenoxy)phenyl][[3-(pentafluoroethyl)phenyl]methyl]amino]-1,1,1-trifluoro-2-propanol;
(2R)-3-[[3-(4-methylphenoxy)phenyl][[3-(pentafluoroethyl)phenyl]methyl]amino]-1,1,1-trifluoro-2-propanol;
(2R)-3-[[3-(2-fluoro-5-bromophenoxy)phenyl][[3-(pentafluoroethyl)phenyl]methyl]amino]-1,1,1-trifluoro-2-propanol;
(2R)-3-[[3-(4-chloro-3-ethylphenoxy)phenyl][[3-(pentafluoroethyl)phenyl]methyl]amino]-1,1,1-trifluoro-2-propanol;
(2R)-3-[[3-[3-(1,1,2,2-tetrafluoroethoxy)phenoxy]phenyl][[3-(pentafluoroethyl)-phenyl]methyl]amino]-1,1,1-trifluoro-2-propanol;
(2R)-3-[[3-[3-(pentafluoroethyl)phenoxy]phenyl][[3-(pentafluoroethyl)phenyl]-methyl]amino]-1,1,1-trifluoro-2-propanol;
(2R)-3-[[3-(3,5-dimethylphenoxy)phenyl][[3-(pentafluoroethyl)phenyl]methyl]-amino]-1,1,1-trifluoro-2-propanol;
(2R)-3-[[3-(3-ethylphenoxy)phenyl][[3-(pentafluoroethyl)phenyl]methyl]amino]-1,1,1-trifluoro-2-propanol;
(2R)-3-[[3-(3-t-butylphenoxy)phenyl][[3-(pentafluoroethyl)phenyl]methyl]amino]-1,1,1-trifluoro-2-propanol;
(2R)-3-[[3-(3-methylphenoxy)phenyl][[3-(pentafluoroethyl)phenyl]methyl]amino]-1,1,1-trifluoro-2-propanol;
(2R)-3-[[3-(5,6,7,8-tetrahydro-2-naphthoxy)phenyl][[3-(pentafluoroethyl)phenyl]-methyl]amino]-1,1,1-trifluoro-2-propanol;
(2R)-3-[[3-(phenoxy)phenyl][[3(pentafluoroethyl)phenyl]methyl]amino]-1,1,1-trifluoro-2-propanol;
(2R)-3-[[3-[3-(N,N-dimethylamino)phenoxy]phenyl][[3(pentafluoroethyl)phenyl]-methyl]amino]-1,1,1-trifluoro-2-propanol;
(2R)-3-[[[3-(pentafluoroethyl)phenyl]methyl][3-[[3-(trifluoromethoxy)phenyl]-methoxy]phenyl]amino]-1,1,1-trifluoro-2-propanol;
(2R)-3-[[[3-(pentafluoroethyl)phenyl]methyl][3-[[3-(trifluoromethyl)-phenyl]-methoxy]phenyl]amino]-1,1,1-trifluoro-2-propanol;
(2R)-3-[[[3-(pentafluoroethyl)phenyl]methyl][3-[[3,5-dimethylphenyl]methoxy]-phenyl]amino]-1,1,1-trifluoro-2-propanol;
(2R)-3-[[[3-(pentafluoroethyl)phenyl]methyl][3-[[3-(trifluoromethylthio)phenyl]-methoxy]phenyl]amino]-1,1,1-trifluoro-2-propanol;
(2R)-3-[[[3-(pentafluoroethyl)phenyl]methyl][3-[[3,5-difluorophenyl]methoxy]-phenyl]amino]-1,1,1-trifluoro-2-propanol;
(2R)-3-[[[3-(pentafluoroethyl)phenyl]methyl][3-[cyclohexylmethoxy]phenyl]-amino]-1,1,1-trifluoro-2-propanol;
(2R)-3-[[3-(2-difluoromethoxy-4-pyridyloxy)phenyl][[3-(pentafluoroethyl)phenyl]-methyl]amino]-1,1,1-trifluoro-2-propanol;
(2R)-3-[[3-(2-trifluoromethyl-4-pyridyloxy)phenyl][[3-(pentafluoroethyl)phenyl]-methyl]amino]-1,1,1-trifluoro-2-propanol;
(2R)-3-[[3-(3-difluoromethoxyphenoxy)phenyl][[3-(pentafluoroethyl)phenyl]-methyl]amino]-1,1,1-trifluoro-2-propanol;
(2R)-3-[[[3-(3-trifluoromethylthio)phenoxy]phenyl][[3-(pentafluoroethyl)phenyl]-methyl]amino]-1,1,1-trifluoro-2-propanol;
(2R)-3-[[3-(4-chloro-3-trifluoromethylphenoxy)phenyl][(3-(pentafluoroethyl)-phenyl]methyl]amino]-1,1,1-trifluoro-2-propanol;
(2R)-3-[[3-(3-trifluoromethoxyphenoxy)phenyl][[3-(heptafluoropropyl)phenyl]-methyl]amino]-1,1,1-trifluoro-2-propanol;
(2R)-3-[[3-(3-isopropylphenoxy)phenyl][[3-(heptafluoropropyl)phenyl]methyl]-amino]-1,1,1-trifluoro-2-propanol;
(2R)-3-[[3-(3-cyclopropylphenoxy)phenyl][[3-(heptafluoropropyl)phenyl]methyl]-amino]-1,1,1-trifluoro-2-propanol;
(2R)-3-[[3-(3-(2-furyl)phenoxy)phenyl][[3-(heptafluoropropyl)phenyl]methyl]-amino]-1,1,1-trifluoro-2-propanol;

(2R)-3-[[3-(2,3-dichlorophenoxy)phenyl][[3-(heptafluoropropyl)phenyl]methyl]-amino]-1,1,1-trifluoro-2-propanol;
(2R)-3-[[3-(4-fluorophenoxy)phenyl][[3-(heptafluoropropyl)phenyl]methyl]amino]-1,1,1-trifluoro-2-propanol;
(2R)-3-[[3-(4-methylphenoxy)phenyl][[3-(heptafluoropropyl)phenyl]methyl]amino]-1,1,1,-trifluoro-2-propanol;
(2R)-3-[[3-(2-fluoro-5-bromophenoxy)phenyl][[3-(heptafluoropropyl)phenyl]-methyl]amino]-1,1,1-trifluoro-2-propanol;
(2R)-3-[[3-(4-chloro-3-ethylphenoxy)phenyl][[3-(heptafluoropropyl)phenyl]methyl]-amino]-1,1,1-trifluoro-2-propanol;
(2R)-3-[[3-[3-(1,1,2,2-tetrafluoroethoxy)phenoxy]phenyl][[3-(heptafluoropropyl)-phenyl]methyl]amino]-1,1,1-trifluoro-2-propanol;
(2R)-3-[[3-[3-(pentafluoroethyl)phenoxy]phenyl][[3-(heptafluoropropyl)phenyl]-methyl]amino]-1,1,1-trifluoro-2-propanol;
(2R)-3-[[3-(3,5-dimethylphenoxy)phenyl][[3-(heptafluoropropyl)phenyl]methyl]-amino]-1,1,1-trifluoro-2-propanol;
(2R)-3-[[3-(3-ethylphenoxy)phenyl][[3-(heptafluoropropyl)phenyl]methyl]amino]-1,1,1-trifluoro-2-propanol;
(2R)-3-[[3-(3-t-butylphenoxy)phenyl][[3-(heptafluoropropyl)phenyl]methyl]amino]-1,1,1-trifluoro-2-propanol;
(2R)-3-[[3-(3-methylphenoxy)phenyl][[3-(heptafluoropropyl)phenyl]methyl]amino]-1,1,1-trifluoro-2-propanol;
(2R)-3-[[3-(5,6,7,8-tetrahydro-2-naphthoxy)phenyl][[3-(heptafluoropropyl)phenyl]-methyl]amino]-1,1,1-trifluoro-2-propanol;
(2R)-3-[[3-(phenoxy)phenyl][[3-(heptafluoropropyl)phenyl]methyl]amino]-1,1,1-trifluoro-2-propanol;
(2R)-3-[[3-[3-(N,N-dimethylamino)phenoxy]phenyl][[3-(heptafluoropropyl)phenyl]-methyl]amino]-1,1,1-trifluoro-2-propanol;
(2R)-3-[[[3-(heptafluoropropyl)phenyl]methyl][3-[[3-(trifluoromethoxy)phenyl]-methoxy]phenyl]amino]-1,1,1-trifluoro-2-propanol;
(2R)-3-[[[3-(heptafluoropropyl)phenyl]methyl][3-[[3-(trifluoromethyl)phenyl]-methoxy]phenyl]amino]-1,1,1-trifluoro-2-propanol;
(2R)-3-[[[3-(heptafluoropropyl)phenyl]methyl][3-[[3,5-dimethylphenyl]methoxy]-phenyl]amino]-1,1,1-trifluoro-2-propanol;
(2R)-3-[[[3-(heptafluoropropyl)phenyl]methyl][3-[[3-(trifluoromethylthio)phenyl]-methoxy]phenyl]amino]-1,1,1-trifluoro-2-propanol;
(2R)-3-[[[3-(heptafluoropropyl)phenyl]methyl][3-[[3,5-difluorophenyl]methoxy]-phenyl]amino]-1,1,1-trifluoro-2-propanol;
(2R)-3-[[[3-(heptafluoropropyl)phenyl]methyl][3-[cyclohexylmethoxy]phenyl]-amino]-1,1,1-trifluoro-2-propanol;
(2R)-3-[[3-(2-difluoromethoxy-4-pyridyloxy)phenyl][[3-(heptafluoropropyl)phenyl]-methyl]amino]-1,1,1-trifluoro-2-propanol;
(2R)-3-[[3-(2-trifluoromethyl-4-pyridyloxy)phenyl][[3-(heptafluoropropyl)phenyl]-methyl]amino]-1,1,1-trifluoro-2-propanol;
(2R)-3-[[3-(3-difluoromethoxyphenoxy)phenyl][[3-(heptafluoropropyl)phenyl]-methyl]amino]-1,1,1-trifluoro-2-propanol;
(2R)-3-[[[3-(3-trifluoromethylthio)phenoxy]phenyl][[3-(heptafluoropropyl)phenyl]-methyl]amino]-1,1,1-trifluoro-2-propanol;
(2R)-3-[[3-(4-chloro-3-trifluoromethylphenoxy)phenyl][[3-(heptafluoropropyl)-phenyl]methyl]amino]-1,1,1-trifluoro-2-propanol;
(2R)-3-[[3-(3-trifluoromethoxyphenoxy)phenyl][[2-fluoro-5-(trifluoromethyl)-phenyl]methyl]amino]-1,1,1-trifluoro-2-propanol;
(2R)-3-[[3-(3-isopropylphenoxy)phenyl][[2-fluoro-5-(trifluoromethyl)phenyl]-methyl]amino]-1,1,1-trifluoro-2-propanol;
(2R)-3-[[3-(3-cyclopropylphenoxy)phenyl][[2-fluoro-5-(trifluoromethyl)phenyl]-methyl]amino]-1,1,1-trifluoro-2-propanol;
(2R)-3-[[3-(3-(2-furyl)phenoxy)phenyl][[2-fluoro-5-(trifluoromethyl)phenyl]-methyl]amino]-1,1,1-trifluoro-2-propanol;
(2R)-3-[(3-(2,3-dichlorophenoxy)phenyl][[2-fluoro-5-(trifluoromethyl)phenyl]-methyl]amino]-1,1,1-trifluoro-2-propanol;
(2R)-3-[[3-(4-fluorophenoxy)phenyl][[2-fluoro-5-(trifluoromethyl)phenyl]-methyl]amino]-1,1,1-trifluoro-3-propanol;
(2R)-3-[[3-(4-methylphenoxy)phenyl][[2-fluoro-5-(trifluoromethyl)phenyl]-methyl]amino]-1,1,1-trifluoro-2-propanol;
(2R)-3-[[3-(2-fluoro-5-bromophenoxy)phenyl][[2-fluoro-5-(trifluoromethyl)-phenyl]methyl]amino]-1,1,1-trifluoro-2-propanol;
(2R)-3-[[3-(4-chloro-3-ethylphenoxy)phenyl][[2-fluoro-5-(trifluoromethyl)-phenyl]methyl]amino]-1,1,1-trifluoro-2-propanol;
(2R)-3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;
(2R)-3-[[3-[3-(pentafluoroethyl)phenoxy]phenyl][[2-fluoro-5-(trifluoromethyl)-phenyl]methyl]amino]-1,1,1-trifluoro-2-propanol;
(2R)-3-[[3-(3,5-dimethylphenoxy)phenyl][[2-fluoro-5-(trifluoromethyl)phenyl]-methyl]amino]-1,1,1-trifluoro-2-propanol;
(2R)-3-[[3-(3-ethylphenoxy)phenyl][[2-fluoro-5-(trifluoromethyl)phenyl]methyl]-1,1,1-trifluoro-2-propanol;
(2R)-3-[[3-(3-t-butylphenoxy)phenyl][[2-fluoro-5-(trifluoromethyl)phenyl]methyl]-1,1,1-trifluoro-2-propanol;
(2R)-3-[[3-(3-methylphenoxy)phenyl][[2-fluoro-5-(trifluoromethyl)phenyl]methyl]-1,1,1-trifluoro-2-propanol;
(2R)-3-[[3-(5,6,7,8-tetrahydro-2-naphthoxy)phenyl][[2-fluoro-5-(trifluoromethyl)-phenyl]methyl]amino]-1,1,1-trifluoro-2-propanol;
(2R)-3-[[3-(phenoxy)phenyl][[2-fluoro-5-(trifluoromethyl)phenyl]methyl]amino]-1,1,1-trifluoro-2-propanol;
(2R)-3-[[3-[3-(N,N-dimethylamino,phenoxy]phenyl][[2-fluoro-5-(trifluoromethyl)-phenyl]methyl]amino]-1,1,1-trifluoro-2-propanol;
(2R)-3-[[[2-fluoro-5-(trifluoromethyl)phenyl]methyl][3-[[3-(trifluoromethoxy)-phenyl]methoxy]phenyl]amino]-1,1,1-trifluoro-3-propanol;
(2R)-3-[[[2-fluoro-5-(trifluoromethyl)phenyl]methyl][3-[[3-(trifluoromethyl)-phenyl]methoxy]phenyl]amino]-1,1,1-trifluoro-2-propanol;
(2R)-3-[[[2-fluoro-5-(trifluoromethyl)phenyl]methyl][3-[[3,5-dimethylphenyl]-methoxy]phenyl]amino]-1,1,1-trifluoro-2-propanol;

(2R)-3-[[[2-fluoro-5-(trifluoromethyl)phenyl]methyl][3-[[3-(trifluoromethylthio)-phenyl]methoxy]phenyl]amino]-1,1,1-trifluoro-2-propanol;

(2R)-3-[[[2-fluoro-5-(trifluoromethyl)phenyl]methyl][3-[[3,5-difluorophenyl]-methoxy]phenyl]amino]-1,1,1-trifluoro-2-propanol;

(2R)-3-[[[2-fluoro-5-(trifluoromethyl)phenyl]methyl][3-[cyclohexylmethoxy]-phenyl]amino]-1,1,1-trifluoro-2-propanol;

(2R)-3-[[3-(2-difluoromethoxy-4-pyridyloxy)phenyl][[2-fluoro-5-(trifluoromethyl)-phenyl]methyl]amino]-1,1,1-trifluoro-2-propanol;

(2R)-3-[[3-(2-trifluoromethyl-4-pyridyloxy)phenyl][[2-fluoro-5-(trifluoromethyl)-phenyl]methyl]amino]-1,1,1-trifluoro-2-propanol;

(2R)-3-[[3-(3-difluoromethoxyphenoxy)phenyl][[2-fluoro-5-(trifluoromethyl)-phenyl]methyl]amino]-1,1,1-trifluoro-2-propanol;

(2R)-3-[[[3-(3-trifluoromethylthio)phenoxy]phenyl][[2-fluoro-5-(trifluoromethyl)-phenyl]methyl]amino]-1,1,1-trifluoro-2-propanol;

(2R)-3-[[3-(4-chloro-3-trifluoromethylphenoxy)phenyl][[2-fluoro-5-(trifluoro-methyl)phenyl]methyl]amino]-1,1,1-trifluoro-2-propanol;

(2R)-3-[[3-(3-trifluoromethoxyphenoxy)phenyl][[2-fluoro-4-(trifluoromethyl)-phenyl]methyl]amino]-1,1,1-trifluoro-2-propanol;

(2R)-3-[[3-(3-isopropylphenoxy)phenyl][[2-fluoro-4-(trifluoromethyl)phenyl]-methyl]amino]-1,1,1-trifluoro-2-propanol;

(2R)-3-[[3-(3-cyclopropylphenoxy)phenyl][[2-fluoro-4-(trifluoromethyl)phenyl]-methyl]amino]-1,1,1-trifluoro-2-propanol;

(2R)-3-[[3-(3-(2-furyl)phenoxy)phenyl][[2-fluoro-4-(trifluoromethyl)phenyl]-methyl]amino]-1,1,1-trifluoro-2-propanol;

(2R)-3-[[3-(2,3-dichlorophenoxy)phenyl][[2-fluoro-4-(trifluoromethyl)phenyl]-methyl]amino]-1,1,1-trifluoro-2-propanol;

(2R)-3-[[3-(4-fluorophenoxy)phenyl][[2-fluoro-4-(trifluoromethyl)phenyl]-methyl]amino]-1,1,1-trifluoro-2-propanol;

(2R)-3-[[3-(4-methylphenoxy)phenyl][[2-fluoro-4-(trifluoromethyl)phenyl]-methyl]amino]-1,1,1-trifluoro-2-propanol;

(2R)-3-[[3-(2-fluoro-5-bromophenoxy)phenyl][[2-fluoro-4-(trifluoromethyl)-phenyl]methyl]amino]-1,1,1-trifluoro-2-propanol;

(2R)-3-[[3-(4-chloro-3-ethylphenoxy)phenyl][[2-fluoro-4-(trifluoromethyl)-phenyl]methyl]amino]-1,1,1-trifluoro-2-propanol;

(2R)-3-[[3-[3-(1,1,2,2-tetrafluoroethoxy)phenoxy]phenyl][[2-fluoro-4-(trifluoromethyl)phenyl]methyl]amino]-1,1,1-trifluoro-2-propanol;

(2R)-3-[[3-[3-(pentafluoroethyl)phenoxy]phenyl][[2-fluoro-4-(trifluoromethyl)-phenyl]methyl]amino]-1,1,1-trifluoro-2-propanol;

(2R)-3-[[3-(3,5-dimethylphenoxy)phenyl][[2-fluoro-4-(trifluoromethyl)phenyl]-methyl]amino]-1,1,1-trifluoro-2-propanol;

(2R)-3-[[3-(3-ethylphenoxy)phenyl][[2-fluoro-4-(trifluoromethyl)phenyl]methyl]-amino]-1,1,1-trifluoro-2-propanol;

(2R)-3-[[3-(3-t-butylphenoxy)phenyl][[2-fluoro-4-(trifluoromethyl)phenyl]methyl]-amino]-1,1,1-trifluoro-2-propanol;

(2R)-3-[[3-(3-methylphenoxy)phenyl][[2-fluoro-4-(trifluoromethyl)phenyl]methyl]-amino]-1,1,1-trifluoro-2-propanol;

(2R)-3-[[3-(5,6,7,8-tetrahydro-2-naphthoxy)phenyl][[2-fluoro-4-(trifluoromethyl)-phenyl]methyl]amino]-1,1,1-trifluoro-2-propanol;

(2R)-3-[[3-(phenoxy)phenyl][[2-fluoro-4-(trifluoromethyl)phenyl]methyl]amino]-1,1,1-trifluoro-2-propanol;

(2R)-3-[[3-[3-(N,N-dimethylamino)phenoxy]phenyl][[2-fluoro-4-(trifluoromethyl)-phenyl]methyl]amino]-1,1,1-trifluoro-2-propanol;

(2R)-3-[[[2-fluoro-4-(trifluoromethyl)phenyl]methyl](3-[(3-(trifluoromethoxy)phenyl]methoxy]phenyl]amino]-1,1,1-trifluoro-2-propanol;

(3R)-3-[[[2-fluoro-4-(trifluoromethyl)phenyl]methyl][3-[[3-(trifluoromethyl)phenyl]methoxy]phenyl]amino]-1,1,1-trifluoro-2-propanol;

(2R)-3-[[[2-fluoro-4-(trifluoromethyl)phenyl]methyl][3-[[3,5-dimethylphenyl]-methoxy]phenyl]amino]-1,1,1-trifluoro-2-propanol;

(2R)-3-[[[2-fluoro-4-(trifluoromethyl)phenyl]methyl][3-[[3-(trifluoromethylthio)-phenyl]methoxy]phenyl]amino]-1,1,1-trifluoro-2-propanol;

(2R)-3-[[[2-fluoro-4-(trifluoromethyl)phenyl]methyl][3-[[3,5-difluorophenyl]-methoxy]phenyl]amino]-1,1,1-trifluoro-2-propanol;

(2R)-3-[[[2-fluoro-4-(trifluoromethyl)phenyl]methyl][3-[cyclohexylmethoxy]-phenyl]amino]-1,1,1-trifluoro-2-propanol;

(2R)-3-[[3-(2-difluoromethoxy-4-pyridyloxy)phenyl][[2-fluoro-4-(trifluoromethyl)-phenyl]methyl]amino]-1,1,1-trifluoro-2-propanol;

(2R)-3-[[3-(2-trifluoromethyl-4-pyridyloxy)phenyl][[2-fluoro-4-(trifluoromethyl)-phenyl]methyl]amino]-1,1,1-trifluoro-2-propanol;

(2R)-3-[[3-(3-difluoromethoxyphenoxy)phenyl][[2-fluoro-4-(trifluoromethyl)-phenyl]methyl]amino]-1,1,1-trifluoro-2-propanol;

(2R)-3-[[[3-(3-trifluoromethylthio)phenoxy]phenyl][[2-fluoro-4-(trifluoromethyl)-phenyl]methyl]amino]-1,1,1-trifluoro-2-propanol; and (2R)-3-[[3-(4-chloro-3-trifluoromethylphenoxy)phenyl][[2-fluoro-4-(trifluoromethyl)phenyl]methyl]amino]-1,1,1-trifluoro-2-propanol.

Another class of CETP inhibitors that finds utility with the present invention consists of quinolines of Formula XVII

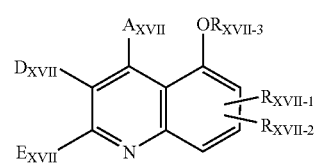

Formula XVII and pharmaceutically acceptable forms thereof, wherein:

$A_{XVII}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$NR_{XVII-4}R_{XVII-5}$ wherein $R_{XVII-4}$ and $R_{XVII-5}$ are identical or different and denote a hydrogen, phenyl or a straight-chain or branched alkyl containing up to 6 carbon atoms, $D_{XVII}$ denotes an aryl containing 6 to 10 carbon atoms, which is optionally substituted with a phenyl, nitro, halogen, trifluoromethyl or trifluoromethoxy, or a radical according to the formula $R_{XVII-6}$-$L_{XVII}$-,     $R_{XVII-8}$ $R_{XVII-9}$,     or $R_{XVII-7}$ $R_{XVIII0}$-$T_{XVII}$-$V_{XVII}$-$X_{XVII}$- wherein $R_{XVII-6}$, $R_{XVII-7}$, $R_{XVII-10}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteroatoms from the series of S, N and/or O, and/or in the form of a group according to the formula —$OR_{XVII-11}$, —$SR_{XVII-12}$, —$SO_2R_{XVII-13}$, or —$NR_{XVII-14}R_{XVII-15}$;

$R_{XVII-11}$, $R_{XVII-12}$, and $R_{XVII-13}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{XVII-14}$ and $R_{XVII-15}$ are identical or different and have the meaning of $R_{XVII-4}$ and $R_{XVII-5}$ given above, or $R_{XVII-6}$ and/or $R_{XVII-7}$ denote a radical according to the formula

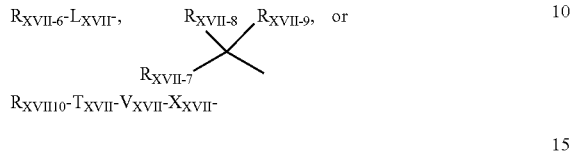

$R_{XVII-8}$ denotes a hydrogen or halogen, and $R_{XVII-9}$ denotes a hydrogen, halogen, azido, trifluoromethyl, hydroxyl, trifluoromethoxy, a straight-chain or branched alkoxy or alkyl containing up to 6 carbon atoms each, or a radical according to the formula $NR_{XVII-16}R_{XVII-17}$;

$R_{XVII-16}$ and $R_{XVII-17}$ are identical or different and have the meaning of $R_{XVII-4}$ and $R_{XVII-5}$ above; or $R_{XVII-8}$ and $R_{XVII-9}$ together form a radical according to the formula =O or =$NR_{XVII-18}$;

$R_{XVII-18}$ denotes a hydrogen or a straight-chain or branched alkyl, alkoxy or acyl containing up to 6 carbon atoms each;

$L_{XVII}$ denotes a straight-chain or branched alkylene or alkenylene chain containing up to 8 carbon atoms each, which are optionally substituted with up to two hydroxyl groups;

$T_{XVII}$ and $X_{XVII}$ are identical or different and denote a straight-chain or branched alkylene chain containing up to 8 carbon atoms; or $T_{XVII}$ and $X_{XVII}$ denotes a bond;

$V_{XVII}$ denotes an oxygen or sulfur atom or —$NR_{XVII-19}$;

$R_{XVII-19}$ denotes a hydrogen or a straight-chain or branched alkyl containing up to 6 carbon atoms or a phenyl;

$E_{XVII}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl;

$R_{XVII-1}$ and $R_{XVII-2}$ are identical or different and denote a cycloalkyl containing 3 to 8 carbon atoms, hydrogen, nitro, halogen, trifluoromethyl, trifluoromethoxy, carboxy, hydroxy, cyano, a straight-chain or branched acyl, alkoxycarbonyl or alkoxy with up to 6 carbon atoms, or $NR_{XVII-20}R_{XVII-21}$;

$R_{XVII-20}$ and $R_{XVII-21}$ are identical or different and denote hydrogen, phenyl, or a straight-chain or branched alkyl with up to 6 carbon atoms; and or $R_{XVII-1}$ and/or $R_{XVII-2}$ are straight-chain or branched alkyl with up to 6 carbon atoms, optionally substituted with halogen, trifluoromethoxy, hydroxy, or a straight-chain or branched alkoxy with up to 4 carbon atoms, aryl containing 6-10 carbon atoms optionally substituted with up to five of the same or different substituents selected from halogen, cyano, hydroxy, trifluoromethyl, trifluoromethoxy, nitro, straight-chain or branched alkyl, acyl, hydroxyalkyl, alkoxy with up to 7 carbon atoms and $NR_{XVII-22}R_{XVII-23}$;

$R_{XVII-22}$ and $R_{XVII-23}$ are identical or different and denote hydrogen, phenyl or a straight-chain or branched alkyl up to 6 carbon atoms; and/or $R_{XVII-1}$ and $R_{XVII-2}$ taken together form a straight-chain or branched alkene or alkane with up to 6 carbon atoms optionally substituted with halogen, trifluoromethyl, hydroxy or straight-chain or branched alkoxy with up to 5 carbon atoms;

$R_{XVII-3}$ denotes hydrogen, a straight-chain or branched acyl with up to 20 carbon atoms, a benzoyl optionally substituted with halogen, trifluoromethyl, nitro or trifluoromethoxy, a straight-chained or branched fluoroacyl with up to 8 carbon atoms and 7 fluoro atoms, a cycloalkyl with 3 to 7 carbon atoms, a straight chained or branched alkyl with up to 8 carbon atoms optionally substituted with hydroxyl, a straight-chained or branched alkoxy with up to 6 carbon atoms optionally substituted with phenyl which may in turn be substituted with halogen, nitro, trifluoromethyl, trifluoromethoxy, or phenyl or a tetrazol substituted phenyl, and/or an alkyl that is optionally substituted with a group according to the formula —$OR_{XVII-24}$;

$R_{XVII-24}$ is a straight-chained or branched acyl with up to 4 carbon atoms or benzyl.

Compounds of Formula XVII and their methods of manufacture are disclosed in PCT Publication No. WO 98/39299, which is incorporated herein by reference in its entirety for all purposes.

Another class of CETP inhibitors that finds utility with the present invention consists of 4-Phenyltetrahydroquinolines of Formula XVIII

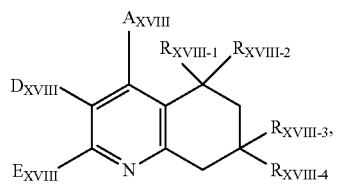

Formula XVIII

N oxides thereof, and pharmaceutically acceptable forms thereof, wherein:
- $A_{XVIII}$ denotes a phenyl optionally substituted with up to two identical or different substituents in the form of halogen, trifluoromethyl or a straight-chain or branched alkyl or alkoxy containing up to three carbon atoms;
- $D_{XVIII}$ denotes the formula

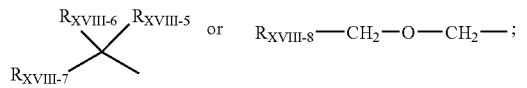

- $R_{XVIII-5}$ and $R_{XVIII-6}$ are taken together to form =O; or
- $R_{XVIII-5}$ denotes hydrogen and $R_{XVIII-6}$ denotes halogen or hydrogen; or
- $R_{XVIII-5}$ and $R_{XVIII-6}$ denote hydrogen;
- $R_{XVIII-7}$ and $R_{XVIII-8}$ are identical or different and denote phenyl, naphthyl, benzothiazolyl, quinolinyl, pyrimidyl or pyridyl with up to four identical or different substituents in the form of halogen, trifluoromethyl, nitro, cyano, trifluoromethoxy, $-SO_2-CH_3$ or $NR_{XVIII-9}R_{XVIII-10}$;
- $R_{XVIII-9}$ and $R_{XVIII-10}$ are identical or different and denote hydrogen or a straight-chained or branched alkyl of up to three carbon atoms;
- $E_{XVIII}$ denotes a cycloalkyl of from three to six carbon atoms or a straight-chained or branched alkyl of up to eight carbon atoms;
- $R_{XVIII-1}$ denotes hydroxy;
- $R_{XVIII-2}$ denotes hydrogen or methyl;
- $R_{XVIII-3}$ and $R_{XVIII-4}$ are identical or different and denote straight-chained or branched alkyl of up to three carbon atoms; or
- $R_{XVIII-3}$ and $R_{XVIII-4}$ taken together form an alkenylene made up of between two and four carbon atoms.

Compounds of Formula XVIII and their methods of manufacture are disclosed in PCT Publication No. WO 99/15504 and U.S. Pat. No. 6,291,477, both of which are incorporated herein by reference in their entireties for all purposes.

The present invention is particularly advantageous for the class of drugs which are both acid-sensitive and low-solubility. Exemplary acid-sensitive, low-solubility drugs include (+)-N-{3-[3-(4-fluorophenoxy)phenyl]-2-cyclopenten-1-yl}-N-hydroxyurea; omeprazole; etoposide; famotidine; erythromycin; quinapril; lansoprazole; progabide; as well as CCR1 inhibitors such as quinoxaline-2-carboxylic acid [4(R)-carbamoyl-1(S)-3-fluorobenzyl-2(S),7-dihydroxy-7-methyl-octyl]amide and quinoxaline-2-carboxylic acid [1-benzyl-4-(4,4-difluoro-1-hydroxy-cyclohexyl)-2-hydroxy-4-hydroxycarbamoyl-butyl]-amide.

The invention is useful for improving the intrinsic dissolution rate of compounds selected from the following. The intrinsic dissolution rate is defined as the rate of dissolution of a pure pharmaceutical active ingredient when conditions such as surface area, agitation-stirring speed, pH and ionic-strength of the dissolution medium are kept constant. Intrinsic dissolution rate is further defined as being measured in water at 37° C. using a USP II dissolution apparatus equipped with a Wood's apparatus (Wood, J H; Syarto, J E and Letterman, H: J. Pharm. Sci. 54 (1965), 1068) with a stirring speed of 50 rpm. The intrinsic dissolution rate is defined in terms of mg of drug dissolved per minute from a unit surface area, therefore, the intrinsic dissolution rate is referred to in units of $mg/min.cm^2$.

The compositions and methods of the invention are particularly useful for compounds with an intrinsic dissolution rate of preferably less than 0.1 $mg/min·cm^2$ and more preferably with less than 0.05 $mg/min·cm^2$.

Turning now to the chemical structures of specific CCR1 inhibitors, one class of CCR1 inhibitors that finds utility with the present invention consists of dihydroxyhexanoic acid derivatives having the Formula CCR1-I

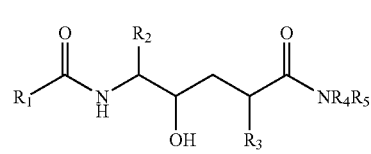

CCR1-I wherein $R_1$ is ($C_2$-$C_9$) heteroaryl optionally substituted with one, two or three substituents independently selected from the group consisting of hydrogen, halo, cyano, ($C_1$-$C_6$) alkyl optionally substituted with one, two or three fluorine atoms, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$-amino, amino($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, [($C_1$-$C_6$)alkyl]$_2$N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)-[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl;

wherein $R_2$ is phenyl-($CH_2$)$_m$—, naphthyl-($CH_2$)$_m$—, ($C_3$-$C_{10}$)cycloalkyl-($CH_2$)$_m$—, ($C_1$-$C_6$)alkyl or ($C_2$-$C_9$)heteroaryl-($CH_2$)$_m$—, wherein each of said phenyl, naphthyl, ($C_3$-$C_{10}$)cycloalkyl or ($C_2$-$C_9$)heteroaryl moieties of said phenyl-($CH_2$)$_m$—, naphthyl-($CH_2$)$_m$—, ($C_3$-$C_{10}$)cycloalkyl-($CH_2$)$_m$— or ($C_2$-$C_9$)heteroaryl-($CH_2$)$_m$— groups may optionally be substituted with one, two, or three substituents independently selected from the group consisting of hydrogen, halo, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)-[NH]$(C_1-C_6)$alkyl, $(C_1-C_6)$alkyl(C=O)-[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkyl HN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, phenoxy, benzyloxy, $(C_3-C_{10})$cycloalkyl, $(C_2-C_9)$heterocycloalkyl, and $(C_2-C_9)$heteroaryl;

wherein $R_3$ is hydrogen, $(C_1-C_{10})$alkyl, $(C_3-C_{10})$cycloalkyl-$(CH_2)_n$—, $(C_2-C_9)$heterocycloalkyl-$(CH_2)_n$—, $(C_2-C_9)$heteroaryl-$(CH_2)_n$— or aryl-$(CH_2)_n$—; wherein n is an integer from zero to six;

wherein said $R_3$ $(C_1-C_{10})$alkyl group may optionally be substituted with one or more substituents, (preferably from one to three substituents) independently selected from hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)-[NH]$(C_1-C_6)$alkyl, $(C_1-C_6)$alkyl(C=O)-[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkyl HN—$SO_2$—$(C_1-C_6)$alkyl, $[(C_1-C_6)$alkyl$]_2$ N—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl; and wherein any of the carbon-carbon single bonds of said $(C_1-C_{10})$alkyl may optionally be replaced by a carbon-carbon double bond;

wherein the $(C_3-C_{10})$cycloalkyl moiety of said $R_3$ $(C_3-C_{10})$cycloalkyl-$(CH_2)_n$— group may optionally be substituted by one to three substituents independently selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O), $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)-[NH]$(C_1-C_6)$alkyl, $(C_1-C_6)$alkyl(C=O)-[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkyl HN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

wherein the $(C_2-C_9)$heterocycloalkyl moiety of said $R_3$ $(C_2-C_9)$heterocycloalkyl-$(CH_2)_n$— group may contain from one to three heteroatoms independently selected from nitrogen, sulfur, oxygen, >S(=O), >$SO_2$ or >$NR^6$, wherein said $(C_2-C_9)$heterocycloalkyl moiety of said $(C_2-C_9)$heterocycloalkyl-$(CH_2)_n$— group may optionally be substituted on any of the ring carbon atoms capable of forming an additional bond (preferably one to three substituents per ring) with a substituent independently selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)-[NH]$(C_1-C_6)$alkyl, $(C_1-C_6)$alkyl(C=O)-[N$(C_1-C_6)$alkyl]$(C_1-C_6)$alkyl, $(C_1-C_6)$alkyl-S—, $(C_1-C_6)$alkyl-(S=O), $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

wherein the $(C_2-C_9)$heteroaryl moiety of said $R_3$ $(C_2-C_9)$heteroaryl-$(CH_2)_n$— group may contain from one to three heteroatoms independently selected from nitrogen, sulfur or oxygen, wherein said $(C_2-C_9)$heteroaryl moiety of said $(C_2-C_9)$heteroaryl-$(CH_2)_n$— group may optionally be substituted on any of the ring carbon atoms capable of forming an additional bond (preferably one to three substituents per ring) with a substituent selected from the group consisting of hydrogen, halo, CN, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)-[NH]$(C_1-C_6)$alkyl, $(C_1-C_6)$alkyl(C=O)-[N$(C_1-C_6)$alkyl]$(C_1-C_6)$alkyl, $(C_1-C_6)$alkyl-S—, $(C_1-C_6)$alkyl- (S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl; and wherein said aryl moiety of said $R_3$ aryl-($CH_2$)$_n$— group is optionally substituted phenyl or naphthyl, wherein said phenyl and naphthyl may optionally be substituted with from one to three substituents independently selected from the group consisting of hydrogen, halo, CN, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$amino, amino($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, [($C_1$-$C_6$)alkyl]$_2$N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)-[NH]($C_1$-$C_6$)alkyl, ($C_1$-$C_6$)alkyl(C=O)-[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkyl HN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl;

or $R_3$ and the carbon to which it is attached form a five to seven membered carbocyclic ring, wherein any of the carbon atoms of said five membered carbocyclic ring may optionally be substituted with a substituent selected from the group consisting of hydrogen, halo, CN, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$amino, amino($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, [($C_1$-$C_6$)alkyl]$_2$N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)-[NH]($C_1$-$C_6$)alkyl, ($C_1$-$C_6$)alkyl(C=O)-[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl; wherein one of the carbon-carbon bonds of said five to seven membered carbocyclic ring may optionally be fused to an optionally substituted phenyl ring, wherein said substituents may be independently selected from hydrogen, halo, CN, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$amino, amino($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, ($C_1$-$C_6$)alkyl-NH—(C=O)—, [($C_1$-$C_6$)alkyl]$_2$N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)-[NH]($C_1$-$C_6$)alkyl, ($C_1$-$C_6$)alkyl(C=O)-[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$, phenyl, ($C_3$-$C_{10}$)cycloalkyl, ($C_2$-$C_9$)heterocycloalkyl, and ($C_2$-$C_9$)heteroaryl;

wherein $R_4$ is hydrogen, ($C_1$-$C_6$)alkyl, hydroxy, ($C_1$-$C_6$)alkoxy, hydroxy($C_1$-$C_6$)alkyl, ($C_1$-$C_6$)alkoxy(C=O)—, ($C_3$-$C_{10}$)cycloalkyl-($CH_2$)$_q$—, ($C_2$-$C_9$)heterocycloalkyl-($CH_2$)$_q$—, ($C_2$-$C_9$)heteroaryl-($CH_2$)$_q$—, phenyl-($CH_2$)$_q$—, or naphthyl-($CH_2$)$_q$—; wherein said ($C_2$-$C_9$)heterocycloalkyl, ($C_2$-$C_9$)heteroaryl, phenyl and naphthyl groups may be optionally substituted with one or two substituents from the group consisting of hydrogen, halo, cyano, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$ amino, amino($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, [($C_1$-$C_6$)alkyl]$_2$N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)-[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$, phenyl, ($C_3$-$C_{10}$)cycloalkyl, ($C_2$-$C_9$)heterocycloalkyl, and ($C_2$-$C_9$)heteroaryl;

wherein $R_5$ is hydrogen, ($C_1$-$C_6$)alkyl or amino; or $R_4$ and $R_5$ together with the nitrogen atom to which they are attached form a ($C_2$-$C_9$)heterocycloalkyl group optionally substituted with one or two substituents selected from the group consisting of hydrogen, halo, cyano, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$) alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$ amino, amino($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2N$—(C=O)—, ($C_1$-$C_6$)alkyl-NH—(C=O)—, [($C_1$-$C_6$)alkyl]$_2$N—(C=O)—, $H_2N$(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)-[NH]($C_1$-$C_6$)alkyl, ($C_1$-$C_6$)alkyl(C=O)-[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2N$—$SO_2$—, $H_2N$—$SO_2$—($C_1$-$C_6$)alkyl, ($C_1$-$C_6$)alkylHN—$SO_2$—($C_1$-$C_6$)alkyl, [($C_1$-

$C_6$)alkyl]$_2$N—SO$_2$—($C_1$-$C_6$)alkyl, CF$_3$SO$_3$—, ($C_1$-$C_6$)alkyl-SO$_3$—, phenyl, ($C_3$-$C_{10}$)cycloalkyl, ($C_2$-$C_9$)heterocycloalkyl, and ($C_2$-$C_9$)heteroaryl;

wherein R$^6$ is hydrogen, ($C_1$-$C_6$)alkyl, ($C_1$-$C_6$)alkoxy-(CH$_2$)$_g$—, ($C_1$-$C_6$)alkoxy(C=O)—(CH$_2$)$_g$—, ($C_1$-$C_6$)alkyl-(SO$_2$)—(CH$_2$)$_g$—, ($C_6$-$C_{10}$)aryloxy-(CH$_2$)$_g$—, ($C_6$-$C_{10}$)aryloxy(C=O)—(CH$_2$)$_g$—, or ($C_6$-$C_{10}$)aryl-(SO$_2$)—(CH$_2$)$_g$—;

wherein g is an integer from zero to four;

wherein m is an integer from zero to four;

wherein n is an integer from zero to six;

with the proviso that when one of R$^4$ or R$^5$ is hydrogen, and the other of R$^4$ or R$^5$ is ($C_1$-$C_6$)alkyl; R$^2$ is ($C_3$-$C_{10}$)cycloalkyl or isopropyl and R$^3$ is ($C_3$-$C_5$)alkyl, phenyl, methylvinyl, dimethylvinyl, halovinyl, hydroxy($C_1$-$C_3$)alkyl or amino($C_1$-$C_4$)alkyl then R$^1$ must be other than indol-5-yl, 6-azaindol-2-yl, 2,3-dichloro-pyrrol-5-yl, 4-hydroxyquinolin-3-yl, 2-hydroxyquinoxalin-3-yl, 6-azaindolin-3-yl, or optionally substituted indol-2 or 3-yl;

and the pharmaceutically acceptable salts of such compounds.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Such alkyl and alkoxy groups may be substituted with one, two or three halogen and/or hydroxy atoms, preferably fluorine atoms.

Unless otherwise indicated, "halogen" includes fluorine, chlorine, bromine, and iodine.

"($C_3$-$C_{10}$)cycloalkyl" when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl, and the like.

"($C_2$-$C_9$)heterocycloalkyl" when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, and the like. One of ordinary skill in the art will understand that the connection of said ($C_2$-$C_9$)heterocycloalkyl rings is through a carbon or a sp$^3$ hybridized nitrogen heteroatom.

"($C_2$-$C_9$)heteroaryl" when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, and the like. One of ordinary skill in the art will understand that the connection of said ($C_2$-$C_9$)heterocycloalkyl rings is through a carbon atom or a sp$^3$ hybridized nitrogen heteroatom.

"Aryl" when used herein refers to phenyl or naphthyl.

"Protected amine" and "protected amino" refers to an amine group with one of the hydrogen atoms replaced with a protecting group (P). Any suitable protecting group may be used for amine protection. Suitable protecting groups include carbobenzyloxy, t-butoxy carbonyl (BOC) or 9-fluorenyl-methylenoxy carbonyl.

Compounds of Formula CCR1-I and their methods of manufacture are disclosed in commonly assigned U.S. patent application Ser. No. 09/380,269, filed Feb. 5, 1998, U.S. patent application Ser. No. 09/403,218, filed Jan. 18, 1999, PCT Publication No. WO98/38167, and PCT Publication No. WO99/40061, all of which are incorporated herein by reference in their entireties for all purposes.

In a preferred embodiment, the CCR1 inhibitor is selected from one of the following compounds of Formula CCR1-I:

quinoxaline-2-carboxylic acid 4(R)-carbamoyl-1(S)-(3-chloro-benzyl)-2(S),7-dihydroxy-7-methyl-octyl]-amide;

7,8-difluoro-quinoline-3-carboxylic acid (1S)-benzyl-4(R)-carbamoyl-2(S),7-dihydroxy-7-methyl-octyl)-amide;

6,7,8-trifluoro-quinoline-3-carboxylic acid (1(S)-benzyl-4(R)-carbamoyl-2(S),7-dihydroxy-7-methyl-octyl)-amide;

quinoxaline-2-carboxylic acid [4(R)-carbamoyl-1(S)-(3-fluoro-benzyl)-2(S),7-dihydroxy-7-methyl-octyl]-amide;

quinoxaline-2-carboxylic acid (1(S)-benzyl-2(S),7-dihydroxy-4(R)-hydroxycarbamoyl-7-methyl-octyl)-amide;

quinoxaline-2-carboxylic acid [4(R)-carbamoyl-1(S)-(2-chloro-benzyl)-2(S),7-dihydroxy-7-methyl-octyl]-amide;

quinoxaline-2-carboxylic acid [1(S)-(2-fluoro-benzyl)-2(S),7-dihydroxy-4(R)-hydroxycarbamoyl-7-methyl-octyl]-amide;

quinoxaline-2-carboxylic acid [4(R)-carbamoyl-1(S)-(2-fluoro-benzyl)-2(S),7-dihydroxy-7-methyl-octyl]-amide;

quinoxaline-2-carboxylic acid [1(S)-(3,4-difluoro-benzyl)-2(S),7-dihydroxy-4(R)-hydroxycarbamoyl-7-methyl-octyl]-amide;

quinoxaline-2-carboxylic acid [4(R)-carbamoyl-1(S)-(3,4-difluoro-benzyl)-2(S),7-dihydroxy-7-methyl-octyl]-amide;

quinoxaline-2-carboxylic acid (4(R)-carbamoyl-2(S),7-dihydroxy-7-methyl-1(S)-naphthalen-1-ylmethyl-octyl)-amide;

7,8-difluoro-quinoline-3-carboxylic acid 1(S)-benzyl-2(S)-hydroxy-7-methyl-4(R)-methylcarbamoyl-octyl)-amide;

8-fluoro-quinoline-3-carboxylic acid 1(S)-benzyl-2(S)-hydroxy-7-methyl-4(R)-methylcarbamoyl-octyl)-amide;

quinoxaline-2-carboxylic acid [4(R)-carbamoyl-7-fluoro-1-(3(S)-fluoro-benzyl)-2(S)-hydroxy-7-methyl-octyl]-amide;

quinoxaline-2-carboxylic acid [4(R)-carbamoyl-1-(2(S)-fluoro-benzyl)-2(S)-hydroxy-7-methyl-octyl]-amide;

quinoxaline-2-carboxylic acid [1(S)-benzyl-4(S)-carbamoyl-4(S)-(2,6-dimethyl-tetrahydro-pyran-4-yl)-2(S)-hydroxy-butyl]-amide;

quinoxaline-2-carboxylic acid 1 (S)-benzyl-4(R)-carbamoyl-7-fluoro-2(S)-hydroxy-7-methyl-octyl)-amide;

quinoxaline-2-carboxylic acid 1(S)-benzyl-5-cyclohexyl-2(S)-hydroxy-4(R)-methylcarbamoyl-pentyl)-amide;

quinoxaline-2-carboxylic acid 1(S)-cyclohexylmethyl-2(S)-hydroxy-7-methyl-4(R)-methylcarbamoyl-octyl)-amide;

quinoxaline-2-carboxylic acid [1(S)-benzyl-2(S)-hydroxy-4(S)-hydroxycarbamoyl-4-(1-hydroxy-4-methyl-cyclohexyl)-butyl-amide;

quinoxaline-2-carboxylic acid [1(S)-benzyl-4(S)-(4,4-difluoro-1-hydroxy-cyclohexyl)-2(S)-hydroxy-4-hydroxycarbamoyl-butyl]-amide;

quinoxaline-2-carboxylic acid [1(S)-benzyl-4(S)-carbamoyl-4(S)-(4,4-difluoro-cyclohexyl)-2(S)-hydroxy-butyl]-amide;

quinoline-3-carboxylic acid (1(S)-benzyl-4(S)-carbamoyl-4-cyclohexyl-2(S)-hydroxy-butyl)-amide;

quinoxaline-2-carboxylic acid (4(R)-carbamoyl-2(S)-hydroxy-7-methyl-1(S)-thiophen-2-ylmethyl-octyl)-amide;
quinoxaline-2-carboxylic acid 1(S)-benzyl-4(R)-carbamoyl-7-chloro-2(S)-hydroxy-oct-6-enyl)-amide;
quinoxaline-2-carboxylic acid 1(S)-benzyl-4(R)-carbamoyl-2(S)-hydroxy-5-phenyl-pentyl)-amide;
N-1(S)-benzyl-4(R)-carbamoyl-7-fluoro-2(S)-hydroxy-7-methyl-octyl)-5,6-dichloro-nicotinamide;
quinoxaline-2-carboxylic acid (4(R)-carbamoyl-2(S)-hydroxy-7-methyl-1(S)-thiazol-4(R)-ylmethyl-octyl)-amide;
benzothiazole-2-carboxylic acid 1(S)-benzyl-4(R)-carbamoyl-7-fluoro-2(S)-hydroxy-7-methyl-octyl)-amide; and
benzofuran-2-carboxylic acid 1(S)-benzyl-4(R)-carbamoyl-7-fluoro-2(S)-hydroxy-7-methyl-octyl)-amide.

In another preferred embodiment, the CCR1 compound has a formula Ia-1:

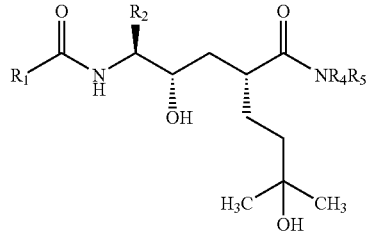

(Ia-1)

wherein the substituents are as defined above.

In a preferred method of making the compound Ia-1, the reaction is started with Scheme 1. In the herein described processes, the substituents are as defined for CCR1-I, and the following:

$R_7$ is hydroxy, ($C_1$-$C_6$)alkyl, or phenyl wherein the phenyl group unsubstituted or substituted with one, two, or three ($C_1$-$C_6$)alkyl, hydroxy, or halogen groups;

$R_8$ is hydroxy or halogen;

$R_9$ is phenyl, naphthyl, ($C_3$-$C_{10}$)cycloalkyl, ($C_1$-$C_6$)alkyl or ($C_2$-$C_9$)heteroaryl, wherein each of said phenyl, naphthyl, ($C_3$-$C_{10}$)cycloalkyl or ($C_2$-$C_9$)heteroaryl groups may be unsubstituted or substituted with one, two, or three substituents independently selected from the group consisting of halogen, cyano, and ($C_1$-$C_6$) alkyl;

P is a protecting group;

X is hydroxy or halogen; and q is 0, 1, 2, 3, or 4.

Scheme 1

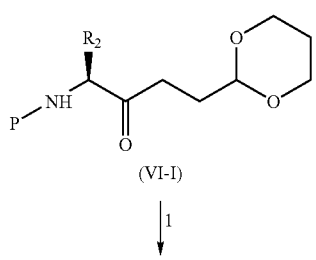

(VI-I)

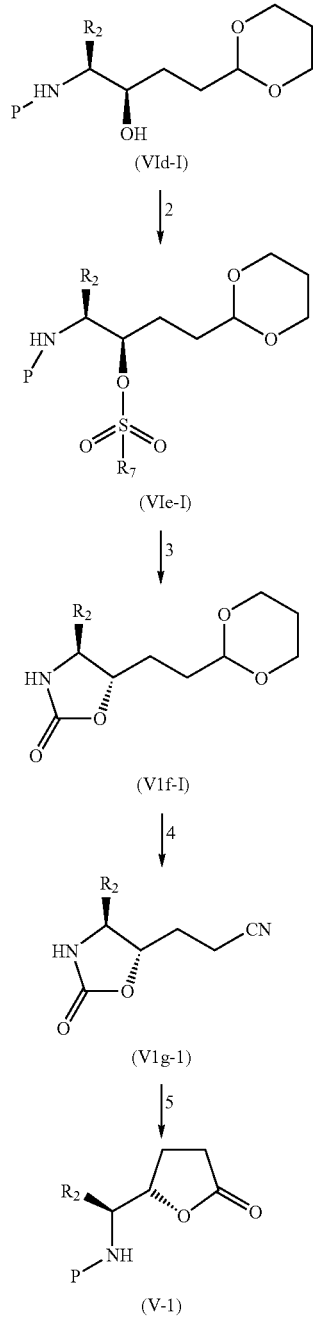

In scheme 1 step 1, a compound of the formula (VI-1) is reduced with a reducing agent under heat to form a compound of the formula (VId-1). In one embodiment, the reducing agent is aluminum triisopropoxide and isopropanol. Preferably, the temperature is maintained above room temperature, more preferably between about 60° C. and about 82° C. The product alcohol can be isolated by either cooling the reaction mixture to room temperature, diluting with more isopropanol and collecting the crystalline material or by cooling the reaction to room temperature and adding 1N HCL and water and collecting the crystalline material.

Step 2 of scheme 1 includes reacting a compound of the formula $R_7$—$SO_2$—X and a compound of the formula (VId-1) in the presence of a base to form the compound of the formula (VIe-1). Any amine base is suitable, including pyridine, triethylamine, N-methylmayholine, and diisoyropylethylamine. In one embodiment, $R_7$—SO2-$R_8$ is p-toluenesulfonic acid, methanesulfonic acid, sulfuric acid, or methanesulfonyl chloride. In another embodiment, the conversion of hydroxy dioxane (VId-1) to dioxane oxazolidinone (VIe-1) can be achieved by treatment of the hydroxy dioxane (VId-1) with methanesulfonyl chloride and triethylamine in tetrahydrofuran solution and heating the mixture to cause the cyclization of the mesylate formed in situ to the oxazolidinone.

In step 3 of scheme 1, a compound of the formula (VIf-1) may be formed by heating the compound of the formula (VIe-1). The reaction may proceed by dissolving compound VIe-1 in a solvent such as pyridine or N-methyl imidazole and heating the mixture for several hours at temperature from about 50° C. to about 100° C.; preferably at about 80° C. The mesylate (VIf-1) may be recovered by extraction into an organic solvent such as ethyl acetate and removal of the amine solvents by extraction of the solution with aqueous acid.

Step 4 of scheme 1 depicts reacting hydroxylamine hydrochloride, a compound of the formula $R_7SO2$-X, and a compound of the formula (VIf-1) to form a compound of the formula (VIg-1). In one embodiment, $R_7$—SO2-X is p-toluenesulfonic acid, methanesulfonic acid, sulfuric acid, or methanesulfonyl chloride. The reaction may occur in a solvent, such as methanol. In one embodiment, the reaction occurs in methanol with tosic acid at reflux for 8 to 24 hours. The resulting nitrile oxazolidinone contains a small amount of the corresponding ethyl ester which is not removed since it also is converted to the desired lactone in subsequent steps.

Step 5 of scheme 1 includes a) hydrolyzing a compound of the formula (VIg-1) with an aqueous solution in the presence of a base, b) protecting the amine group of the compound so formed, and c) cyclizing the compound so formed with heat and an acid catalyst. In one embodiment, the compound VIg-1 is hydrolyzed with sodium hydroxide. The pH is adjusted to approximately 10 and tetrahydrofuran and BOC dicarbonate are added. This provides the protected hydroxy acid, which may be heated in 10% acetic acid and toluene to provide the protected amine lactone (V-1).

The compound of formula (V-1) may also be produced according to scheme 2.

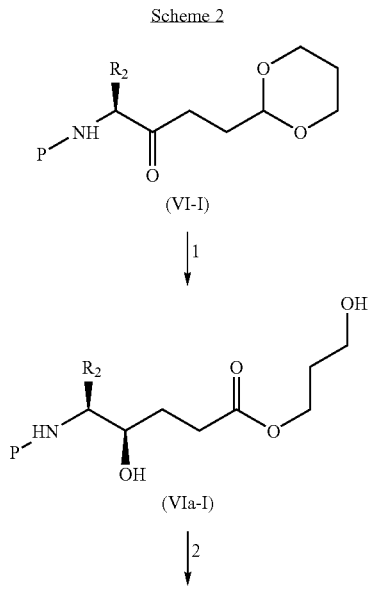

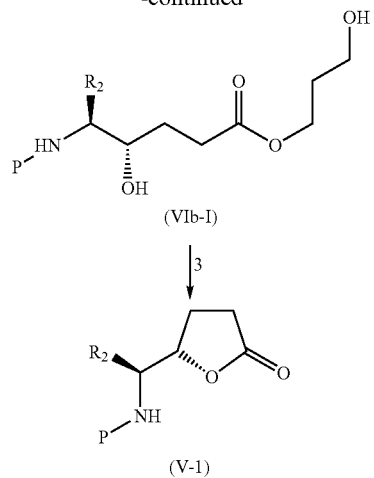

In step 1 of scheme 2, a compound of the formula (VI-1) may be reacted with ozone to for a compound of the formula (VIa-1). The compound VI-1 may be present in a solvent, such as ethyl acetate, and the ozone introduced through sparging at a temperature below room temperature, preferably at about −15° C., until the starting dioxane ketone is substantially reacted. Any excess ozone may be removed by bubbling nitrogen through the solution. The resulting crude ketone ester mixture may be isolated after treatment with aqueous sodium bisulfite to remove any hydroperoxides.

Alternatively, in step 1 of scheme 2, the compound of the formula (VIa-1) may be formed by reacting hypochlorous acid and a compound of the formula (VI-1). Such an oxidation reaction typically produces chlorinated forms of the compound VIa-1 as side products in addition o the compound VIa-1. This oxidation reaction proceeds by mixing the compound VI-1 in solvent, such as acetic acid and/or acetone, and adding sodium hypochlorite, while keeping the mixture at a low temperature, preferably at or below about 0° C.

As a means to convert the side product chlorinated forms of the compound VIa-1 to compounds of the formula V-1, the compounds formed from the hypochlorous acid oxidation reaction may optionally be hydrogenated by reaction with hydrogen in the presence of a catalyst. The hydrogenation may include introducing the products from the hypochlorous acid oxidation reaction into a solvent system of tetrahydrofuran and water, followed by addition of a Pd/C catalyst. The resulting mixture is subjected to hydrogen above atmospheric pressure and temperature. In one embodiment, the pressure is about 80 pounds per square inch and the temperature is maintained from about 60° C. to about 70° C. until the reaction is substantially complete.

In step 2 of scheme 2, the compound of the formula (VIb-1) may be formed by reacting a silyating agent and a compound of the formula (VIa-1) and reacting the compound so formed with a reducing agent. In one embodiment, the reducing agent is N-selectride. In another embodiment, the silyating agent is 1,1,1,3,3,3-hexamethyl-disilazane. The reduction reaction may occur at temperatures below about 0° C., preferably below about −20° C., more preferably below about −50° C. In addition, the reducing agent may be present in slight excess.

In step 3 of scheme 2, the compound of the formula (V-1) is formed by heating a compound of the formula (VIb-1) in the presence of an acid catalyst, such as acetic acid. In one embodiment, the cyclization reaction occurs by introducing the compound VIb-1 into a solvent mixture, such as toluene and 10% acetic acid, at the solvent reflux temperature for 8 to 16 hours. This provides the desired lactone as a crystalline solid after work up.

One method of making the compound of the formula (VI-1) is by reacting a compound of the formula (VII-1)

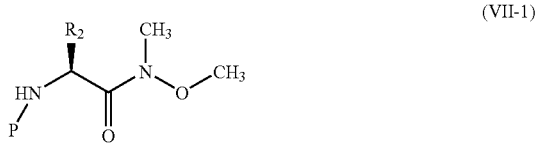

(VII-1)

with a Grinard reagent formed in situ by addition of 2-(2-bromo-ethyl)-[1,3]dioxane to a mixture comprising magnesium and the compound of the formula (VII-1). In one embodiment, the mixture further comprises methyl magnesium chloride and/or methyl magnesium bromide in a solvent. Any exotherm formed from the reaction may be controlled by the rate of addition of the bromide.

The compound of the formula (VII-1) may be formed by coupling N,O-dimethylhydroxylamine hydrochloride and a compound of the formula (VIII-1)

(VIII-1)

This coupling reaction may be performed by mixed anhydride procedure. In one mixed anhydride procedure, compound VIII-1 is combined with methylene chloride and N-methylmorpholine is added followed by isobutyl chloroformate. In a separate mixture, a slurry of N,O-dimethylhydroxylamine hydrochloride is treated with N-methylmorpholine. The two reaction mixtures are combined and then quenched with a solution of citric acid in water. This procedure preferably operates at a temperature below about 20° C., more preferably below about 0° C.

Compounds of formula (V-1) may be used to produce compounds of the formula (IVa1-1) according to scheme 3:

Scheme 3

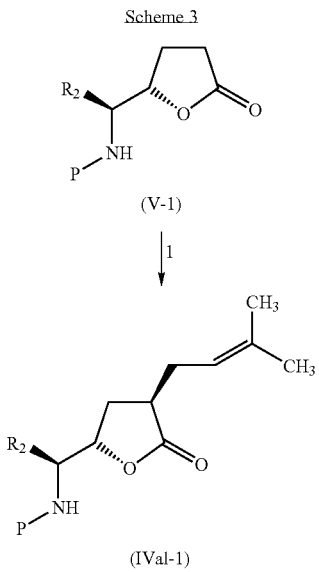

In step 1 of scheme 3, the compound of the formula (IVa1-1) may be formed by reacting 4-halo-2-methyl-2-butene and a compound of the formula (V-1) in the presence of a base. Exemplary bases include lithium dialkyl amides such as lithium N-isopropyl-N-cyclohexylamide, lithium bis(trimethylsilyl)amide, lithium di-isopropylamide, and potassium hydride. Suitable solvents include aprotic polar solvents such as ethers (such as tetrahydrofuran, glyme or dioxane), benzene, or toluene, preferably tetrahydrofuran. The aforesaid reaction is conducted at a temperature from about −78° C. to about 0° C., preferably at about −78° C. In one embodiment, alkylation of the lactone (V-1) is accomplished by reacting the lactone (V-1) with lithium bis(trimethylsilyl)amide and dimethylallyl bromide in tetrahydrofuran at a temperature from about −78° C. to about −50° C. Reaction times range from several hours or if an additive such as dimethyl imidazolidinone is present, the reaction may be complete in minutes.

Compounds of formula (IVa1-1) may be used to produce compounds of the formula (Ia-1) according to scheme 4:

Scheme 4

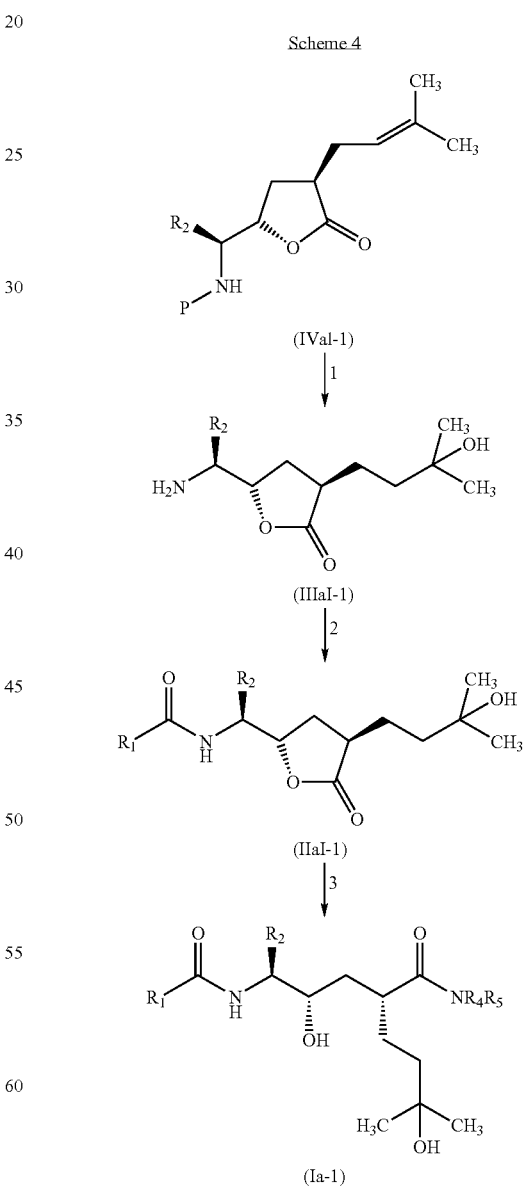

In step 1 of scheme 4, a compound of the formula (IIIa1-1) is formed by reacting a compound of the formula (IVa1-1)

with phosphoric acid. Preferably, this reaction occurs in any suitable solvent, such as non-alcoholic solvents. Two preferred solvents include tetrahydrofuran and dichloroethane. The reaction may take place at any suitable temperature, preferably from about −25° C. to about 120° C., more preferably from about 15° C. to about 40° C. Reaction time is dependent on temperature and batch size, amount other factors, but typically reaction time is from about 2 hours to about 14 hours.

Step 2 of scheme 4 depicts coupling a compound IIIa1-1 with a compound having the formula $R_1$—CO—X to form a compound having the formula (IIa1-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI), and diethylphosphorylcyanide. The coupling is conducted in an inert solvent, preferably an aprotic solvent, such as tetrahydrofuran, acetonitirile, dichloromethane, chloroform, or N,N-dimethylformamide. One preferred solvent is tetrahydrofuran. In one embodiment, quinoxaline acid is combined with CDI in anhydrous tetrahydrofuran and heated to provide the acyl imidazole. Compound IIIa1-1 is added to the acyl imidazole at room temperature to form the compound IIa1-1.

Step 3 of scheme 4 includes reacting the compound of formula IIa1-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa1-1 is dissolved in methanol which has been saturated with ammonia gas. In another embodiment, the compound IIa1-1 in methanol is treated with ammonium hydroxide in tetrahydrofuran at room temperature.

Scheme 5 represents an alternative method to form compounds of formula Ia-1 from compounds of formula IVa1-1.

Scheme 5

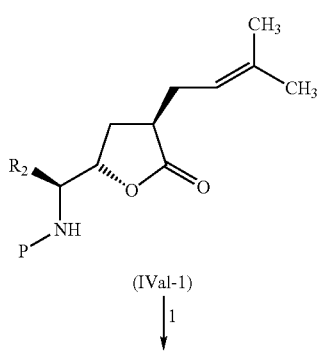

(IVa1-1)

↓ 1

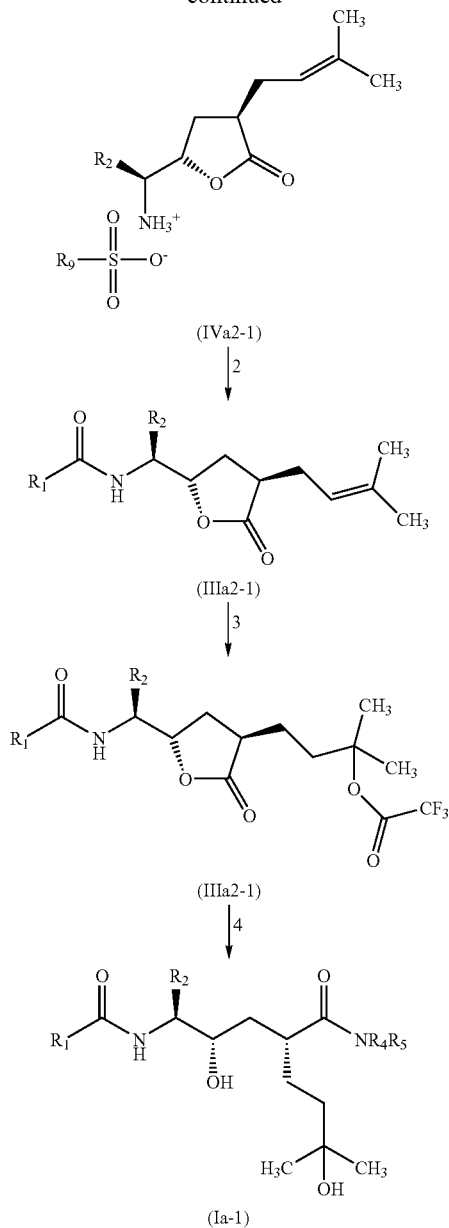

In step 1 of scheme 5, a compound of the formula (IVa1-1) is reacted with a compound of the formula $R_9$—$SO_2$—X to form a compound of the formula (IVa2-1). Any suitable acidic deprotection reaction may be performed. In one example, an excess of p-toluenesulfonic acid hydrate in ethyl acetate is introduced to the compound IVa1-1 at room temperature. Suitable solvents include ethyl acetate, alcohols, tetrahydrofuran, and mixtures thereof. The reaction may proceed at ambient or elevated temperatures. Typically, the reaction is substantially complete within two and twelve hours. The resulting compound IVa2-1 may be crystallized and separated from the reaction mixture, and may be further purified to remove impurities by recrystallization from hot ethyl acetate.

In step 2 of scheme 5, the compound IVa2-1 may be coupled with a compound having the formula $R_9$—CO—X to form a compound of the formula (IIIa2-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI)/dimethylaminopyridine (DMAP), and diethylphosphorylcyanide. The coupling is conducted in an inert solvent, preferably an aprotic solvent, such as acetonitirile, dichloromethane, chloroform, or N,N-dimethylformamide. One preferred solvent is methylene chloride. In one embodiment, quinoxaline acid is combined with methylene chloride, oxalyl chloride and a catalytic amount of N,N-dimethylformamide to form an acid chloride complex. The compound IVa2-1 is added to the acid chloride complex followed by triethylamine at a temperature from about 0° C. to about 25° C. to form the compound IIIa2-1.

Step 3 of scheme 5 includes reacting a compound IIIa2-1 with trifluoroacetic acid to produce a compound of the formula (IIIa2-1). In one embodiment, the hydration with trifluoroacetic acid occurs in methylene chloride solution at room temperature. The hydration may take several hours to complete at room temperature. A catalytic amount of sulfuric acid can be added to the reaction solution to increase the rate of reaction.

Step 4 of scheme 5 includes reacting the compound of formula IIa2-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa2-1 is dissolved in methanol which has been saturated with ammonia gas. In another embodiment, the compound IIa2-1 in methanol is treated with ammonium hydroxide in tetrahydrofuran at room temperature.

Solid Drug-Containing Dispersion

The drug is present in the composition in a solid drug/matrix dispersion comprising a low-solubility drug and a matrix. At least a major portion of the drug in the dispersion is amorphous. The term "a major portion" of the drug means that at least 60% of the drug is in amorphous form, rather than a crystalline form. Preferably, the drug in the dispersion is substantially amorphous. As used herein, "substantially amorphous" means that the amount of the drug in amorphous form is at least 80%. More preferably, the drug in the dispersion is "almost completely amorphous" meaning that the amount of drug in the amorphous form is at least 90% as measured by powder X-ray diffraction or differential scanning calorimetry ("DSC"), or any other standard quantitative measurement.

The amorphous drug may exist in the drug/matrix dispersion as a solid solution of drug homogeneously distributed throughout the dispersion, or a portion of the drug may exist in relatively drug-rich domains. Preferably, the solid dispersion is substantially homogeneous so that the amorphous drug is dispersed as homogeneously as possible throughout the dispersion. As used herein, "substantially homogeneous" means that the amount of the drug present in drug-rich amorphous domains within the dispersion is less than 20%. Preferably, the dispersion is "completely homogeneous," meaning that the amount of drug in drug-rich domains is less than 10%.

While the dispersion may have some drug-rich domains, it is preferred that the dispersion itself have a single glass-transition temperature ($T_g$). Alternatively, the $T_g$ of the dispersion is at least 3° C. greater than the $T_g$ of the drug alone. This contrasts with a simple physical mixture of amorphous drug particles and matrix particles which, when the matrix is amorphous, generally displays two distinct $T_g$s, one that of the drug and one that of the matrix. When the matrix is not amorphous or does not have a $T_g$, the $T_g$ of the simple physical mixture generally has the same $T_g$ of pure amorphous drug particles alone. $T_g$ as used herein is the characteristic temperature where a glassy material, upon gradual heating, undergoes a relatively rapid (e.g., 10 to 100 seconds) physical change from a glass state to a rubber state. The $T_g$ of the dispersion may be measured by differential scanning calorimetry ("DSC"), or any other standard quantitative measurement. Dispersions of the present invention that are substantially homogeneous generally are more physically and chemically stable and, when mixed with concentration-enhancing polymers, have improved concentration-enhancing properties, and in turn improved bioavailability, relative to nonhomogeneous dispersions.

The solid dispersion also includes one or more components in addition to the drug, which are collectively referred to as the "matrix." The matrix is selected such that the dispersion provides either improved physical stability, improved chemical stability, improved concentration-enhancement, or any combination of these or all three for the drug as compared to undispersed amorphous drug alone. By "undispersed drug" is meant drug that is not dispersed in the matrix. The matrix may comprise a single component or it may be a mixture of two or more components. The components may be intimately mixed to form a single phase or molecular dispersion or they may exist as two or more distinct phases with differing compositions.

At least a portion of the matrix is either water swellable, dispersible, or soluble in aqueous solution at physiologically relevant pH (e.g., pH 1-8). The matrix as a whole should be a solid at room temperature, and remain substantially solid up to a temperature of at least about 40° C., preferably up to a temperature of at least about 60° C., and more preferably up to a temperature of at least about 70° C. In order to achieve this, the matrix should be comprised of at least one or more components with a melting point above about 40° C., preferably above about 60° C., and more preferably above about 70° C.

The amount of matrix relative to the amount of drug present in the dispersion of the present invention depends on the drug and matrix and may vary widely from a drug-to-matrix weight ratio of from 0.01 to about 4 (e.g., 1 wt % drug to 80 wt % drug). This will vary dependent on the dose of the drug. When the dose is low, less than about 50 mg, the drug-to-matrix weight ratio can be quite small, even less than 0.01. In general, when the dose is relatively high, that is greater than about 50 mg, the drug-to-matrix ratio may be as high as 4.

The components used in the matrix may be polymeric or non-polymeric, and may comprise a mixture of several components. Thus the matrix may comprise a mixture of polymeric components, a mixture of non-polymeric components, or a mixture of polymeric and non-polymeric components.

The term "polymeric" is used conventionally, meaning a compound that is made of monomers connected together to form a larger molecule. A polymeric component generally consists of at least about 20 monomers. Thus, the molecular weight of a polymeric component will generally be about 2000 daltons or more. Polymeric matrix components generally will result in dispersions with improved concentration enhancement relative to non-polymeric matrix components. Exemplary polymeric components for use as the matrix include polyethylene glycols, polyoxyethylene glycols, polyethylene-propylene glycol copolymers, polyethylene oxides, polyvinyl pyrrolidinone (also referred to as polyvinyl pyrrolidone or povidone or PVP), polyvinyl alcohol, polyethylene-vinyl alcohol copolymers, polyvinyl alcohol polyvinyl acetate copolymers, xanthan gum, carrageenan, hydroxypropyl cellulose, hydroxypropyl methyl cellulose, carboxy methyl cellulose, carboxylic acid-functionalized polymethacrylates, amine-functionalized polymethacrylates, chitosan, chitin, polydextrose, dextrin and starch. Also included within this definition are high molecular weight proteins such as gelatin and albumin.

Examples of polyethylene glycols and polyoxyethylene glycols include the CARBOWAX7 polymers supplied by Union Carbide (Danbury, Conn.) and the LUTROL E® polymers supplied by BASF (Mount Olive, N.J.). Examples of polyethylene oxide include POLOX® supplied by Union Carbide. Examples of polyvinyl pyrrolidinones include the KOLLIDON® polymers supplied by BASF. Examples of polyvinyl alcohols and polyvinyl alcohol polyvinyl acetate copolymers include the ELVANOL® polymers supplied by DuPont Industrial Polymers (Wilmington, Del.). Examples of polyethylene-vinyl alcohol copolymers include the EVAL® polymers supplied by EVALCA (Lisle, Ill.). Examples of xanthan gums include the KETROL® polymers supplied by Monsanto Pharmaceutical Ingredients (St. Louis, Mo.). Examples of carrageenans include the GELCAREN® polymers supplied by FMC (Philadelphia, Pa.). Examples of hydroxypropyl cellulose include the KLUCEL® polymers supplied by Aqualon Division of Hercules (Wilmington, Del.). Examples of hydroxypropyl methyl cellulose include the MethocelJ polymers manufactured by Dow Chemical (Midland, Mich.). Examples of carboxymethyl cellulose include the AKUCEL® polymers supplied by Robeco Inc. (New York, N.Y.). Examples of carboxylic acid-functionalized polymethacrylates and amine-functionalized polymethacrylates include the EUDRAGITS® supplied by Röhm America Inc. (Piscataway, N.J.). Examples of polydextrose include the LITESSE® polymers supplied by Cultor Food Science (Ardsley, N.Y.).

By "non-polymeric" is meant that the component is not polymeric. Exemplary non-polymeric materials for use as a matrix component include: alcohols, such as stearyl alcohol and cetyl alcohol, organic acids, such as stearic acid, citric acid, fumaric acid, tartaric acid, and malic acid; organic bases such as glucosamine, N-methylglucamine, tris(hydroxymethyl)amino methane, and dodecylamine; salts such as sodium chloride, potassium chloride, lithium chloride, calcium chloride, magnesium chloride, sodium sulfate, potassium sulfate, sodium carbonate, and magnesium sulfate; amino acids such as alanine and glycine; sugars such as glucose, sucrose, xylitol, fructose, lactose, mannitol, sorbitol, and maltitol; fatty acid esters such as glyceryl (mono- and di-) stearates, glyceryl (mono- and di-) behenates, triglycerdes, sorbitan monostearate, saccharose monostearate, glyceryl (palmitic stearic) ester, polyoxyethylene sorbitan fatty-acid esters; waxes, such as microcrystalline wax, paraffin wax, beeswax, synthetic wax, castor wax, and carnauba wax; alkyl sulfates such as sodium lauryl sulfate and magnesium lauryl sulfate; and phospholipids, such as lecithin.

Non-polymeric components have several advantages. Such components are generally easier to purify relative to polymeric components, thus decreasing the amount of unwanted impurities that may react with the drug. Non-polymeric components also tend to have a higher solubility in an environment of use, resulting in faster dissolution of the drug/matrix dispersion. In addition, use of non-polymeric components may result in simpler processes for forming the drug/matrix dispersion. For example, in thermal-based processes, non-polymeric components generally have sharper melting points, lower melt viscosities, and faster congealing rates than polymeric components. In solvent-based processes, non-polymeric components are generally more soluble and often result in lower viscosity solutions than polymeric components. In addition, where the matrix comprises a blend of non-polymeric and polymeric components, it is preferred in some embodiments for the non-polymeric component to comprise at least 10 wt % of the matrix.

Non-polymeric components often have a lower molecular weight compared to polymeric components, and thus often have the ability to increase the solubility of the drug in the matrix. As discussed below, this tends to improve the stability of the drug in the matrix. The non-polymeric component may comprise even greater amounts of the matrix, from 25 wt % to 50 wt % or more.

Dispersions of the drug and matrix may be made according to any known process which results in a dispersion with the properties described previously. Such processes include mechanical, thermal and solvent processes. Exemplary mechanical processes include milling and extrusion; melt processes include high temperature fusion, solvent modified fusion and melt-congeal processes; and solvent processes include non-solvent precipitation, spray coating and spray-drying. Often, processes may form the dispersion by a combination of two or more process types. For example, when an extrusion process is used the dispersion may be operated at an elevated temperature such that both mechanical (shear) and thermal means (heat) are used to form the dispersion. See, for example, U.S. Pat. Nos. 4,801,460, 5,456,923 and 5,939,099 which describe formation of dispersions via extrusion processes; U.S. Pat. Nos. 5,340,591 and 4,673,564 which describe forming dispersions by milling processes; and U.S. Pat. Nos. 5,707,646 and 4,894,235 which describe the formation of dispersions via melt/congeal processes, the disclosures of which are incorporated by reference.

In one embodiment, the dispersion is formed by a thermal process, such as an extrusion process, a fusion process, or a melt-congeal process. In such cases, the matrix is selected such that it is suitable for use in the thermal process. Generally, it is desirable to keep the processing temperature as low as possible to avoid thermal degradation of the drug. As such, it is preferred that the matrix as a whole become fluid at a temperature of less than about 200° C., more preferably less than about 160° C., and most preferably less than about 120° C. A matrix that becomes fluid at a higher temperature than this should only be used with drugs that are thermally stable at the required processing temperature.

Exemplary materials that are suitable for use as a matrix component for thermal processes include: alcohols, such as stearyl alcohol and cetyl alcohol, organic acids, such as stearic acid, citric acid, and malic acid; sugars such as glucose, xylitol, sorbitol, and maltitol; fatty acid esters such as mono-, di-, and tri-glycerides, glyceryl mono-, di-, and tri-stearates, glyceryl mono-, di-, and tri-behenates, sorbitan monostearate, saccharose monostearate, glyceryl (palmitic stearic) ester, polyoxyethylene sorbitan fatty-acid esters; waxes, such as microcrystalline wax, paraffin wax, beeswax, synthetic wax, castor wax, and carnauba wax; alkyl sulfates such as sodium lauryl sulfate; and polymers such as polyethylene glycols, polyoxyethylene glycols, polyethylene-propylene glycol copolymers, poloxamers, polyethylene oxide, polyvinyl pyrrolidinone (also referred to as polyvinyl pyrrolidone or povidone or PVP), polyvinyl alcohol, polyethylene-vinyl alcohol copolymers, polyvinyl alcohol polyvinyl acetate copolymers, carboxylic acid-functionalized polymethacrylates, and amine-functionalized polymethacrylates. While specific materials have been discussed as being suitable for use alone in the dispersions formed by thermal processing, blends of materials may also be suitable. For example, a water-insoluble matrix component such as microcrystalline wax may be blended with a highly water soluble matrix component, such as a poloxamer, to form a water-dispersible matrix.

The matrix may include a plasticizer as one component of the matrix to reduce processing temperature. Exemplary plasticizers include mineral oils, petrolatum, lanolin alcohols, polyethylene glycol, polypropylene glycol, sorbitol, triethanol amine, benzyl benzoate, dibutyl sebacate, diethyl phthalate, glyceryl monostearate, triacetin, and triethyl citrate. The amount of plasticizer used will depend on the melting point of the other matrix components and the desired processing temperature. Typically, the ratio of plasticizer to matrix will be 0.01 to 0.5, more typically 0.05 to 0.1. Solvents or swelling agents, such as water, alcohols, ketones, and the like may also be used to reduce processing temperature and improve the processability of the composition.

One preferred thermal process is an extrusion process. Here, the low-solubility drug and the one or more matrix components may be dry blended, with or without the addition of a plasticizer, and the blend fed to a twin-screw extrusion device. The low-solubility drug may be substantially amorphous prior to forming the blend, but this is not a requirement for the process. The twin-screw extrusion device is designed such that there is sufficient heat and mechanical energy (e.g., shear) to form a dispersion, without degradation of the drug or matrix. The processing temperature may vary from about 50° C. up to about 200° C., depending on the melting point of the drug and the matrix materials. Generally, the higher the melting point of the drug and the matrix components, the higher the processing temperature.

When the drug has a high solubility in the matrix, a lower amount of mechanical energy will be required to form the dispersion. In such cases, the processing temperature may be below the melting temperature of the undispersed amorphous drug but greater than the melting point of at least a portion of the matrix materials, since the drug will dissolve into the molten matrix.

When the drug has a low-solubility in the matrix, a higher amount of mechanical energy may be required to form the dispersion. Here, the processing temperature may need to be above the melting point of the drug and at least some of the matrix components. A high amount of mechanical energy may be needed to mix the molten drug with the matrix components to form a dispersion. Typically, the lowest processing temperature and an extruder design that imparts the lowest amount of mechanical energy (e.g., shear) that produce a satisfactory dispersion is chosen in order to minimize the exposure of drug to harsh conditions.

Another preferred method for forming dispersions is "solvent processing," which consists of dissolution of at least a portion of the drug and at least a portion of the one or more matrix components in a common solvent. The term "solvent" is used broadly and includes mixtures of solvents. "Common" here means that the solvent, which can be a mixture of compounds, will simultaneously dissolve at least a portion of the drug and the matrix material(s).

Exemplary materials that are suitable for use as a matrix component for solvent processing include alcohols, such as stearyl alcohol and cetyl alcohol, organic acids, such as stearic acid, citric acid, fumaric acid, tartaric acid, and malic acid; salts such as sodium chloride, potassium chloride, lithium chloride, calcium chloride, magnesium chloride, sodium sulfate, potassium sulfate, sodium carbonate, and magnesium sulfate; amino acids such as alanine and glycine; sugars such as glucose, sucrose, xylitol, fructose, lactose, mannitol, sorbitol, and maltitol; fatty acid esters such as glyceryl (mono- and di-) stearates, triglycerides, sorbitan monostearate, saccharose monostearate, glyceryl (palmitic stearic) ester, polyoxyethylene sorbitan fatty-acid esters; waxes, such as microcrystalline wax, paraffin wax, beeswax, synthetic wax, castor wax, and carnauba wax; alkyl sulfates such as sodium lauryl sulfate and magnesium lauryl sulfate; phospholipids, such as lecithin; proteins, such as gelatin and albumin; and polymers such as polyethylene glycols, polyoxyethylene glycols, polyethylene-propylene glycol copolymers, polyethylene oxides, polyvinyl pyrrolidinone (also referred to as polyvinyl pyrrolidone or povidone or PVP), polyvinyl alcohol, polyethylene-vinyl alcohol copolymers, polyvinyl alcohol polyvinyl acetate copolymers, xanthan gum, carrageenan, hydroxypropyl cellulose, hydroxypropyl methyl cellulose, carboxy methyl cellulose, carboxylic acid-functionalized polymethacrylates, amine-functionalized polymethacrylates, chitosan, chitin, polydextrose, and dextrin. While specific materials have been discussed as being suitable for use alone in the dispersions formed by solvent processing, blends of materials may also be suitable.

After at least a portion of each of the drug and matrix have been dissolved, the solvent is removed by evaporation or by mixing with a non-solvent. Exemplary processes are spray-drying, spray-coating (pan-coating, fluidized bed coating, etc.), and precipitation by rapid mixing of the drug and matrix solution with $CO_2$, hexane, heptane, water of appropriate pH, or some other non-solvent. Preferably, removal of the solvent results in a solid dispersion which is substantially homogeneous. To achieve this end, it is generally desirable to rapidly remove the solvent from the solution such as in a process where the solution is atomized and the drug and matrix rapidly solidify.

In one embodiment, the solvent is removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. In addition, at least a portion of the heat required for evaporation of solvent may be provided by heating the spray solution.

Solvents suitable for spray-drying can be water or any organic compound in which at least a portion of the drug and matrix are mutually soluble. Preferably, the solvent is also volatile with a boiling point of about 150° C. or less. In addition, the solvent should have relatively low toxicity and be removed from the dispersion to a level that is acceptable according to The International Committee on Harmonization (ICH) guidelines. Removal of solvent to this level may require a processing step such as tray-drying subsequent to the spray-drying or spray-coating process. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Mixtures, particularly mixtures of an organic solvent such as methanol, ethanol or acetone and water are often desirable. Lower volatility solvents such as dimethyl acetamide or dimethylsulfoxide can also be used. Mixtures of solvents, such as 50% methanol and 50% acetone, can also be used, as can mixtures with water as long as at least a portion of the matrix and drug are sufficiently soluble to make the spray-drying process practicable.

Generally, the temperature and flow rate of the drying gas is chosen so that the drug/matrix-solution droplets are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 μm to 500 μm in diameter, with 5 to 100 μm being more typical. The large surface-to-volume ratio of the droplets and the large driving force for evaporation of solvent leads to actual drying times of a few seconds or less, and more typically less than 0.1 second. This rapid drying is often critical to the particles maintaining a uniform, homogeneous dispersion instead of separating into drug-rich and matrix-rich phases. Solidification times should be less than 100 seconds, preferably less than a few seconds, and more preferably less than 1 second. In general, to achieve this rapid solidification of the drug/matrix solution, it is preferred that the size of droplets formed during the spray-drying process are less than about 100 μm in diameter. The resultant solid particles thus formed are generally less than about 100 μm in diameter.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of drug molecules in the dispersion, thereby improving its stability. Generally, the solvent content of the dispersion as it leaves the spray-drying chamber should be less than 10 wt % and preferably less than 2 wt %. In some cases, it may be preferable to spray a solvent or a solution of a stabilizer or other excipient into the spray-drying chamber to form granules, so long as the dispersion is not adversely affected.

Spray-drying processes and spray-drying equipment are described generally in Perry's Chemical Engineers' Handbook, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 Chem. Eng. Prog. Monogr. Series 2 (1954).

In addition, the matrix may include optional additional components, such as surfactants, pH modifiers, disintegrants, binders, lubricants, etc.

Improved Drug Stability

In one aspect of the invention, the low-solubility drug in the composition of drug/matrix dispersion and concentration-enhancing polymer may improve stability relative to the drug in a control composition. The improved stability may be either physical, chemical, or both. When evaluating chemical stability, the control composition may be either the drug in undispersed amorphous form mixed with an equivalent amount of concentration-enhancing polymer, or may be a dispersion of the drug and concentration-enhancing polymer. When evaluating physical stability, the control composition is the undispersed amorphous drug.

In one aspect, the drug in the dispersion has improved physical stability relative to a control composition. By improved physical stability is meant that the drug dispersed in the matrix remains amorphous or noncrystalline, or at least crystallizes more slowly, than the control composition. This increased physical stability may arise by forming a dispersion which is either thermodynamically stable or kinetically stable.

Thermodynamically stable dispersions may be formed by selecting the matrix and drug/matrix ratio such that at least a major portion of the drug is dissolved in the matrix at a particular set of conditions of temperature and relative humidity. At least a "major portion" means at least 60 wt % of the drug is dissolved. More preferably at least 80% of the drug is dissolved, and even more preferably at least 90% of the drug is dissolved in the matrix. In such cases, the drug/matrix dispersion may be said to be "thermodynamically stable" (under a particular set of conditions) and thus the drug remains indefinitely dissolved in the matrix as long as it is stored under the appropriate conditions.

That is, the free energy of the drug in the drug/matrix dispersion is less than the free energy of the drug in the crystalline form. Under such conditions, the dispersion may be a solid solution of amorphous drug in the matrix. The solubility of drug in the matrix is a function of the temperature and water content of the drug/matrix dispersion. The drug/matrix dispersion must be stored at an appropriate temperature and relative humidity for the drug to remain soluble in the matrix. As used herein, thermodynamically stable drug/matrix dispersions are those which are thermodynamically stable under conventional storage conditions, that is, from 25° C. to 50° C. and from 20% to 75% relative humidity.

For thermodynamically stable drug/matrix dispersions, the matrix component is chosen to complement the physical characteristics of the drug to result in improved solubility of the drug in the matrix. Comparison of physical properties of the drug and matrix materials, such as the hydrophilic-lipophilic balance (HLB), solubility parameter, or log P value, can be used to select suitable matrix components for use with a specific drug to obtain a thermodynamically stable dispersion. For example, when the drug is relatively hydrophobic, at least a portion of the matrix should be relatively hydrophobic. Exemplary hydrophobic matrix components include glycerides, fatty acids, and fatty alcohols. If the drug is relatively hydrophilic, preferably at least a portion of the matrix should be hydrophilic. Exemplary hydrophilic matrix components include organic acids, short-chain monoglycerides, short-chain fatty acids, sugars, polydextrose, polyvinyl pyrrolidinone (also referred to as polyvinyl pyrrolidone or povidone or PVP), polyethylene oxides, and polyethylene glycols. In general, the drug/matrix ratio will depend on the particular drug and matrix. Where the drug is completely miscible in the matrix, the drug/matrix ratio may be any value. Where the drug is not completely miscible in the matrix, the concentration of drug in the matrix should be less than the nucleation concentration. This is typically about 1.5- to 3-fold the solubility of the drug in the matrix. Thus, it is preferred that the matrix is chosen so that the solubility of the drug in the matrix is at least 30%, and more preferably at least 50%, of the concentration of the drug in the matrix.

Alternatively, where the drug content in the dispersion exceeds the drug solubility in the matrix, the dispersion may nonetheless be "kinetically stable," even though the dispersion is not thermodynamically stable. By "kinetically stable" is simply meant that even though the free energy of the drug is lower in the crystalline form than in the drug/matrix dispersion, the matrix interferes with the ability of the drug to crystallize. Kinetic stability may arise from a variety of mechanisms, including (1) simple dilution of the drug in the matrix so that the distance between adjacent drug molecules is increased relative to a control composition; (2) reduced mobility such that the diffusion rate of drug in the matrix is less than the diffusion rate of drug in a control composition; and (3) interaction of the drug and matrix such that the nucleation or growth of drug crystals is inhibited.

Dispersions which are kinetically stable due to dilution may be formed by simply forming a dilute homogeneous dispersion. Thus, the processing conditions should be chosen to result in a dispersion that is at least substantially homogeneous, and more preferably completely homogeneous. For example, a thermal process may be used in which the drug is soluble in the matrix at the processing temperature (e.g., in a thermal process such as melt-congeal), and then rapidly solidified by cooling. Generally, stability is improved as the drug/matrix ratio decreases. Preferably, the drug/matrix ratio is 20 or less, and more preferably is 10 or less.

Kinetically stable drug/matrix dispersions may also be formed by reducing the mobility of the drug in the dispersion. Drug mobility may be reduced by selecting the matrix components such that the $T_g$ of the resulting drug/matrix dispersion is higher than that of the control composition. Exemplary matrix components having relatively high $T_g$ values include hydroxy propyl methyl cellulose, hydroxypropyl cellulose, polyvinyl pyrrolidone, maltodextrin, polydextrose, starch, dextrin, and trehalose. In general, $T_g$ increases with increasing molecular weight. Thus, for example, saccharide oligomers (such as maltodextrin, polydextrose, starch, and dextrin) generally have a higher $T_g$ than tri-saccharides (such as trehalose), which in turn are higher than di-saccharides (such as sucrose and lactose), which in turn are higher than monosaccharides (such as glucose).

When kinetic stability is achieved due to a high $T_g$ value, the matrix and drug content of the dispersion should be chosen such that the $T_g$ of the resulting dispersion, when equilibrated with humid air having a relative humidity of about 50%, is at least 30° C., and preferably greater than about 50° C. Preferably, a substantially homogeneous dispersion of the drug and matrix is formed. Even more preferably, the $T_g$ of the matrix material should be sufficiently high such that the $T_g$ of the resulting dispersion is greater than about 70° C., more preferably greater than about 75° C., and most preferably greater than about 100° C.

Kinetically stable drug/matrix dispersions may also be formed by inhibiting crystallization, either by inhibiting nucleation, crystal growth, or both. Generally, to be a crystallization inhibitor, the matrix must result in a strong drug/matrix interaction. The matrix is chosen to have a "complementary" chemical interaction with the drug. Examples of such complementary chemical interactions are given below.

| Drug Property | Complementary Matrix Property |
|---|---|
| Cationic | Anionic |
| Anionic | Cationic |
| Electron donor | Electron acceptor |
| Electron acceptor | Electron donor |
| Hydrogen-bonding donor | Hydrogen-bonding acceptor |
| Hydrogen-bonding acceptor | Hydrogen-bonding donor |

The complementary chemical interaction between drug and matrix lowers the free energy of the drug in the vicinity of the matrix and inhibits the formation of drug-rich areas.

In other instances, the matrix is chosen such that the interaction is not chemically complementary but still results in a strong physical drug/matrix interaction. Examples of such physical interactions include (1) if the drug is polar, select the matrix to be polar; and (2) if the drug is hydrophobic, select the matrix to be hydrophobic. These physical interactions lower the free energy of the drug in the matrix.

Since kinetic stability may be achieved through one or more mechanisms, the matrix may be selected to reduce the rate of crystallization of the drug through one or more mechanisms. For example, a matrix may be selected that has a high $T_g$ (to reduce mobility), that has a complementary property relative to the drug (to inhibit crystallization), and is capable of being processed to yield a homogeneous dispersion having a low drug/matrix ratio (dilution).

The physical stability of the drug in the matrix may be evaluated by measuring the rate of change in the physical state of the drug from amorphous to crystalline in the matrix and comparing the rate to the corresponding rate of change provided by a control composition. The control composition is undispersed amorphous drug alone. The rate of change may be measured by determining the fraction of drug in the crystalline state in the matrix or control over time. This may be measured by any standard physical measurement, such as X-ray diffraction, DSC, solid state NMR or Scanning Electron Microscope ("SEM") analysis. Physically stable compositions of the present invention will crystallize at a slower rate than a control composition. Preferably, the rate of crystallization of the drug in the drug/matrix dispersion is less than 90%, and more preferably less than 80%, of the rate of crystallization of a control composition.

In another aspect of the invention, the matrix is selected such that the drug in the dispersion has improved chemical stability compared with a control composition. The control composition may be either the drug in the undispersed amorphous form (that is, not dispersed in a matrix material) mixed with the concentration-enhancing polymer, or the control may be a dispersion of the drug in concentration-enhancing polymer. As used herein, "chemical stability" refers to the rate of chemical degradation of the drug in a typical storage environment. Types of degradation reactions that can occur include, but are not limited to hydrolysis, lactonization, esterification, oxidation, reduction, ring cyclization, and transesterification. Dispersing the drug in the matrix preferably results in a reduced rate of degradation of the amorphous drug in the dispersion relative to at least one, and preferably both, of the controls described above.

In general, drug degradation may be measured using any conventional method for measuring the purity or potency of drug in a pharmaceutical composition. For example, the amount of active drug present in a dispersion may be initially measured using high-performance liquid chromatography (HPLC) or other analytical techniques well known in the art. Alternatively, the amount of drug initially present may be calculated from the amount of drug present in the dispersion formulation. The potency of the dispersion is then measured after storage at controlled temperature and humidity conditions for an appropriate period of time. A decrease in potency indicates that a chemical reaction has occurred, leading to a decrease in the amount of active drug present in the dispersion, and is an indication of poor chemical stability.

An alternative method used to evaluate chemical stability is to analyze the rate of increase in the amount of drug degradant(s) in the dispersion, which would indicate reaction of the drug. An HPLC or other analytical technique may be used to determine the concentration of drug degradant(s) in a dispersion. The amount of the degradant(s) is measured before and after storage under controlled storage conditions. The amount of increase in the drug degradant(s) may be used to determine the amount of decrease in percent "purity of the drug." The "percent drug purity" is defined as 100 times the total amount of drug present divided by the total amount of drug initially present. Thus, percent drug purity may be calculated by the formula $$\text{wt \% drug purity} = \left(\frac{\text{total amt. of drug present}}{\text{total amt. of drug init. present}}\right) * 100$$

When the drug purity is calculated from the total amount of impurities, "percent drug purity" may be calculated by assuming that the "total amount of drug initially present," given in wt %, is equal to 100 wt % minus the wt % of total initial impurities, and that "total amount of drug present" is equal to 100 wt % minus the wt % of total impurities after storage, that is, at some later time. This method is equivalent to calculating "percent drug purity" by the formula:

$$\text{wt \% drug purity} = \left[1 - \left(\frac{\text{total amt. of impurities present}}{\text{total amt. of drug init. present}}\right)\right] * 100$$

The rate at which drug degradation occurs is generally dependent on the storage conditions. The drug, when formulated as a composition of the present invention, should be stable at ambient temperature and humidity conditions (e.g., relative humidities of 20% to 60%) for long periods of time, such as months or years. However, to expedite testing, the storage conditions may employ elevated temperature and/or humidity to simulate longer storage times at ambient conditions. The storage time may vary from a few days to weeks or months, depending on the reactivity of the drug and the storage conditions.

A "degree of degradation" of drug following storage may be determined by subtracting the final drug percent purity (either determined by measuring the decrease in drug present or an increase in the amount of drug degradants present) from the initial percent purity. For example, for a dispersion initially containing 100 mg drug, and no measurable impurities it would have an initial percent purity of 100 wt %. If, after storage, the amount of drug in the dispersion decreases to 95 mg, the final percent purity would be 95 wt % and the "degree of degradation" is 5 wt % (100 wt %-95 wt %). Alternatively, if 100 mg of drug substance were found to initially have 1 mg of impurities present, it would have an initial "percent purity" of 99 wt %. If, after storage, the total impurities present had increased to 6 wt %, the final percent purity would be 94 wt % and the "degree of degradation" would be 5 wt % (99 wt %-94 wt %).

Alternatively, "degree of degradation" can be determined by subtracting the amount of one or more specific drug degradants initially present from the amount of that specific degradant present after storage. Such a measure is useful where there are several drug degradants, of which only one (or a few) is of concern. The degree of degradation may be calculated on the basis of only those degradants that are of concern, rather than all of the degradants. For example, if a drug initially contained a specific degradant at a concentration of 1 wt % and after storage the concentration of that degradant was 6 wt %, the degree of degradation would be 5 wt % (6 wt %-1 wt %).

A relative degree of improvement in chemical stability may be determined by taking the ratio of the degree of degradation of the drug in a control composition and the degree of degradation of the drug in a test composition of the present invention under the same storage conditions for the same storage time period. The test composition is simply the drug/matrix dispersion mixed with the concentration-enhancing polymer. The control composition may be either amorphous drug alone mixed with concentration-enhancing polymer, or may be a dispersion of the drug and concentration-enhancing polymer (that is, the concentration-enhancing polymer replaces the matrix of the dispersion in the test composition). For example, where the degree of degradation of a drug in a test composition comprised of the drug and matrix is 1 wt %, and the degree of degradation of a control dispersion of drug and concentration-enhancing polymer is 50 wt %, the relative degree of improvement is 50 wt %/1 wt %, or 50. For dispersions of drugs and matrix of this aspect of the present invention, the relative degree of improvement is at least 1.25. When the drug is particularly unstable, larger relative degrees of improvement may be necessary in order for the chemical stability of the dispersion to be pharmaceutically acceptable. In such cases, the invention provides greater chemical stability when the relative degree of improvement is at least about 2, preferably at least about 5, and even more preferably at least 10. In fact, some dispersions may achieve a relative degree of improvement greater than 100.

The particular storage conditions and time of storage may be chosen as convenient depending on the stability of the drug, the particular concentration-enhancing polymer, and the ratio of drug to concentration-enhancing polymer. Where the drug is particularly unstable, or where the dispersion has a low ratio of drug to polymer, then shorter storage time periods may be used. Where the rate of drug degradation is linear, the relative degree of improvement will be independent of the storage time. However, where the rate of drug degradation is non-linear under controlled storage conditions, the stability test used to compare the test composition with the control composition is preferably chosen such that the degree of degradation is sufficiently large that it may be accurately measured. Typically, the time period is chosen so as to observe a degree of degradation of at least 0.1 wt % to 0.2 wt %. However, the time period is not so long that the ratio of drug to polymer changes substantially. Typically, the time period is such that the observed degree of degradation for the test composition is less than 50 wt % and preferably less than 20 wt %. When the rate of drug degradation in the control composition is relatively slow, the test is preferably conducted over a long enough period of time under controlled storage conditions to allow a meaningful comparison of the stability of the test composition with the control dispersion.

A stability test which may be used to test whether a composition meets the chemical stability criteria described above is storage of the test composition and the control composition for six months at 40° C. and 75% RH. A relative degree of improvement may become apparent within a shorter time, such as three to five days, and shorter storage times may be used for some drugs. When comparing compositions under storage conditions which approximate ambient conditions, e.g., 25° C. and 60% RH, the storage period may need to be from several months up to two years.

In addition, it is preferred that the compositions comprising drug and matrix result in drug stability such that the drug has a degree of degradation of less than about 2 wt %, more preferably less than about 0.5 wt %, and most preferably less than about 0.1 wt % when stored at 40° C. and 75% RH for six months, or less than about 2 wt %, more preferably less than about 0.5 wt %, and more preferably less than about 0.1 wt %, when stored at 25° C. and 60% RH for one year, or less than about 2 wt %, more preferably less than about 0.5 wt %, and more preferably less than about 0.1 wt %, when stored at ambient conditions for two years. Nevertheless, the compositions of the present invention may have a degree of degradation that is much greater than the preferred values, so long as the test composition achieves the degree of improvement relative to a control composition as described above.

Dispersing the drug in a suitable matrix can result in improved chemical stability of the drug by many possible mechanisms. For example, improved chemical stability of the drug may occur by isolating the drug from potential reactants, reducing the mobility of the drug, and hence, the rate of reaction of the drug, or both. In such cases the matrix should be selected such that it preferably does not react with, or catalyze reactions with the drug or if it does, such a reaction should be acceptably slow. In addition, the matrix should be selected such that any degradation products of the matrix material itself are not reactive with the drug. The matrix should also not contain unacceptably high levels of impurities that could lead to degradation of the drug.

Many of the matrix materials listed above for formation of dispersions may be suitable for use in forming chemically stable dispersions, depending on the nature and reactivity of the drug. Those skilled in the art will recognize that selection of a matrix for formation of chemically stable dispersions will require selecting the matrix in light of the particular chemical nature of the drug so that the dispersion will provide the appropriate chemical stability. For example, where the drug is acid-sensitive, the matrix should be either neutral or basic.

The compositions of the present invention are particularly useful where the drug reacts with the concentration-enhancing polymer. For example, the present invention may be used where the drug is acid-sensitive and it is desired to use an acidic concentration-enhancing polymer. Often acidic concentration-enhancing polymers are preferred because such polymers often result in superior aqueous concentration of the drug in the use environment. However, the acidic polymers may adversely interact with the drug, especially if the drug is dispersed in the acidic polymer. Accordingly, the present invention solves this problem by forming a dispersion with a relatively non-reactive, neutral matrix to chemically stabilize the drug. For example, the acid-sensitive drug may be dispersed in a neutral wax or alcohol or a neutral polymer such as a polyethylene oxide, polyethylene glycol, or polyvinyl pyrrolidinone (PVP). The dispersion may then be mixed with an acidic concentration-enhancing polymer, resulting in a dispersion that has improved chemical stability relative to either a simple physical mixture of the undispersed amorphous drug and concentration-enhancing polymer or a dispersion of the drug and concentration-enhancing polymer.

Concentration-Enhancing Polymers

The composition also includes a concentration-enhancing polymer. By "concentration-enhancing" is meant a polymer present in a sufficient amount so that composition provides, at a minimum, either improved AUC, maximum drug concentration, or relative bioavailability relative to a control consisting of an equivalent amount of crystalline drug but with no concentration-enhancing polymer. Concentration-enhancing polymers suitable for use in the various aspects of the present invention should be pharmaceutically acceptable, and should have at least some solubility in aqueous solution at physiologically relevant pHs (e.g. 1-8). Almost any neutral or ionizable polymer that has an aqueous-solubility of at least 0.1 mg/mL over at least a portion of the pH range of 1-8 may be suitable.

It is preferred that the concentration-enhancing polymers be "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution. A particularly preferred class of amphiphilic polymers are those that are ionizable, the ionizable portions of such polymers, when ionized, constituting at least a portion of the hydrophilic portions of the polymer. For example, while not wishing to be bound by a particular theory, such polymer/drug assemblies may comprise hydrophobic drug clusters surrounded by the concentration-enhancing polymer with the polymer=s hydrophobic regions turned inward towards the drug and the hydrophilic regions of the polymer turned outward toward the aqueous environment. Alternatively, depending on the specific chemical nature of the drug, the ionized functional groups of the polymer may associate, for example, via ion pairing or hydrogen bonds, with ionic or polar groups of the drug. In the case of ionizable polymers, the hydrophilic regions of the polymer would include the ionized functional groups. In addition, the repulsion of the like charges of the ionized groups of such polymers (where the polymer is ionizable) may serve to limit the size of the polymer/drug assemblies to the nanometer or submicron scale. Such drug/concentration-enhancing polymer assemblies in solution may well resemble charged polymeric micellar-like structures. In any case, regardless of the mechanism of action, the inventors have observed that such amphiphilic polymers, particularly ionizable cellulosic polymers such as those listed below, have been shown to interact with drug so as to maintain a higher concentration of drug in an aqueous use environment.

One class of polymers suitable for use with the present invention comprises non-ionizable (neutral) non-cellulosic polymers. Exemplary polymers include: vinyl polymers and copolymers having at least one substituent selected from the group consisting of hydroxyl, alkylacyloxy, and cyclicamido; polyvinyl alcohols that have at least a portion of their repeat units in the unhydrolyzed (vinyl acetate) form; polyvinyl alcohol polyvinyl acetate copolymers; polyvinyl pyrrolidone; and polyethylene polyvinyl alcohol copolymers.

A preferred class of neutral non-cellulosic polymers are comprised of vinyl copolymers of at least one hydrophilic, hydroxyl-containing repeat unit and at least one hydrophobic, alkyl- or aryl-containing repeat unit. Such neutral vinyl copolymers are termed "amphiphilic hydroxyl-functional vinyl copolymers." Amphiphilic hydroxyl-functional vinyl copolymers are believed to provide high concentration enhancements due to the amphiphilicity of these copolymers which provide both sufficient hydrophobic groups to interact with the hydrophobic, low-solubility drugs and also sufficient hydrophilic groups to have sufficient aqueous solubility for good dissolution. The copolymeric structure of the amphiphilic hydroxyl-functional vinyl copolymers also allows their hydrophilicity and hydrophobicity to be adjusted to maximize performance with a specific low-solubility drug.

The preferred copolymers have the general structure:

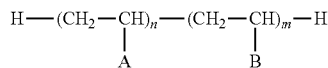

wherein A and B represent "hydrophilic, hydroxyl-containing" and "hydrophobic" substituents, respectively, and n and m represent the average number of hydrophilic vinyl repeat units and average number of hydrophobic vinyl repeat units respectively per polymer molecule. Copolymers may be block copolymers, random copolymers or they may have structures anywhere between these two extremes. The sum of n and m is generally from about 50 to about 20,000 and therefore the polymers have molecular weights from about 2,500 to about 1,000,000 daltons.

The hydrophilic, hydroxyl-containing repeat units, "A," may simply be hydroxyl (—OH) or it may be any short-chain, 1 to 6 carbon, alkyl with one or more hydroxyls attached thereto. The hydroxyl-substituted alkyl may be attached to the vinyl backbone via carbon-carbon or ether linkages. Thus, exemplary "A" structures include, in addition to hydroxyl itself, hydroxymethyl, hydroxyethyl, hydroxypropyl, hydroxymethoxy, hydroxyethoxy and hydroxypropoxy.

The hydrophobic substituent, "B," may simply be: hydrogen (—H), in which case the hydrophobic repeat unit is ethylene; an alkyl or aryl substituent with up to 12 carbons attached via a carbon-carbon bond such as methyl, ethyl or phenyl; an alkyl or aryl substituent with up to 12 carbons attached via an ether linkage such as methoxy, ethoxy or phenoxy; an alkyl or aryl substituent with up to 12 carbons attached via an ester linkage such as acetate, propionate, butyrate or benzoate. The amphiphilic hydroxyl-functional vinyl copolymers of the present invention may be synthesized by any conventional method used to prepare substituted vinyl copolymers. Some substituted vinyl copolymers such as polyvinyl alcohol/polyvinyl acetate are well known and commercially available.

A particularly convenient subclass of amphiphilic hydroxyl-functional vinyl copolymers to synthesize are those where the hydrophobic substituent "B" comprises the hydrophilic substituent "A" to which an alkylate or arylate group is attached via an ester linkage to one or more of the hydroxyls of A. Such copolymers may be synthesized by first forming the homopolymer of the hydrophobic vinyl repeat unit having the substituent B, followed by hydrolysis of a portion of the ester groups to convert a portion of the hydrophobic repeat units to hydrophilic, hydroxyl-containing repeat units having the substituent A. For example, partial hydrolysis of the homopolymer, polyvinylbutyrate, yields the copolymer, vinylalcohol/vinylbutyrate copolymer for which A is hydroxyl (—OH) and B is butyrate (—OOC—CH$_2$—CH$_2$—CH$_3$).

For all types of copolymers, the value of n must be sufficiently large relative to the value of m that the resulting copolymer is at least partially water soluble. Although the value of the ratio, n/m varies depending on the identity of A and B, it is generally at least about 1 and more commonly about 2 or more. The ratio n/m can be as high as 200. When the copolymer is formed by hydrolysis of the hydrophobic homopolymer, the relative values of n and m are typically reported in "percent hydrolysis," which is the fraction (expressed as a percent) of the total repeat units of the copolymer that are in the hydrolyzed or hydroxyl form. The percent hydrolysis, H, is given as $$H = 100*\left(\frac{n}{n+m}\right)$$

Thus, vinylbutyrate/vinylalcohol copolymer (formed by hydrolysis of a portion of the butyrate groups) having a percent hydrolysis of 75% has an n/m ratio of 3.

A particularly preferred family of amphiphilic hydroxyl-functional vinyl copolymers are those where A is hydroxyl and B is acetate. Such copolymers are termed vinylacetate/vinylalcohol copolymers. Some commercial grades are also sometimes referred to simply as polyvinylalcohol. However, the true homopolymer, polyvinylalcohol is not amphiphilic and is almost entirely water insoluble. Preferred vinylacetate/vinylalcohol copolymers are those where H is between about 67% and 99.5%, or n/m has a value between about 2 and 200. The preferred average molecular weight is between about 2500 and 1,000,000 daltons and more preferably between about 3000 and about 100,000 daltons.

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Maiden, Mass.; amine-functionalized polyacrylates and polymethacrylates; proteins such as gelatin and albumin; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGITS, which are copolymers of methacrylates and acrylates.

A preferred class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymers hydroxyl groups. Generally, the degree of substitution of each substituent group can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulosic polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable cellulosic polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, ethyl carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimelli-tate, hydroxypropyl methyl cellulose acetate trimelli-tate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary cellulosic polymers that meet the definition of amphiphilic, having hydrophilic and hydrophobic regions include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A particularly desirable subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, and hydroxyethyl cellulose acetate succinate. Of these cellulosic polymers that are at least partially ionized at physiologically relevant pHs, the inventors have found the following to be most preferred: hydroxypropyl methyl cellulose acetate succinate, hydroxypropyl methyl cellulose phthalate, cellulose acetate phthalate and cellulose acetate trimellitate. The most preferred is hydroxypropyl methyl cellulose acetate succinate.

Another preferred class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form. By "neutralized acidic cellulosic polymers" is meant any cellulosic "acidic polymer" for which a significant fraction of the "acidic moieties" or "acidic substituents" have been "neutralized." By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer, that has a $pK_a$ of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail in commonly assigned provisional patent application U.S. Ser. No. 60/300, 256 entitled "Pharmaceutical Compositions of Drugs and Neutralized Acidic Polymers" filed Jun. 22, 2001, the relevant disclosure of which is incorporated by reference.

While specific polymers have been discussed as being suitable for use in the mixtures of the present invention, blends of such polymers may also be suitable. Thus, the term "concentration-enhancing polymer" is intended to include blends of polymers in addition to a single species of polymer.

Preparation of Compositions

The compositions of the present invention may be prepared by any method that results in a mixture of the drug/matrix dispersion and the concentration-enhancing polymer. Mixing processes include physical processing as well as wet-granulation and coating processes. Any conventional mixing method that does not substantially convert the drug/matrix dispersion and concentration-enhancing polymer into another molecular dispersion may be used. The resulting mixture may be a solid composition comprising the concentration-enhancing polymer suspended in the drug/matrix dispersion, a mixture of separate drug/matrix dispersion particles and concentration-enhancing particles interspersed with one another, a series of respective layers of drug/matrix dispersion and concentration-enhancing polymer, or any other mixture of drug/matrix dispersion and concentration-enhancing polymer.

For example, mixing methods include convective mixing, shear mixing, or diffusive mixing. Convective mixing involves moving a relatively large mass of material from one part of a powder bed to another, by means of blades or paddles, revolving screw, or an inversion of the powder bed. Shear mixing occurs when slip planes are formed in the material to be mixed. Diffusive mixing involves an exchange of position by single particles. These mixing processes can be performed using equipment in batch or continuous mode. Tumbling mixers (e.g., twin-shell) are commonly used equipment for batch processing. Continuous mixing can be used to improve composition uniformity. Continuous mixers include "in-line" mixers and extruders. Extruders may be single screw or twin-screw. Twin-screw extruders may turn in the same or opposite direction.

Milling may also be employed to prepare the compositions of the present invention. Milling is the mechanical process of reducing the particle size of solids (comminution). Because in some cases milling may alter crystalline structure and cause chemical changes for some materials, milling conditions are generally chosen which do not alter the physical form of the drug/matrix dispersion in the sense that the drug/matrix dispersion and concentration-enhancing polymer are not, to a large extent, mixed at the molecular level to form another dispersion of concentration-enhancing polymer, and drug and matrix. Thus, the composition after milling continues to contain regions rich in the drug/matrix dispersion and regions rich in concentration-enhancing polymer. The most common types of milling equipment are the rotary cutter, the hammer, the roller and fluid energy mills. Equipment choice depends on the characteristics of the ingredients in the drug form (e.g., soft, abrasive, or friable). Wet- or dry-milling techniques can be chosen for several of these processes, also depending on the characteristics of the ingredients (e.g. drug stability in solvent). The milling process may serve simultaneously as a mixing process if the feed materials are heterogeneous. Conventional mixing and milling processes suitable for use in the present invention are discussed more fully in Lachman, et al., The Theory and Practice of Industrial Pharmacy (3d Ed. 1986).

The components of the compositions of this invention may also be combined by dry- or wet-granulating processes as long as granulating conditions are chosen that do not transform a substantial portion of the drug/matrix dispersion and concentration-enhancing polymer into a molecular dispersion of the drug, matrix and concentration-enhancing polymer.

Alternatively, the mixture may be formed by first combining the drug, matrix and concentration-enhancing polymer and then forming the dispersion in the presence of the concentration-enhancing polymer, resulting in a mixture of the drug/matrix dispersion and the concentration-enhancing polymer. For example, the drug and matrix may be chosen such that the drug is highly soluble in the matrix and is present in an amount below the solubility limit of the drug in the matrix. The concentration-enhancing polymer may be essentially insoluble in the matrix, or may have a high melting point. In either case, the drug, matrix and concentration-enhancing polymer may be blended together, heated and then cooled to form a drug/matrix dispersion using a melt/congeal process. This yields a solid mixture in which the concentration-enhancing polymer is suspended as a separate phase. As yet another example, the concentration-enhancing polymer may be insoluble in the matrix and partition from the drug and matrix during solvent processing into a separate domain. In that case, the drug, matrix and concentration-enhancing polymer may be spray-dried together, resulting in a mixture of drug/matrix dispersion and concentration-enhancing polymer. In another example, the concentration-enhancing polymer may be dissolved in a solvent in which the drug/matrix dispersion is substantially insoluble. The drug/matrix dispersion may then be suspended in the solution containing the dissolved polymer. The solvent may then be removed from this suspension, for example by spray drying or evaporation, resulting in a mixture of drug/matrix dispersion and concentration-enhancing polymer. In all of these methods, the concentration-enhancing polymer in the resulting mixture exists in a domain that is separate from the drug/matrix dispersion as a separate phase and retains its bulk characteristics.

In addition to the physical mixtures described above, the compositions of the present invention may constitute any device or collection of devices that accomplishes the objective of delivering to the use environment both the drug/matrix dispersion and the concentration-enhancing polymer. For example, the composition may be in the form of a single dosage form in which the dispersion and concentration-enhancing polymer occupy separate regions within the dosage form. Thus, in the case of oral administration to an animal, the dosage form may constitute a layered tablet wherein one or more layers comprise the drug/matrix dispersion and one or more other layers comprise the concentration-enhancing polymer. Alternatively, the dosage form may be a coated tablet wherein the tablet core comprises the drug/matrix dispersion and the coating comprises the concentration-enhancing polymer. Yet another alternative is for the dosage form to comprise a coated tablet wherein the tablet core comprises the concentration-enhancing polymer and the coating comprises the drug/matrix dispersion. The dosage form may also be a capsule where the wall of the capsule comprises the concentration-enhancing polymer and the drug/matrix dispersion is within the capsule. In addition, the drug/matrix dispersion and the concentration-enhancing polymer may even be present in different dosage forms such as tablets or beads and may be administered simultaneously or separately as long as both the drug/matrix dispersion and concentration-enhancing polymer are administered in such a way that the drug and concentration-enhancing polymer can come into contact in the use environment. When the drug/matrix dispersion and the concentration-enhancing polymer are administered separately it is generally preferable to deliver the concentration-enhancing polymer prior to the drug.

As described above, in one embodiment the invention finds utility where it is difficult to form a dispersion of the drug and concentration-enhancing polymer. Thus, at least a portion, if not all, of the concentration-enhancing polymer is present separate from the dispersion of drug and matrix. In general, a molecular dispersion of drug and polymer is one in which the physical properties of the mixture, such as melting point or glass-transition temperature, are transformed from those characteristic of the bulk (i.e., undispersed) polymer and drug. In the compositions of the present invention, as disclosed above, the dispersion and at least a portion of the concentration-enhancing polymer each retain their individual respective physical properties, such as melting point and/or glass-transition temperature.

The amount of concentration-enhancing polymer relative to the amount of drug present in the mixtures of the present invention depends on the drug and concentration-enhancing polymer and may vary widely from a drug-to-polymer weight ratio of 0.01 to 5. However, in most cases, except when the drug dose is quite low, e.g., 25 mg or less, it is preferred that the drug-to-polymer ratio is greater than 0.05 and less than 2.5 and often the enhancement in drug concentration or relative bioavailability is observed at drug-to-polymer ratios of 1 or less or for some drugs even 0.2 or less. In cases where the drug dose is about 25 mg or less, the drug-to-polymer weight ratio may be significantly less than 0.05. In general, regardless of the dose, enhancements in drug concentration or relative bioavailability increase with decreasing drug-to-polymer weight ratio. However, due to the practical limits of keeping the total mass of a tablet, capsule or suspension low, it is often desirable to use a relatively high drug-to-polymer ratio as long as satisfactory results are obtained. The maximum drug:polymer ratio that yields satisfactory results varies from drug to drug and is best determined in the in vitro and/or in vivo dissolution tests discussed below.

In general, to maximize the drug concentration or relative bioavailability of the drug, lower drug-to-polymer ratios are preferred. At low drug-to-polymer ratios, there is sufficient concentration-enhancing polymer available in solution to ensure the inhibition of the precipitation or crystallization of drug from solution and, thus, the average concentration of drug is much higher. For high drug/polymer ratios, not enough concentration-enhancing polymer may be present in solution and drug precipitation or crystallization may occur more readily. However, the amount of concentration-enhancing polymer that can be used in a dosage form is often limited by the maximum total mass of the dosage form that is acceptable. For example, when oral dosing to a human is desired, at low drug/polymer ratios the total mass of drug and polymer may be unacceptably large for delivery of the desired dose in a single tablet or capsule. Thus, it is often necessary to use drug/polymer ratios that are less than those which yield maximum drug concentration relative bioavailability in specific dosage forms to provide a sufficient drug dose in a dosage from that is small enough to be easily delivered to a use environment.

Concentration Enhancement

The concentration-enhancing polymer is present in a sufficient amount so as to improve the concentration of the drug in a use environment relative to a control composition. At a minimum, the compositions of the present invention provide concentration-enhancement relative to a control comprising crystalline drug alone. Thus, the concentration-enhancing polymer is present in a sufficient amount so that when the composition is administered to a use environment, the composition provides improved drug concentration (as described more fully below) relative to a control consisting of an equivalent amount of crystalline drug but with no concentration-enhancing polymer present.

Preferably, the compositions of the present invention provide concentration-enhancement relative to other compositions containing an equivalent amount of amorphous drug. Thus, the compositions of the present invention preferably provide concentration enhancement relative to an equivalent amount of drug but in undispersed amorphous form alone (if the amorphous form is stable). In more preferred embodiments, the compositions of the present invention provide concentration-enhancement relative to an equivalent amount of drug/matrix dispersion but without any concentration-enhancing polymer present.

As used herein, a "use environment" can be either the in vivo environment of the GI tract, subdermal, intranasal, buccal, intrathecal, ocular, intraaurial, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS) or a Model Fasted Duodenal (MFD) solution. Concentration enhancement may be determined through either in vitro dissolution tests or through in vivo tests. It has been determined that enhanced drug concentration in in vitro dissolution tests in Model Fasted Duodenal (MFD) solution or Phosphate Buffered Saline (PBS) is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine. In particular, a composition containing a concentration-enhancing polymer may be dissolution-tested by adding it to MFD or PBS solution and agitating to promote dissolution.

In one aspect, a composition containing a concentration-enhancing polymer of the present invention provides a Maximum Drug Concentration (MDC) that is at least 1.25-fold the MDC of at least one of the control compositions. In other words, if the MDC provided by the control composition is 100 □g/mL, then a composition of the present invention provides an MDC of at least 125 □g/mL. More preferably, the MDC of drug achieved with the compositions of the present invention are at least 2-fold, and even more preferably at least 3-fold, that of at least one of the control compositions.

Alternatively, the compositions containing concentration-enhancing polymers of the present invention provide in an aqueous use environment a concentration versus time Area Under The Curve (AUC), for any period of at least 90 minutes between the time of introduction into the use environment and about 270 minutes following introduction to the use environment that is at least 1.25-fold that of at least one of the control compositions. More preferably, the AUC achieved with the compositions of the present invention are at least 2-fold and more preferably at least 3-fold that of at least one of the control compositions.

Alternatively, the compositions of the present invention containing concentration-enhancing polymers, when dosed orally to a human or other animal, provide an AUC in drug concentration in the blood plasma or serum that is at least 1.25-fold that observed when one of the control compositions is dosed. More preferably, the AUC in the blood plasma or serum is at least 2-fold and more preferably at least 3-fold that observed when one of the control compositions is dosed. Thus, the compositions of the present invention can be evaluated in either an in vitro or in-vivo test, or both.

A typical test to evaluate enhanced drug concentration can be conducted by (1) adding a sufficient quantity of test composition (e.g., the dispersion and concentration-enhancing polymer) to a test medium (such as PBS or MFD solution), such that if all of the drug dissolved, the theoretical concentration of drug would exceed the equilibrium concentration of the drug in the test medium by a factor of at least 2; (2) adding an appropriate amount of control composition to an equivalent amount of test medium, and (3) determining whether the measured MDC and/or AUC of the test composition in the test medium is at least 1.25-fold that of the MDC and/or AUC provided by the control composition. In conducting such a dissolution test, the amount of test composition used is an amount such that if all of the drug dissolved, the drug concentration would be at least 2-fold to 100-fold that of the equilibrium concentration of the drug. The concentration of dissolved drug is typically measured as a function of time by sampling the test medium and plotting drug concentration in the test medium vs. time so that the MDC and/or AUC can be ascertained.

To avoid drug particulates which would give an erroneous determination, the test solution is either filtered or centrifuged. "Dissolved drug" is typically taken as that material that either passes a 0.45 □m syringe filter or, alternatively, the material that remains in the supernatant following centrifugation. Filtration can be conducted using a 13 mm, 0.45 □m polyvinylidine difluoride syringe filter sold by Scientific Resources under the trademark TITAN7. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred compositions. It is recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

Alternatively, the compositions of the present invention provide improved relative bioavailability. Relative bioavailability of the drug in the compositions of the present invention can be tested in vivo in animals or humans using conventional methods for making such a determination. An in vivo test, such as a crossover study, may be used to determine whether a test composition provides an enhanced relative bioavailability compared with a control composition. In an in vivo crossover study a "test composition" of dispersion and concentration-enhancing polymer is dosed to half a group of test subjects and, after an appropriate washout period (e.g., one week) the same subjects are dosed with a "control composition." The "control composition" may be any of the control compositions described earlier. The other half of the group is dosed with the control composition first, followed by the test composition. The relative bioavailability is measured as the concentration in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis). Generally, the values for AUC represent a number of values taken from all of the subjects in a patient test population averaged over the entire test population.

A preferred embodiment of the invention is one in which the relative bioavailability of the test composition is at least 1.25 relative to at least one of the control compositions. (That is, the AUC in the blood provided by the test composition is at least 1.25-fold the AUC provided by the control composition.) An even more preferred embodiment of the invention is one in which the relative bioavailability of the test composition is at least 2.0 relative to at least one of the control compositions. The determination of AUCs is a well-known procedure and is described, for example, in Welling, "Pharmacokinetics Processes and Mathematics," ACS Monograph 185 (1986).

Often the enhancement in drug concentration or relative bioavailability that is observed increases as the drug: concentration-enhancing polymer ratio decreases from a value of about 1 to a value of about 0.1. The drug:polymer ratio that yields optimum results varies from drug to drug and is best determined in in vitro dissolution tests and/or in vivo bioavailability tests. However, the amount of concentration-enhancing polymer that can be used in a dosage form is often limited by the total mass requirements of the dosage form as described above.

While not wishing to be bound by a particular theory, it is believed that while the concentration-enhancing polymer(s) of the present invention may to some extent solubilize insoluble drugs (that is, to increase the equilibrium concentration of free drug), the concentration-enhancing polymers also act to slow the rate of precipitation or crystallization of the drug after the drug is initially dissolved. The presence of the concentration-enhancing polymer(s) thus allows the initially increased or enhanced concentration provided by the drug/matrix dispersion to be at least partially maintained for at least a few minutes and, in some cases, for many hours. In addition, in cases where dissolution of the drug is slow and precipitation of the crystalline drug, in the absence of the concentration-enhancing polymer, is fast, the presence of the concentration-enhancing polymer may result in the maximum concentration of drug observed being substantially higher than that observed in the absence of the concentration-enhancing polymer.

One possible mechanism for improving the drug concentration involves the association of the concentration-enhancing polymer and dissolved drug to form "polymer/drug assemblies." Such assemblies may constitute various forms, including polymeric micelles, high-energy polymer-drug aggregates ranging in size from a few nanometers to 1000 nanometers, polymer-stabilized drug colloids or polymer/drug complexes. An alternative view is that as dissolved drug begins to precipitate or crystallize from solution (e.g., as nucleation begins) the polymer adsorbs to these drug aggregates or nuclei, preventing, or at least retarding, the nucleation or crystal-growth process. In any case, the presence of the polymer serves to enhance the amount of drug that is dissolved or at least available for absorption. Drug present in the various drug/polymer assemblies listed above is apparently quite labile and may contribute to the drug absorption process.

Excipients and Dosage Forms

Although the key ingredients present in the compositions of the present invention are simply the drug/matrix dispersion combined with the concentration-enhancing polymer(s), the inclusion of other excipients in the composition may be useful. These excipients may be utilized with the dispersion/polymer mixture in order to formulate the mixture into tablets, capsules, suspensions, powders for suspension, creams, transdermal patches, depots, and the like. In addition, as described above, the drug/matrix dispersion and the concentration-enhancing polymer may be mixed with excipients separately to form different beads, or layers, or coatings, or cores or even separate dosage forms.

One very useful class of excipients is surfactants. Suitable surfactants include fatty acid and alkyl sulfonates; commercial surfactants such as benzethanium chloride (HYAMINE7 1622, available from Lonza, Inc., Fairlawn, N.J.); DOCUSATE SODIUM (available from Mallinckrodt Spec. Chem., St. Louis, Mo.); polyoxyethylene sorbitan fatty acid esters (TWEEN7, available from ICI Americas Inc., Wilmington, Del.); LIPOSORB7 P-20 (available from Lipochem Inc., Patterson N.J.); CAPMUL7 POE-0 (available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug. These surfactants may comprise up to 5 wt % of the composition.

The addition of pH modifiers such as acids, bases, or buffers may also be beneficial, retarding the dissolution of the composition (e.g., acids such as citric acid or succinic acid when the polymer is anionic) or, alternatively, enhancing the rate of dissolution of the composition (e.g., bases such as sodium acetate or amines when the polymer is anionic).

Other conventional formulation excipients may be employed in the compositions of this invention, including those excipients well-known in the art (e.g., as described in Remington's Pharmaceutical Sciences ($16^{th}$ ed. 1980). Generally, excipients such as fillers, disintegrating agents, pigments, binders, lubricants, glidants, flavorants, and so forth may be used for customary purposes and in typical amounts without adversely affecting the properties of the compositions. These excipients may be utilized after the drug/polymer composition has been formed, in order to formulate the composition into tablets, capsules, suspensions, powders for suspension, creams, transdermal patches, and the like.

Examples of other matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose.

Examples of surface active agents include sodium lauryl sulfate and polysorbate 80.

Examples of drug complexing agents or solubilizers include the polyethylene glycols, caffeine, xanthene, gentisic acid and cylodextrins.

Examples of disintegrants include sodium starch glycolate, sodium carboxymethyl cellulose, calcium carboxymethyl cellulose, croscarmellose sodium, crospovidone (crosslinked polyvinyl pyrrolidone), methyl cellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenatetd vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of glidants include silicon dioxide, talc and cornstarch.

Compositions of this invention may be used in a wide variety of dosage forms for administration of drugs. Exemplary dosage forms are powders or granules that may be taken orally either dry or reconstituted by addition of water to form a paste, slurry, suspension or solution; tablets; capsules; multiparticulates; and pills. Various additives may be mixed, ground, or granulated with the compositions of this invention to form a material suitable for the above dosage forms.

In some cases, the overall dosage form or particles, granules or beads that make up the dosage form may have superior performance if coated with an enteric polymer to prevent or retard dissolution until the dosage form leaves the stomach. Exemplary enteric coating materials include HPMCAS, HPMCP, CAP, CAT, carboxymethylethyl cellulose, carboxylic acid-functionalized polymethacrylates, and carboxylic acid-functionalized polyacrylates.

Compositions of this invention may be administered in a controlled release dosage form. In one such dosage form, the composition of the drug/matrix dispersion and concentration-enhancing polymer is incorporated into an erodible polymeric controlled-release matrix device. By an erodible controlled-release matrix is meant aqueous-erodible or water-swellable or aqueous-soluble in the sense of being either erodible or swellable or dissolvable in pure water or requiring the presence of an acid or base to ionize the polymeric controlled-release matrix sufficiently to cause erosion or dissolution. When contacted with the aqueous environment of use, the erodible polymeric controlled-release matrix imbibes water and forms an aqueous-swollen gel or "matrix" that entraps the mixture of drug/matrix dispersion and concentration-enhancing polymer. The aqueous-swollen controlled-release matrix gradually erodes, swells, disintegrates or dissolves in the environment of use, thereby controlling the release of the drug mixture to the environment of use.

Alternatively, the compositions of the present invention may be administered by or incorporated into a non-erodible controlled-release matrix device.

Alternatively, the drug mixture of the invention may be delivered using a coated osmotic controlled release dosage form. This dosage form has two components: (a) the core which contains an osmotic agent and the drug/matrix dispersion; and (b) a coating surrounding the core, the coating controlling the influx of water to the core from an aqueous environment of use so as to cause drug release by extrusion of some or all of the core to the environment of use. The osmotic agent contained in the core of this device may be an aqueous-swellable hydrophilic polymer, hydrogel, osmogen, or osmagent. The coating is preferably polymeric, aqueous-permeable, and has at least one delivery port. The concentration-enhancing polymer may be either mixed with the drug/matrix dispersion or be in a separate region of the core or it may be applied as a second coating over the coating that controls the influx of water.

Alternatively, the drug mixture of the invention may be delivered via a coated hydrogel controlled release dosage form having three components: (a) a drug-containing composition containing the drug/matrix dispersion, (b) a water-swellable composition wherein the water-swellable composition is in a separate region within a core formed by the drug-containing composition and the water-swellable composition, and (c) a coating around the core that is water-permeable, and has at least one delivery port therethrough. In use, the core imbibes water through the coating, swelling the water-swellable composition and increasing the pressure within the core, and fluidizing the drug-containing composition. Because the coating remains intact, the drug-containing composition is extruded out of the delivery port into an environment of use. The concentration-enhancing polymer may be delivered in a separate dosage form, may be included in the drug-containing composition, may be included in the water-swellable composition, may be included in a separate layer within the core, or may constitute all or part of a coating applied to the dosage form.

Alternatively, the compositions of the present invention may be co-administered, meaning that the dispersion can be administered separately from, but within the same general time frame as, the concentration-enhancing polymer. Thus, a dispersion can, for example, be administered in its own dosage form which is taken at approximately the same time as the concentration-enhancing polymer which is in a separate dosage form. If administered separately, it is generally preferred to administer both the dispersion and the concentration-enhancing polymer within 60 minutes of each other, so that the two are present together in the environment of use. When not administered simultaneously, the concentration-enhancing polymer is preferably administered prior to the dispersion.

In addition to the above additives or excipients, use of any conventional materials and procedures for preparation of suitable dosage forms using the compositions of this invention known by those skilled in the art are potentially useful.

Other features and embodiments of the invention will become apparent from the following examples which are given for illustration of the invention rather than for limiting its intended scope.

EXAMPLES

Example 1

A solid drug/matrix dispersion was prepared by forming an amorphous solid dispersion of 25 wt % of the low-solubility, acid-sensitive drug quinoxaline-2-carboxylic acid [4(R)carbamoyl-I(S)-3-fluorobenzyl)-2(S),7-dihydroxy-7-methyl-octyl]amide ("Drug 1") and 75 wt % polydextrose. The dispersion was made by first mixing Drug 1 in a 3/1 methanol/water solvent together with polydextrose (Litesse Ultra7, manufactured by Cultor Food Science, Inc., Ardsley, N.Y.) to form a solution. The solution comprised 1.3 wt % Drug 1, 3.8 wt % polydextrose, and 94.9 wt % 3/1 (wt/wt) methanol/water. This solution was pumped into a "mini" spray-dryer apparatus via a syringe pump at a rate of 30 mL/hr. The spray solution was metered using a Cole Parmer 74900 series rate-controlling syringe pump. The solution was atomized through a Spraying Systems Company two-fluid nozzle, model number SU1A, with nitrogen as the atomizing gas. The nitrogen was pressurized and heated to a temperature of 115° C. The solution was sprayed from the top of an 11-cm diameter stainless steel chamber. The resulting solid amorphous dispersion was collected on a Whatman7 1 filter paper at a yield of about 54%, dried under vacuum, and stored in a dessicator.

Example 1 was prepared by combining the solid dispersion with the concentration-enhancing polymer HPMCAS. 14.4 mg of the dispersion was added to two respective microcentrifuge tubes. The tubes were each placed in a 37° C. sonicating bath, and 1.8 mL phosphate buffered saline (PBS) with 14.4 mg HPMCAS-HF at pH 6.5 and 290 mOsm/kg was added to each tube. The samples were quickly mixed using a vortex mixer for about 60 seconds. The samples were centrifuged at 12,000 G at 37° C. for 1 minute. The resulting supernatant solution was then sampled and diluted 1:6 (by volume) with methanol and then analyzed by high-performance liquid chromatography (HPLC). The contents of the tubes were mixed on the vortex mixer and allowed to stand undisturbed at 37° C. until the next sample was taken. Samples were collected at 4, 10, 20, 40, 90, 180 and 1200 minutes. The average concentrations of drug obtained in these samples are shown in Table 1 below.

Similarly, a control composition C1 was prepared comprising the same dispersion as Example 1 but without the concentration-enhancing polymer HPMCAS. An in vitro dissolution test was performed using the procedures described for Example 1 except that 14.4 mg of the dispersion was tested without the concentration-enhancing polymer (HPMCAS) in the test solution.

A control composition C2 comprising amorphous Drug 1 alone (that is, undispersed amorphous Drug 1) was also prepared. A dissolution test was performed using the procedures described for Example 1 except that 3.6 mg of the amorphous drug was tested without the concentration-enhancing polymer in the test solution. The concentrations of drug obtained in in vitro dissolution tests are shown below in Table 1.

TABLE 1

| Example | Time (min) | Drug 1 Conc. (μg/mL) | AUC (min * μg/mL) |
|---|---|---|---|
| 1 | 0 | 0 | 0 |
|  | 4 | 903 | 1,800 |
|  | 10 | 1299 | 8,400 |
|  | 20 | 1436 | 22,100 |
|  | 40 | 1542 | 51,900 |
|  | 90 | 1548 | 129,100 |
|  | 180 | 1591 | 270,400 |
|  | 1200 | 1646 | 1,921,200 |
| C1 | 0 | 0 | 0 |
|  | 4 | 723 | 1,400 |
|  | 10 | 947 | 6,500 |
|  | 20 | 1097 | 16,700 |
|  | 40 | 1249 | 40,100 |
|  | 90 | 1114 | 99,200 |
|  | 180 | 750 | 183,100 |
|  | 1200 | 426 | 782,900 |
| C2 | 0 | 0 | 0 |
|  | 4 | 619 | 1,200 |
|  | 10 | 841 | 5,600 |
|  | 20 | 947 | 14,600 |
|  | 40 | 1028 | 34,300 |
|  | 90 | 1104 | 87,600 |
|  | 1200 | 706 | 1,092,200 |

The results of this test are summarized in Table 2, which shows the maximum concentration of Drug 1 in solution in Example 1 during the first 90 minutes of the test ($C_{max,90}$), the area under the aqueous concentration versus time curve after 90 minutes ($AUC_{90}$), and the concentration at 1200 minutes ($C_{1200}$).

TABLE 2

| Ex. | Matrix Material | Drug 1 Conc. in the Dispersion (wt %) | Conc.-Enhancing Polymer | $C_{max,90}$ (μg/mL) | $AUC_{90}$ (min * μg/mL) | $C_{1200}$ (μg/mL) |
|---|---|---|---|---|---|---|
| 1 | Polydextrose | 25 | HPMCAS | 1548 | 129,100 | 1646 |
| C1 | Polydextrose | 25 | none | 1249 | 99,200 | 426 |
| C2 | none | C | none | 1104 | 87,600 | 706 |

*Polymer designations: HPMCAS = hydroxypropyl methyl cellulose acetate succinate The results, summarized in Table 2, show that the performance of the composition of Example 1 containing concentration-enhancing polymer was much better than that of the dispersion alone. The $C_{max,90}$ of Example 1 was 1.24-fold that of control C1, and $AUC_{90}$ was 1.30-fold that of C1. In addition, the dissolved drug concentration at 1200 minutes (20 hours) for the test composition was 3.9-fold that of the Control C1, showing that the composition sustained higher concentration of drug for a longer period of time. The $C_{max,90}$ of Example 1 was 1.40-fold that of control C2, and $AUC_{90}$ was 1.47-fold that of C2. In addition, the dissolved drug concentration at 1200 minutes (20 hours) for the test composition was 2.33-fold that of the Control C2.

Example 2

This example discloses a composition comprising a drug/matrix dispersion of an acid-sensitive drug, Drug 1, and an acidic concentration-enhancing polymer which has improved chemical stability. Example 2 was prepared by mixing 25 wt % of the drug/matrix dispersion containing Drug 1 (an acid-sensitive drug) formed in Example 1 with 75 wt % of the acidic concentration-enhancing polymer HPMCAS. The composition of Example 2 was then placed in a controlled-atmosphere chamber maintained at 40° C. and 75% RH for 10 days. Drug 1 potencies of the composition before and after storage were determined using HPLC. Drug 1 potency was the percent of the total HPLC peak area corresponding to the amount of drug originally present in the dispersion prior to storage. The results are shown in Table 3 below.

A control composition, C3, comprising a dispersion of Drug 1 with HPMCAS-LF was made by preparing a solution containing 0.33 wt % Drug 1 and 1.0 wt % HPMCAS-LF in acetone, and spray-drying the solution using the "mini" spray-dryer apparatus described in Example 1, except that the nitrogen was heated to 100° C. Control C3 was placed in a controlled-atmosphere chamber maintained at 40° C. and 75% RH for 14 days and Drug 1 potencies of the composition before and after storage were determined using HPLC as described above. The results are shown in Table 3.

TABLE 3

| Example No. | Matrix Material | Conc.-Enhancing Polymer | Potency Before Storage (wt %) | Potency Day 10 at 40° C./ 75% RH (wt %) | Degree of Degradation Day 10 40° C./ 75% RH (wt %) |
|---|---|---|---|---|---|
| 2 | Polydextrose | HPMCAS-LG | 100 | 88 | 12 |
| C3 | HPMCAS-LF | None | 94 | <1* | >93* |

*Data for Control C3 was obtained after 14 days

As can be seen from the data in Table 3, the composition of Example 2 provided improved chemical stability for Drug 1 compared with the Control C3, which was a dispersion of Drug 1 in the acidic concentration-enhancing polymer.

Examples 3 and 4

These examples demonstrate drug/matrix dispersions formed using Drug 1 but with different matrix materials. Solid drug/matrix dispersions were prepared using the procedure described in Example 1 with the following exceptions. The matrix for Example 3 was polyvinylalcohol (PVA) and for Example 4 was dextran. The solvent used to form the spray solution for Drug 1 and PVA was 4/1 methanol/water, and the solvent used to form the spray solution of Drug 1 and dextran was 3/2 water/methanol. The nitrogen was heated to 100° C. for Example 3 and 130° C. for Example 4. The yields were 61% for the PVA dispersion and 52% for the dextran dispersion.

Example 3 was prepared by mixing 14.4 mg of the PVA dispersion with 14.4 mg HPMCAS-HF, while Example 4 was prepared by mixing 14.4 mg of the dextran dispersion with 14.4 mg of HPMCAS-HF. In vitro dissolution tests of Examples 3 and 4 were performed using the procedure described in Example 1.

Control C2 was simply amorphous drug alone used in the dissolution test described in Example 1. Controls C4 and C5 were prepared using 14.4 mg of the same dispersions as Examples 3 and 4, respectfully, but without the concentration-enhancing polymer. In vitro dissolution tests were performed using the procedures described in Example 1. The concentrations of drug obtained in in vitro dissolution tests are shown below.

The results are presented in Table 4 and summarized in Table 5.

TABLE 4

| Example | Time (min) | Drug 1 Concentration (μg/mL) | AUC (min * μg/mL) |
|---|---|---|---|
| 3 | 0 | 0 | 0 |
|  | 4 | 1365 | 2,700 |
|  | 10 | 1441 | 11,100 |
|  | 20 | 1399 | 25,400 |
|  | 40 | 1577 | 55,100 |
|  | 90 | 1541 | 133,000 |
|  | 180 | 1648 | 276,500 |
|  | 1200 | 1863 | 2,067,200 |
| 4 | 0 | 0 | 0 |
|  | 4 | 1179 | 2,400 |
|  | 10 | 1093 | 9,200 |
|  | 20 | 1164 | 20,500 |
|  | 40 | 1161 | 43,700 |
|  | 90 | 1441 | 108,800 |
|  | 180 | 1619 | 246,500 |
|  | 1200 | 2196 | 2,192,100 |
| C4 | 0 | 0 | 0 |
|  | 4 | 1554 | 3,100 |
|  | 10 | 1860 | 13,300 |
|  | 20 | 1474 | 30,000 |
|  | 40 | 744 | 52,200 |
|  | 90 | 685 | 87,900 |
|  | 180 | 632 | 147,200 |
|  | 1200 | 580 | 765,300 |
| C5 | 0 | 0 | 0 |
|  | 4 | 949 | 1,900 |
|  | 10 | 1021 | 7,800 |
|  | 20 | 1169 | 18,800 |
|  | 40 | 1237 | 42,800 |
|  | 90 | 964 | 97,800 |
|  | 180 | 511 | 164,200 |
|  | 1200 | 454 | 656,400 |

The results of this test are summarized in Table 5, which shows the maximum concentration of Drug 1 in solution during the first 90 minutes of the test ($C_{max90}$), the area under the aqueous concentration versus time curve after 90 minutes ($AUC_{90}$), and the concentration at 1200 minutes ($C_{1200}$). Dissolution test results for Drug 1 dispersions described in Examples 3 and 4 and Controls C2, C3 and C4, are all shown in Table 5 for comparison.

TABLE 5

| Ex. | Matrix Material | Drug 1 Conc. in the Dispersion (wt %) | Conc.-Enhanc. Polymer | $C_{max.90}$ (μg/mL) | $AUC_{90}$ (min * μg/mL) | $C_{1200}$ (μg/mL) |
|---|---|---|---|---|---|---|
| 3 | PVA | 25 | HPMCAS | 1541 | 133,000 | 1863 |
| 4 | Dextran | 25 | HPMCAS | 1441 | 108,800 | 2196 |
| C2 | none | C | none | 1104 | 87,600 | 706 |
| C4 | PVA | 25 | none | 1860 | 87,900 | 580 |
| C5 | Dextran | 25 | none | 1237 | 97,800 | 454 |

* Polymer designations: HPMCAS = hydroxypropyl methyl cellulose acetate succinate, PVA = polyvinylalcohol The results, summarized in Table 5, show that the performance of the compositions of Examples 3 and 4 containing concentration-enhancing polymer were better than that of the controls. For Example 3, the $C_{max90}$ was 1.4-fold that of Control C2 (undispersed amorphous drug), and the $AUC_{90}$ was 1.5-fold that of Control C2. In addition, Example 3 provided an $AUC_{90}$ that was 1.5-fold that of Control C4, the drug/matrix dispersion without concentration-enhancing polymer. For Example 4, the $C_{max90}$ was 1.3-fold that of Control C2, and the $AUC_{90}$ was 1.24-fold that of Control C2. In addition, Example 4 provided a $C_{max90}$ that was 1.16-fold that of Control C5 (the drug/matrix dispersion without concentration-enhancing polymer), and an $AUC_{90}$ that was 1.11-fold that of Control C5.

Example 5

This example demonstrates a drug/matrix dispersion with another drug. A solid drug/matrix dispersion comprised of 10 wt % 3,5-dimethyl-4-(3'-pentoxy)-2-(2',4',6'-trimethylphenoxy)pyridine ("Drug 2") and 90 wt % polyethylene glycol was prepared by a melt-congeal process. 4.5 gm polyethylene glycol 3350 (PEG 3350 Union Carbide Corp.) was heated in a 70° C. oven to obtain a clear liquid, and 0.5 g of Drug 2 was added. Following addition of Drug 2, the melt was stirred and returned to the 70° C. oven for 2.5 hours. Next, the melt was cooled to room temperature and ground in a mortar and pestle using liquid nitrogen. The resulting solid amorphous dispersion contained 10 wt % Drug 2.

Example 5 was prepared by combining the drug/matrix dispersion of Drug 2 and polyethylene glycol with the concentration-enhancing polymer HPMCAS. Example 5 was evaluated in an in vitro dissolution test using a microcentrifuge method. In this test, 18 mg of the dispersion was added to each of two microcentrifuge tubes. The tubes were placed in a 37° C. temperature-controlled chamber, and 1.8 mL PBS containing 7.3 mM sodium taurocholic acid and 1.4 mM 1-palmitoyl-2-oleyl-sn-glycero-3-phosphocholine, with 7.2 mg HPMCAS-MF, was added. The tests were sampled as described in Example 1, and analyzed using HPLC. Samples were collected at 4, 10, 20, 40, 90, and 1200 minutes. The results are presented in Table 6 and 7.

For Control C6, in vitro tests were performed using the procedures described in Example 1 except that 18 mg of the dispersion of Example 5 was tested without concentration-enhancing polymer (HPMCAS) in the test solution. The concentrations of drug obtained in the in vitro dissolution test are shown in Table 6. For Control C7, the amorphous form of Drug 2 could not be isolated because it rapidly converted to the crystalline form. Thus, for Control C7, 1.8 mg of crystalline Drug 2 was tested (without concentration-enhancing polymer in the test solution).

TABLE 6

| Example | Time (min) | Drug 2 Concentration (μg/mL) | AUG (min * μg/mL) |
|---|---|---|---|
| 5 | 0 | 0 | 0 |
|  | 4 | 74 | 100 |
|  | 10 | 93 | 600 |
|  | 20 | 90 | 1,600 |
|  | 40 | 68 | 3,100 |
|  | 90 | 59 | 6,300 |
|  | 1200 | 58 | 71,300 |
| C6 | 0 | 0 | 0 |
|  | 4 | 83 | 200 |
|  | 10 | 80 | 700 |
|  | 20 | 72 | 1400 |
|  | 40 | 56 | 2,700 |
|  | 90 | 50 | 5,300 |
|  | 1200 | 51 | 61,400 |
| C7 | 0 | 0 | 0 |
|  | 4 | 16 | 0 |
|  | 10 | 33 | 200 |
|  | 20 | 32 | 500 |
|  | 40 | 30 | 1,100 |
|  | 90 | 39 | 2,800 |
|  | 1200 | 37 | 45,000 |

The results of this test are summarized in Table 7, which shows the maximum concentration of Drug 2 in solution during the first 90 minutes of the test ($C_{max90}$), the area under the aqueous concentration versus time curve after 90 minutes ($AUC_{90}$), and the concentration at 1200 minutes ($C_{1200}$). Dissolution test results for Drug 2 dispersions described in Example 5 and Controls C6 and C7, are all shown in Table 7 for comparison.

TABLE 7

| Example | Matrix Material* | Drug 2 Conc. in the Dispersion (wt %) | Concentration Enhanc. Polymer* | $C_{max,90}$ (μg/mL) | $AUC_{90}$ (min * μg/mL) | $C_{1200}$ (μg/mL) |
|---|---|---|---|---|---|---|
| 5 | PEG 3350 | 10 | HPMCAS | 93 | 6300 | 58 |
| C6 | PEG 3350 | 10 | None | 83 | 5300 | 51 |
| C7 | none | C | None | 39 | 2800 | 37 |

*Polymer designations: HPMCAS = hydroxypropyl methyl cellulose acetate succinate, PEG 3350 = polyethylene glycol 3350.

These results show that the addition of concentration-enhancing polymer increased the $C_{max90}$, $AUC_{90}$, and $C_{1200}$ for Drug 2 over that of the dispersion and crystalline drug alone. Example 5 provided a $C_{max,90}$ that was 1.12-fold, and an $AUC_{90}$ that was 1.19-fold that provided by Control C6, and a $C_{max,90}$ that was 2.38-fold, and an $AUC_{90}$ that was 2.25-fold that provided by Control C7.

Example 6

This example discloses yet another low-solubility drug. A drug/matrix dispersion of amorphous drug and matrix was prepared by forming an amorphous dispersion of 25 wt % [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester ("Drug 3") and 75 wt % PVP. The dispersion was formed by spray-drying a solution containing 0.96 wt % Drug 3 and 2.89 wt % PVP in acetone, using a "mini" spray-drier as described in Example 1, except that the nitrogen was heated to 100° C. The resulting dispersion contained 25 wt % Drug 3.

Example 6 was prepared by combining the dispersion with the concentration-enhancing polymer HPMCAS. 7.2 mg of the dispersion of Example 6 was added to microcentrifuge tubes. Tests were performed in duplicate. The tubes were placed in a 37° C. temperature-controlled chamber, and 1.8 mL PBS with 5.4 mg HPMCAS-MF was added. The tests were sampled as described in Example 1, and analyzed using HPLC.

For Control C8, in vitro dissolution tests were performed using the procedures described above except that 7.2 mg of the amorphous dispersion of Example 6 was tested without concentration-enhancing polymer (HPMCAS) in the test solution. The concentrations of drug obtained in the in vitro dissolution test are shown in Table 7.

For Control C9, 1.8 mg of undispersed amorphous Drug 3 was tested (without concentration-enhancing polymer in the test solution) using the procedures described above.

TABLE 8

| Example | Time (min) | Drug 3 Concentration (μg/mL) | AUC (min * μg/mL) |
|---|---|---|---|
| 6 | 0 | 0 | 0 |
|  | 4 | 51 | 100 |
|  | 10 | 40 | 400 |
|  | 20 | 37 | 800 |
|  | 40 | 39 | 1,500 |
|  | 90 | 31 | 3,300 |
|  | 1200 | 13 | 27,700 |
| C8 | 0 | 0 | 0 |
|  | 4 | 29 | 100 |
|  | 10 | 16 | 200 |
|  | 20 | 11 | 300 |
|  | 40 | 7 | 500 |

TABLE 8-continued

| Example | Time (min) | Drug 3 Concentration (μg/mL) | AUC (min * μg/mL) |
|---|---|---|---|
|  | 90 | 0 | 700 |
|  | 1200 | 0 | 700 |
| C9 | 0 | <1 | <1 |
|  | 4 | <1 | <1 |
|  | 10 | <1 | <1 |
|  | 20 | <1 | <1 |
|  | 40 | <1 | <1 |
|  | 90 | <1 | <1 |
|  | 1200 | <1 | <1 |

The concentrations of drug obtained in in vitro dissolution tests are shown in Table 8. Results from dissolution tests of Example 6, and Controls C8 and C9, are summarized in Table 9.

TABLE 9

| Example | Matrix Material* | Drug 3 Conc. in the Dispersion (wt %) | Concentration Enhanc. Polymer* | $C_{max,90}$ (µg/mL) | $AUC_{90}$ (min*µg/mL) | $C_{1200}$ (µg/mL) |
|---|---|---|---|---|---|---|
| 6 | PVP | 25 | HPMCAS | 51 | 3300 | 13 |
| C8 | PVP | 25 | None | 29 | 700 | <1 |
| C9 | none | C | None | <1 | <1 | <1 |

*Polymer designations: HPMCAS = hydroxypropyl methyl cellulose acetate succinate, PVP = polyvinyl pyrrolidone.

These results show that the performance of Example 6 containing a drug/matrix dispersion and concentration-enhancing polymer was much better than that of the dispersion alone (Control C8) and undispersed amorphous drug (Control C9). The $C_{max90}$ of Example 6 was 1.8-fold that of Control C8, and the $AUC_{90}$ was 4.7-fold that of C8, and the $C_{max90}$ of Example 6 was at least 51-fold that of Control C9, and the $AUC_{90}$ was at least 3300-fold that of C9.

Examples 7 and 8

This example discloses the use of other concentration-enhancing polymers to obtain improved performance. The Drug 3/PVP drug/matrix dispersion of Example 6 is mixed with concentration-enhancing polymers to form a composition of the present invention. For the composition of Example 7, about 30 wt % to 80 wt % of the Drug 3/PVP dispersion is mixed with 70 wt % to 20 wt % cellulose acetate phthalate (CAP) to form a solid physical mixture. For the composition of Example 8, about 30 wt % to 80 wt % of the Drug 3/PVP dispersion is mixed with about 70 wt % to 20 wt % hydroxypropyl methyl cellulose (HPMC) to form a solid physical mixture.

In vitro dissolution tests are performed using the compositions of Examples 7 and 8 as follows. A sample of each of the compositions containing 1.8 mg of Drug 3 is added to microcentrifuge tubes. The tubes are placed in a 37° C. temperature-controlled chamber, and 1.8 mL PBS is added. The solutions are then sampled as described in Example 1 and analyzed using HPLC.

Example 9

A drug/matrix dispersion was prepared by forming an amorphous dispersion of 25 wt % 5-chloro-1H-indole-2-carboxylic acid [(1S)-benzyl-3-((3R,4S)-dihydroxypyrrolidin-1-yl-)-(2R)-hydroxy-3-oxypropyl]amide ("Drug 4") and 75 wt % PVP. The dispersion was formed by spray-drying a solution containing 0.33 wt % Drug 4 and 0.99 wt % PVP in acetone, using a "mini" spray-drier as described in Example 1, except that the nitrogen was heated to 100° C. The resulting dispersion contained 25 wt % Drug 4.

Example 9 was prepared by combining the above amorphous dispersion with the concentration-enhancing polymer PVA (polyvinyl acetate/polyvinyl alcohol, 88% hydrolyzed, average molecular weight 85,000-146,000; Aldrich Chemical Co.). 14.4 mg of the dispersion of Example 9 was added to microcentrifuge tubes. Tests were performed in duplicate. The tubes were placed in a 37° C. temperature-controlled chamber, and 1.8 mL PBS with 7.2 mg PVA was added. The tests were sampled as described in Example 1, and analyzed using HPLC. HPLC analysis was performed using a Zorbax SB $C_{18}$ column, with a mobile phase of 35 vol. % water and 65 vol. % methanol. UV absorbance of Drug 4 was measured at 297 nm.

For Control C10, in vitro dissolution tests were performed using the procedures described above except that 14.4 mg of the amorphous dispersion of Example 9 was tested without concentration-enhancing polymer (PVA) in the test solution.

For Control C11, 3.6 mg of undispersed amorphous Drug 4 was tested (without concentration-enhancing polymer in the test solution) using the procedures described above. The concentrations of drug obtained in in vitro dissolutions tests are shown in Table 10.

TABLE 10

| | | Drug 4 | |
|---|---|---|---|
| Example | Time (mins) | Concentration (µg/mL) | AUC (min * µg/mL) |
| 9 | 0 | 0 | 0 |
| | 4 | 907 | 1,800 |
| | 10 | 939 | 7,400 |
| | 20 | 983 | 17,000 |
| | 40 | 980 | 36,600 |
| | 90 | 980 | 85,600 |
| | 1200 | 1028 | 1,200,000 |
| C10 | 0 | 0 | 0 |
| | 4 | 739 | 1,500 |
| | 10 | 731 | 5,900 |
| | 20 | 726 | 13,200 |
| | 40 | 715 | 27,600 |
| | 90 | 697 | 62,900 |
| | 1200 | 674 | 823,800 |
| C11 | 0 | 0 | 0 |
| | 4 | 360 | 700 |
| | 10 | 382 | 2,900 |
| | 20 | 372 | 6,700 |
| | 40 | 345 | 13,900 |
| | 90 | 262 | 29,100 |
| | 1200 | 154 | 259,800 |

Results from dissolution tests of Example 9, and Controls C10 and C11, are summarized in Table 11.

TABLE 11

| Example | Matrix Material* | Drug 4 Conc. in the Dispersion (wt %) | Conc. Enhancing Polymer* | $C_{max,90}$ (µg/mL) | $AUC_{90}$ (min*µg/mL) | $C_{1200}$ (µg/mL) |
|---|---|---|---|---|---|---|
| 9 | PVP | 25 | PVA | 983 | 85,600 | 1028 |
| C10 | PVP | 25 | none | 739 | 62,900 | 674 |
| C11 | None | — | none | 382 | 29,100 | 154 |

*Polymer designations: PVP = polyvinyl pyrrolidone, PVA = polyvinyl acetate/polyvinyl alcohol.

These results show that Example 9 consisting of a drug/matrix dispersion and concentration-enhancing polymer provided concentration-enhancement relative to the dispersion alone (Control C10) and undispersed amorphous drug (Control C11). The $C_{max90}$ of Example 9 was 1.33-fold that of control C10, and the $AUC_{90}$ was 1.36-fold that of C10. The $C_{max90}$ of Example 9 was 2.57-fold that of control C11, and the $AUC_{90}$ was 2.94-fold that of C11.

Example 10

This example discloses another low-solubility drug. A drug/matrix is dispersion of amorphous drug and matrix was prepared by forming an amorphous dispersion of 25 wt % 5-(2-(4-(3-benzisothiazolyl)-piperazinyl)ethyl-6-chlorooxindole mesylate ("Drug 5") and 75 wt % PVP. The dispersion was formed by spray-drying a solution containing 0.5 wt % Drug 5 and 0.5 wt % PVP in methanol, using a "mini" spray-drier as described in Example 1, except that the nitrogen was heated to 120° C. The resulting amorphous dispersion contained 50 wt % Drug 5.

Example 10 was prepared by combining the above amorphous dispersion with the concentration-enhancing polymer hydroxypropyl methylcellulose (HPMC E3 Prem LV, Dow Chemical Co.). 1.4 mg of the amorphous dispersion was added to microcentrifuge tubes. The tubes were placed in a 37° C. temperature-controlled chamber, and 1.8 mL PBS containing 0.5 wt % sodium taurocholic acid/1-palmitoyl-2-oleyl-sn-glycero-3-phosphocholine (MFDS, pH 6.5) and 0.4 mg HPMC was added. The tests were sampled as described in Example 1, and analyzed using HPLC.

TABLE 12

| Example | Time (mins) | Drug 5 Concentration (µg/mL) | AUC (min * µg/mL) |
|---|---|---|---|
| 10 | 0 | 0 | 0 |
|  | 4 | 162 | 300 |
|  | 10 | 35 | 900 |
|  | 20 | 33 | 1,300 |
|  | 40 | 13 | 1,700 |
|  | 90 | 10 | 2,300 |
|  | 1200 | 10 | 13,400 |
| C12 | 0 | 0 | 0 |
|  | 4 | 10 | 0 |
|  | 10 | 13 | 100 |
|  | 20 | 16 | 200 |
|  | 40 | 15 | 500 |
|  | 90 | 7 | 1,100 |
|  | 1200 | 30 | 21,600 |
| C13 | 0 | 0 | 0 |
|  | 4 | 16 | 0 |
|  | 10 | 8 | 100 |
|  | 20 | 5 | 200 |
|  | 40 | 4 | 300 |
|  | 90 | 4 | 500 |
|  | 1200 | 4 | 4,900 |

Results from dissolution tests of Example 10, and Controls C12 and C13, are summarized in Table 13.

TABLE 13

| Example | Matrix Material* | Drug 5 Conc. in the Dispersion (wt %) | Conc. Enhanc.Polymer* | $C_{max,90}$ (µg/mL) | $AUC_{90}$ (min*µg/mL) | $C_{1200}$ (µg/mL) |
|---|---|---|---|---|---|---|
| 10 | PVP | 50 | HPMC | 162 | 2300 | 10 |
| C12 | PVP | 50 | none | 16 | 1100 | 30 |
| C13 | None | — | none | 16 | 500 | 4 |

*Polymer designations: PVP = polyvinyl pyrrolidone, HPMC = hydroxypropyl methylcellulose.

For Control C12, in vitro dissolution tests were performed using the procedures described above except that 1.4 mg of the amorphous dispersion was tested without concentration-enhancing polymer (HPMC) in the test solution.

For Control C13, 0.44 mg of undispersed amorphous Drug 5 was tested (without concentration-enhancing polymer in the test solution) using the procedures described above. The concentrations of drug obtained in in vitro dissolution tests are shown in Table 12.

These results show that the composition of Example 10, consisting of a drug/matrix dispersion and concentration-enhancing polymer provided concentration-enhancement relative to the dispersion alone (Control C12) and undispersed amorphous drug (Control C13). The $C_{max90}$ of Example 10 was 10-fold that of Control C12, and the $AUC_{90}$ was 2.1-fold that of Control C12. The $C_{max90}$ of Example 10 was 10-fold that of Control C13, and the $AUC_{90}$ was 4.6-fold that of Control C13.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A pharmaceutical composition comprising a mixture of the following components (a) and (b):
   (a) a solid dispersion comprising a low-solubility acid sensitive drug a major portion of which is amorphous and a matrix selected from the group consisting of a neutral matrix and a basic matrix, said matrix being selected from the group consisting of polyethylene glycols, polyoxyethylene glycols, polyethylene-polypropylene glycol copolymers, polyethylene oxides, polyvinylpyrrolidone, polyvinyl alcohol, polyethylene-vinyl alcohol copolymers, polyvinyl alcohol polyvinyl acetate copolymers, carboxylic acid-functionalized polymethacrylates, amine-functionalized polymethacrylates, xanthan gum, carrageenan, hydroxypropyl cellulose, hydroxypropyl methyl cellulose, carboxy methyl cellulose, chitosan, chitin, polydextrose, dextran and starch; and
   (b) an acidic concentration-enhancing polymer selected from the group consisting of hydroxypropyl methyl cellulose acetate succinate, hydroxypropyl methyl cellulose phthalate, cellulose acetate phthalate, cellulose acetate trimellitate, and blends thereof.

2. The composition of claim 1 wherein said drug has a weight ratio to said matrix of said dispersion of less than 20.

3. The composition of claim 1 wherein said drug in said dispersion has a crystallization rate that is less than 90% of a crystallization rate of said drug in undispersed amorphous form.

4. The composition of claim 1 wherein said matrix is selected from the group consisting of xanthan gum, carrageenan, hydroxypropyl cellulose, hydroxypropyl methyl cellulose, carboxy methyl cellulose, chitosan, chitin, polydextrose, dextran and starch.

5. The composition of claim 1 wherein said dispersion is substantially homogeneous.

6. The composition of claim 1 wherein said dispersion is completely homogeneous.

7. The composition of claim 1 wherein said composition is a solid mixture in which said concentration-enhancing polymer is suspended as a separate phase within said dispersion.

8. The composition of claim 1 wherein said composition is a mixture of particles of said dispersion and particles of said concentration enhancing polymer.

9. The composition of claim 8 wherein said mixture is formed by at least one of dry granulation and wet granulation.

10. The composition of claim 1 wherein said dispersion and said concentration-enhancing polymer are each in separate regions.

11. The composition of claim 1 wherein said drug is selected from the group consisting of antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol reducing agents, antiobesity agents, autoimmune disorder agents, anti-impotence agents, antibacterial and antifungal agents, hypnotic agents, anti-Parkinsonism agents, anti-Alzheimer's disease agents, antibiotics, antidepressants, antiviral agents, anti-atherosclerotic agents, glycogen phosphorylase inhibitors, and cholesterol esterase transfer protein inhibitors.

12. A method of administering a drug comprising administering the pharmaceutical composition of claim 1 to a patient in need of said drug.

13. The method of claim 12 wherein said dispersion is administered separately from said concentration-enhancing polymer.

14. The method of 12 wherein said dispersion and said concentration-enhancing polymer are administered at approximately the same time.

15. The method of claim 12 wherein said dispersion and said concentration-enhancing polymer are present in a single dosage form.

* * * * *